United States Patent
Morley

(10) Patent No.: US 9,145,587 B2
(45) Date of Patent: Sep. 29, 2015

(54) METHOD FOR DNA BREAKPOINT ANALYSIS

(75) Inventor: Alexander Alan Morley, Glenelg (AU)

(73) Assignee: MONOQUANT PTY LTD, Adelaide (AU)

(*) Notice: Subject to any disclaimer, the term of this patent is extended or adjusted under 35 U.S.C. 154(b) by 342 days.

(21) Appl. No.: 12/130,049

(22) Filed: May 30, 2008

(65) Prior Publication Data

US 2009/0202999 A1    Aug. 13, 2009

Related U.S. Application Data

(60) Provisional application No. 60/941,419, filed on Jun. 1, 2007.

(51) Int. Cl.
  C12P 19/34    (2006.01)
  C12Q 1/68    (2006.01)

(52) U.S. Cl.
  CPC .................................. *C12Q 1/6858* (2013.01)

(58) Field of Classification Search
  USPC ..................................................... 435/6, 91.2
  See application file for complete search history.

(56) References Cited

U.S. PATENT DOCUMENTS

| | | | |
|---|---|---|---|
| 6,027,889 A * | 2/2000 | Barany et al. | 435/6.12 |
| 6,355,422 B1 | 3/2002 | Liu et al. | |
| 2002/0146729 A1 * | 10/2002 | Liu et al. | 435/6 |
| 2003/0198977 A1 * | 10/2003 | Nolan et al. | 435/6 |
| 2006/0234234 A1 * | 10/2006 | Van Dongen et al. | 435/6 |
| 2010/0086918 A1 * | 4/2010 | Carson et al. | 435/6 |

FOREIGN PATENT DOCUMENTS

| | | |
|---|---|---|
| JP | 2006-075126 | 3/2006 |
| JP | 2006-174806 | 7/2006 |

(Continued)

OTHER PUBLICATIONS

Rychlik et al., Nucleic Acids Research 17(21), 8543-8551 (1989).*

(Continued)

*Primary Examiner* — Kenneth Horlick
(74) *Attorney, Agent, or Firm* — Knobbe, Martens, Olson & Bear LLP

(57) ABSTRACT

The present invention relates to a method for identifying a DNA breakpoint and agents for use therein. More particularly, the present invention provides a method for identifying a gene translocation breakpoint based on the application of a novel multiplex DNA amplification technique. The method of the present invention facilitates not only the identification of the breakpoint position but, further, enables the isolation of the DNA segment across which the breakpoint occurs. This provides a valuable opportunity to conduct further analysis of the breakpoint region, such as to sequence across this region. The method of the present invention is useful in a range of applications including, but not limited to, providing a routine means to characterize the gene breakpoint associated with disease onset in a patient and thereby enable the design of patient specific probes and primers for ongoing monitoring of the subject disease condition. In addition to monitoring the progression of a condition characterized by the existence of the breakpoint, there is also enabled assessment of the effectiveness of existing therapeutic drugs and/or new therapeutic drugs and, to the extent that the condition is a neoplasm, prediction of the likelihood of a subject's relapse from a remissive state.

11 Claims, 8 Drawing Sheets

(56) References Cited

FOREIGN PATENT DOCUMENTS

| JP | 2007-508824 | | 4/2007 |
|----|-------------|---|--------|
| WO | WO 2004/033728 | A2 | 4/2004 |
| WO | WO 2005/038039 | | 4/2007 |
| WO | WO 2008/016615 | A2 | 2/2008 |

OTHER PUBLICATIONS

Marin, C., et al., "Multiplex-polymerase chain reaction assay for the detection of prognostically significant translocation in acute lymphoblastic leukemia" Haematologica., 2001, vol. 86, pp. 1254-1260.

Metzler, M., et al., "Asymmetric multiplex-polymerase chain reaction—a high throughput method for detection and sequencing genomic fusion sites in t(4;11)" British Journal of Haematology, 2004, vol. 124, pp. 47-64.

Luthra, R., et al., "TaqMan RT-PCR assay coupled with capillary electrophoresis for quantification and identification of bcr-abl transcript type" Modern Pathology, 2004, vol. 17, pp. 96-103.

International Search Report dated Jul. 23, 2008 for PCT/AU2008/000779.

Heath et al., "Universal primer quantitative fluorescent multiplex (UPQFM) PCR: a method to detect major and minor rearrangements of the low density lipoprotein receptor gene," Journal of Medical Genetics, 37(4):272-280 (2000).

Langer et al., "Analysis of t(9;11) Chromosomal Breakpoint Sequences in Childhood Acute Leukemia: Almost Identical *MLL* Breakpoints in Therapy-Related AML After Treatment Without Etoposides," Genes, Chromosomes & Cancer, 36:393-401 (2003).

Liu et al., "A Novel Approach for Determining Cancer Genomic Breakpoints in the Presence of Normal DNA," PLoS One, 2(4):e380, pp. 1-8 (2007).

McHale et al., "Prenatal origin of childhood acute myeloid leukemias harboring chromosomal rearrangements t(15;17) and inv(16)," Blood, 101(11):4640-4641 (2003).

Shimizu et al., "Universal Fluorescent Labeling (UFL) Method for Automated Microsatellite Analysis," DNA Research, 9:173-178 (2002).

Supplementary European Search Report for European Application No. 08 75 6871 dated Aug. 18, 2010.

Office Action mailed Mar. 26, 2013 for Japanese Application No. 2010-509632.

Patent Examination Report issued Oct. 10, 2012 for Australian Application No. 2008255569.

* cited by examiner

FIGURE 4

Patient 1 – GS

```
                                                    gtgggccccccccgtttccgtg
123721  tacagggcacctgcagggagggcaggcagctagcctgaaggctgatccccccttcctgtt
123781  agcacttttgatgggactagtggactttggttcagaaggaagagctatgcttgttagggc
123841  ctcttgtctcctcccaggagtggacaaggtgggttaggagcagtttctccctgagtggct
123901  gc*            <-BCR           ABL->     *caccacgtctggctaa
 55621  ttttttgtattttagtagagatggggtttcaacatgttagccaggctggtctcgaactcc
 55681  tgacctcaggtgatccacccgcctgggccctccaaagtgctgggattacaggcaggagcc
 55741  actgtgcccggcctgacctcatatttgaataccgagttttagttctggaggagctgcagg
 55801  ttttatgaaaagggaacacatttgattcctcagagcagccacaggccagctctctgaagt
 55861  aaagtgcacgtgtgcatgtgtgtgcacactcacacacacgtacacacacattcacaaata
 55741  actgtgcccggcctgacctcatatttgaataccgagttttagttctggaggagctgcagg
```

Patient 3 – ME

```
125041  tttgggaggctgaggcaggtggatcgcttgagctcaggagttggagaccagcctgaccaa
125101  catggtgaaaccctgtgtctactaaaaatacaaagattagccgggctaggcagtgggcac
125161  ctgtaatcacaactgcttgggaggctgagggaagagaatcgcttgaacccaggaggcgga
125221  ggttgcagtgagccgagcttgtgccactgcattccagcctgggcgacagag* <-BCR
                                      ABL->           *ggtctcact
 28981  ctgttgaactcctggtggcctcaagggatcctcctacctcggcctcacaaagtattggaa
 29041  ttacaggtgtgagtcactgcagctggccttcacttatcactgtgaggagtaaacagctgc
 29101  atggtgggcttaatgccatctaacacgagtgactccatgttcagacagtaggatcacaaa
 29161  tgattattatatagcaatgaatggccacaggtacatagactaaggagccacatccctgct
```

Figure 4 (cont'd)

Patient 5 – AB

| | |
|---|---|
| 124021 | cctccagctacctgccagccggcacttttggtcaagctgttttgcattcactgttgcaca |
| 124081 | tatgctcagtcacacacacagcatacgctatgcacatgtgtccacacacacccccacccac |
| 124141 | atcccacatcaccccgacccctctgctgtccttggaaccttattacacttcgagtcact |
| 124201 | ggtttgcctgtattgtgaaaccagctggatcc*        <- BCR |
| | ABL ->                              *ttatttataacaacattttc |
| 94081 | agcgtggcaactgcagtttcagaatggtggaattataccagtcagagagagatgcaaatg |
| 94141 | atttaaaataggaagaaagcaggtgtctggcccagaggaccagattaagaagaccccatg |
| 94201 | agagttacaatagttagtgaaaatggtgcttctgcaaacctcatgtctacagaagctggt |

Patient 6 – CH

| | |
|---|---|
| 125521 | tgcaccttcataacataatctttctcctgggcccctgtctctggctgcctcataaacgct |
| 125581 | ggtgtttccctcgtgggcctccctgcatccctgcatctcctcccgggtcctgtctgtgag |
| 125641 | caatacagcgtgacaccctacgctgccccgtggtcccgggcttgtctctccttgcctccc |
| 125701 | tgttacctttctttctatctcttccttgccccg*        <- BCR |
| | ABL ->                              *gtgagctccgc |
| 81961 | ctcctgtcagatcagtggcggcattagtttctcataggagcatgaaatctattgtgaaca |
| 82021 | gtacatgcgatggatccaggttgcgtgctcctagtgagaatctaatgcctgaggatctct |
| 82081 | cattgtctcttatcactcccagataggactgtctagttgcaggaaaacaagctcagggct |
| 82141 | cccactgattctacattacagtgggttgtataattattatatattacaatgtaataataa |

Figure 5
A) ABL
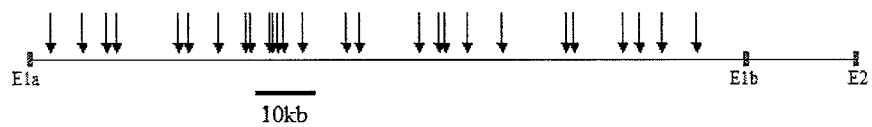
B) BCR
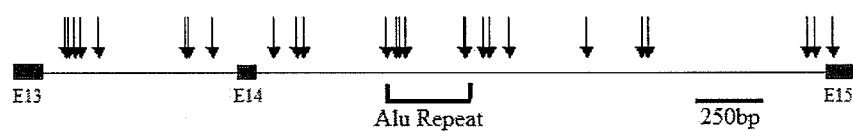

METHOD FOR DNA BREAKPOINT ANALYSIS

CROSS REFERENCE TO RELATED APPLICATION

This application claims the benefit and priority to International Application No. PCT/AU2008/000779; filed May 30, 2008, which designated the United States and was published in English and claims the benefit of priority to U.S. Provisional No. 60/941,419, filed Jun. 1, 2007. The disclosures of the above-referenced applications are hereby expressly incorporated by reference in their entireties.

SEQUENCE LISTING

The present application is being filed along with a Sequence Listing in electronic format. The Sequence Listing is provided as a file entitled DAVI332_001APC.TXT, created May 30, 2008, which is 91 Kb in size. The information in the electronic format of the Sequence Listing is incorporated herein by reference in its entirety.

FIELD OF THE INVENTION

The present invention relates to a method for identifying a DNA breakpoint and agents for use therein. More particularly, the present invention provides a method for identifying a gene translocation breakpoint based on the application of a novel multiplex DNA amplification technique. The method of the present invention facilitates not only the identification of the breakpoint position but, further, enables the isolation of the DNA segment across which the breakpoint occurs. This provides a valuable opportunity to conduct further analysis of the breakpoint region, such as to sequence across this region. The method of the present invention is useful in a range of applications including, but not limited to, providing a routine means to characterise the gene breakpoint associated with disease onset in a patient and thereby enable the design of patient specific probes and primers for ongoing monitoring of the subject disease condition. In addition to monitoring the progression of a condition characterised by the existence of the breakpoint, there is also enabled assessment of the effectiveness of existing therapeutic drugs and/or new therapeutic drugs and, to the extent that the condition is a neoplasm, prediction of the likelihood of a subject's relapse from a remissive state.

BACKGROUND OF THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Bibliographic details of the publications referred to by author in this specification are collected alphabetically at the end of the description.

Chromosomal translocations bring the previously unlinked segments of the genome together by virtue of the exchange of parts between non-homologous chromosomes. Although some translocations are not associated with a new phenotype, others may result in disease due to the modulation of protein expression or the synthesis of a new fusion protein.

There are two main types of chromosomal translocations which occur, these being reciprocal translocations (also known as non-Robertsonian) and Robertsonian translocations. Further, translocations can be balanced (in an even exchange of material with no genetic information extra or missing) or unbalanced (where the exchange of chromosome material is unequal resulting in extra or missing genes).

Reciprocal (non-Robertsonian) translocations usually result in an exchange of material between non-homologous chromosomes and are found in about 1 in 600 newborns. Such translocations are usually harmless and may be found through prenatal diagnosis. However, carriers of balanced reciprocal translocations exhibit an increased risk of creating gametes with unbalanced chromosome translocations thereby leading to miscarriages or children with abnormalities.

Robertsonian translocations involve two acrocentric chromosomes that fuse near the centromere region with loss of the short arms. The resulting karyotype has only 45 chromosomes since two chromosomes have fused together. Robertsonian translocations have been observed involving all combinations of acrocentric chromosomes. The most common translocation involves chromosomes 13 and 14 and is seen in about 1 in 1300 persons. Like other translocations, carriers of Robertsonian translocations are phenotypically normal, but exhibit a risk of unbalanced gametes which lead to miscarriages or abnormal offspring. For example, carriers of Robertsonian translocations involving chromosome 21 exhibit a higher probability of having a child with Down syndrome.

Diseases which may result from the occurrence of a translocation include:
  (i) Cancer—several forms of cancer are caused by translocations; this mainly having been described in leukemia (eg. acute myelogenous leukemia and chronic myelogenous leukemia).
  (ii) Infertility—this can occur where one of the would-be parents carries a balanced translocation, where the parent is asymptomatic but conceived foetuses are not viable.
  (iii) Down syndrome—in some cases this is caused by a Robertsonian translocation of about a third of chromosome 21 onto chromosome 14.

Specific examples of chromosomal translocations and the disease with which they are associated include:
  t(2;5)(p23;q35)—anaplastic large cell lymphoma
  t(8;14)—Burkitt's lymphoma (c-myc)
  t(9;22)(q34;q11)—Philadelphia chromosome, CML, ALL
  t(11;14)—Mantle cell lymphoma (Bcl-1)
  t(11;22)(q24;q11.2-12)—Ewing's sarcoma
  t(14;18)(q32;q21)—follicular lymphoma (Bcl-2)
  t(17;22)—dermatofibrosarcoma protuberans
  t(15;17)—acute promyelocytic leukemia (pml and retinoic acid receptor genes)
  t(1;12)(q21;p13)—acute myelogenous leukemia
  t(9;12)(p24;p13)—CML, ALL (TEL-JAK2)
  t(X;18)(p11.2;q11.2)—Synovial sarcoma
  t(1;11)(q42.1;q14.3)—Schizophrenia
  t(1;19)—acute pre-B cell leukemia (PBX-1 and E2A genes).

The shorthand t(A;B)(p1;q2) is used to denote a translocation between chromosome A and chromosome B. The information in the second set of parentheses, when given, gives a precise location within the chromosome for chromosomes A and B respectively—with p indicating the short arm of the chromosome, q indicating the long arm, and the numbers of p and q refers to regions, bands and sub-bands seen when staining the chromosomes under microscope.

As detailed above, chronic myelogenous leukemia is an example of a neoplastic condition which is caused by a chromosomal translocation. However, unlike many neoplastic conditions, its treatment prospects are quite good if it can be effectively diagnosed and monitored.

In virtually all cases of chronic myelogenous leukemia, a specific translocation is seen. This translocation involves the reciprocal fusion of small pieces from the long arms of chromosome 9 and 22. The altered chromosome 22 is known as the Philadelphia chromosome (abbreviated as Ph1). When the breakpoint of the Ph1 chromosome was sequenced, it was found that the translocation creates a fusion gene by bringing together sequences from the c-ABL proto-oncogene and another BCR (breakpoint cluster region). The BCR-ABL fusion gene encodes a phosphoprotein (p210) that functions as a dysregulated protein tyrosine kinase and predisposes the cell to become neoplastic. This hypothesis is supported by finding that expression of p210 results in transformation of a variety of hematopoietic cell lines in vitro and that mice transgenic for the human BCR-ABL gene develop a number of hematologic malignancies.

Another well studied example of a translocation generating cancer is seen in Burkitt's lymphoma. In some cases of this B cell tumor, a translocation is seen involving chromosome 8 and one of three other chromosomes (2, 14 or 22). In these cases, a fusion protein is not produced. Rather, the c-myc proto-oncogene on chromosome 8 is brought under transcriptional control of an immunoglobulin gene promoter. In B cells, immunoglobulin promoters are transcriptionally quite active, resulting in over expression of c-myc, which is known from several other systems to exhibit monogenic properties. Accordingly, this translocation results in aberrant high expression of an oncogenic protein.

The classical method of diagnosing chromosomal translocations, such as those observed in chronic myelogenic leukemia, is by karyotyping. For many translocations, however, it is now possible to detect the translocation by PCR, using primers which span the breakpoint. In some cases, the PCR technique can also be used for sensitive detection and monitoring of treatment. Monitoring to determine the effect of treatment has become increasingly important for diseases such as chronic myeloid leukemia and acute promyelocytic leukemia as increasingly effective treatment has been developed. For monitoring in these 2 diseases, the starting material for the PCR is RNA. The translocation breakpoint is within the introns of the respective genes and, as a consequence, RNA splicing removes the sequence of RNA transcribed by introns and results in only one or a very limited number of final mRNA products being produced, despite the very large number of different translocations which are present in the patient population.

However, the use of RNA as the starting material to detect and quantify the translocation by PCR suffers the disadvantage that RNA is a difficult molecule to work with due to its inherent susceptibility to degradation. DNA is a more stable molecule. However, the initial identification and characterisation of the breakpoint in the context of DNA is much more difficult since cluster regions of chromosomal fusion sites often span large introns of several tens of thousands of nucleotides. These sizes are too large for direct coverage by a single PCR reaction. There therefore exists an ongoing need to develop means for routinely conducting breakpoint analyses on DNA samples.

In work leading up to the present invention, a novel multiplex amplification reaction has been developed which enables the localisation and analysis of a breakpoint in a DNA sample. Despite the precise position of the breakpoint being unknown, the method of the present invention nevertheless enables diagnosis of the existence of the breakpoint in a DNA sample and the isolation and analysis of the breakpoint region using a relatively modest and simple multiplex amplification reaction. The design of this amplification reaction results in the advantage that generation of long PCR products is not required. Still further, the optional incorporation of a primer hybridisation tag region at the 5' end of the amplification primers enables the rapid generation of large copy numbers of the amplicons generated using these primers and therefore facilitates the isolation and analysis of the amplicons.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

The subject specification contains nucleotide sequence information prepared using the programme PatentIn Version 3.1, presented herein after the bibliography. Each nucleotide sequence is identified in the sequence listing by the numeric indicator <210> followed by the sequence identifier (eg. <210>1, <210>2, etc). The length, type of sequence (DNA, etc) and source organism for each sequence is indicated by information provided in the numeric indicator fields <211>, <212> and <213>, respectively. Nucleotide sequences referred to in the specification are identified by the indicator SEQ ID NO: followed by the sequence identifier (eg. SEQ ID NO: 1, SEQ ID NO:2, etc.). The sequence identifier referred to in the specification correlates to the information provided in numeric indicator field <400> in the sequence listing, which is followed by the sequence identifier (eg. <400>1, <400>2, etc). That is SEQ ID NO:1 as detailed in the specification correlates to the sequence indicated as <400>1 in the sequence listing One aspect the present invention is directed to a method of identifying a gene breakpoint, said method comprising:
(i) contacting a DNA sample with:
  (a) one or more forward primers directed to a DNA region of the flanking gene or fragment thereof located 5' relative to the gene breakpoint, which primers are optionally operably linked at their 5' end to an oligonucleotide tag; and
  (b) one or more reverse primers directed to a DNA region of the flanking gene or fragment thereof located 3' relative to the gene breakpoint, which primers are optionally operably linked at their 5' end to an oligonucleotide tag;
  wherein the oligonucleotide tags of the forward primers are the same relative to the forward primer tags of step (a) and the oligonucleotide tags of the reverse primers are the same relative to the reverse primer tags of step (a) but which forward primer oligonucleotide tags are different relative to the reverse primer tags;

(ii) amplifying the DNA sample of step (i);
(iii) optionally contacting the amplicon generated in step (ii) with:
- (a) one or more forward primers directed to a DNA region of the flanking gene or fragment thereof located 5' relative to the gene breakpoint, which primers are directed to DNA regions which are located 3' to one or more of the forward primers of step (i) and which primers are optionally operably linked at their 5' end to an oligonucleotide tag; and
- (b) one or more reverse primers directed to a DNA region of the flanking gene or fragment thereof located 3' relative to the gene breakpoint, which primers are directed to DNA regions which are located 5' to one or more of the reverse primers of step (i) and which primers are optionally operably linked at their 5' end to an oligonucleotide tag wherein the oligonucleotide tags of the forward primers are the same relative to the forward primer tags of step (iii)(a) and the oligonucleotide tags of the reverse primers are the same relative to the other reverse primer tags of step (iii)(a) but which forward primer oligonucleotide tags are different relative to the reverse primer tags and which forward and reverse primer tags of step (iii) are different relative to the forward and reverse primer tags of step (i);

The present invention therefore preferably provides a method of identifying a chromosomal gene translocation breakpoint, said method comprising:
(i) contacting a genomic DNA sample with:
- (a) one or more forward primers directed to a DNA region of the flanking gene or fragment thereof located 5' relative to the gene breakpoint, which primers are optionally operably linked at their 5' end to an oligonucleotide tag; and
- (b) one or more reverse primers directed to a DNA region of the flanking gene or fragment thereof located 3' relative to the gene breakpoint, which primers are optionally operably linked at their 5' end to an oligonucleotide tag;

wherein the oligonucleotide tags of the forward primers are the same relative to the forward primer tags of step (a) and the oligonucleotide tags of the reverse primers are the same relative to the reverse primer tags of step (a) but which forward primer oligonucleotide tags are different relative to the reverse primer tags;

(ii) amplifying the DNA sample of step (i);
(iii) optionally contacting the amplicon generated in step (ii) with:
- (a) one or more forward primers directed to a DNA region of the flanking gene or fragment thereof located 5' to the gene breakpoint, which primers are directed to DNA regions which are located 3' to one or more of the forward primers of step (i) and which primers are optionally operably linked at their 5' end to an oligonucleotide tag; and
- (b) one or more reverse primers directed to a DNA region of the flanking gene or fragment thereof located 3' to the gene breakpoint, which primers are directed to DNA regions which are located 5' to one or more of the reverse primers of step (i) and which primers are optionally operably linked at their 5' end to an oligonucleotide tag;

wherein the oligonucleotide tags of the forward primers are the same relative to the forward primer tags of step (iii)(a) and the oligonucleotide tags of the reverse primers are the same relative to the reverse primer tags of step (iii)(a) but which forward primer oligonucleotide tags are different relative to the reverse primer tags and which forward and reverse primer tags of step (iii) are different relative to the forward and reverse primer tags of step (i);

(iv) amplifying the DNA sample of step (iii);
(v) analysing said amplified DNA.

There is therefore preferably provided a method of identifying a gene breakpoint, said method comprising:
(i) contacting a DNA sample with
- (a) one to thirty forward primers directed to a DNA region of the flanking gene or fragment thereof located 5' relative to the gene breakpoint, which primers are optionally operably linked at their 5' end to an oligonucleotide tag; and
- (b) twenty-four to four hundred reverse primers directed to a DNA region of the flanking gene or fragment thereof located 3' relative to the gene breakpoint, which primers are optionally operably linked at their 5' end to an oligonucleotide tag;

wherein the oligonucleotide tags of the forward primers are the same relative to the forward primer tags of step (a) and the oligonucleotide tags of the reverse primers are the same relative to the reverse primer tags of step (a) but which forward primer oligonucleotide tags are different relative to the reverse primer tags;

(ii) amplifying the DNA sample of step (i);
(iii) optionally contacting the amplicon generated in step (ii) with:
- (a) one to thirty forward primers directed to a DNA region of the flanking gene or fragment thereof located 5' relative to the gene breakpoint, which primers are directed to DNA regions which are located 3' to one or more of the forward primers of step (i) and which primers are optionally operably linked at their 5' end to an oligonucleotide tag; and
- (b) twenty-four to four hundred reverse primers directed to a DNA region of the flanking gene or fragment thereof located 3' to the gene breakpoint, which primers are directed to DNA regions which are located 5' to one or more of the reverse primers of step (i) and which primers are optionally operably linked at their 5' end to an oligonucleotide tag;

wherein the oligonucleotide tags of the forward primers are the same relative to the forward primer tags of step (iii)(a) and the oligonucleotide tags of the reverse primers are the same relative to the reverse primer tags of step (iii)(a) but which forward primer oligonucleotide tags are different relative to the reverse primer tags and which forward and reverse primer tags of step (iii) are different relative to the forward and reverse primer tags of step (i);

(iv) amplifying the DNA sample of step (iii);
(v) analysing said amplified DNA.

The present invention therefore provides a method of identifying a gene translocation breakpoint, said method comprising:
(i) contacting a DNA sample with:
- (a) one to thirty forward primers directed to a DNA region of the antisense strand of the flanking gene or fragment thereof located 5' relative to the gene breakpoint, which primers are optionally operably linked at their 5' end to an oligonucleotide tag;
- (b) twenty-four to four hundred reverse primers directed to a DNA region of the flanking gene or fragment thereof located 3' relative to the gene breakpoint, which primers are optionally operably linked at their 5' end to an oligonucleotide tag;

wherein the oligonucleotide tags of the forward primers are the same relative to the forward primer tags of step (a) and the oligonucleotide tags of the reverse primers are the same relative to the reverse primer tags of step (a) but which forward primer oligonucleotide tags are different relative to the reverse primer tags;
   (c) a primer directed to the forward primer oligonucleotide tag of step (i)(a); and
   (d) a primer directed to the reverse primer oligonucleotide tag of step (i)(b);
(ii) amplifying the DNA sample of step (i);
(iii) optionally contacting the amplicon generated in step (ii) with:
   (a) one to thirty forward primers directed to a DNA region of the flanking gene or fragment thereof located 5' relative to the gene breakpoint, which primers are directed to DNA regions which are located 3' to one or more of the forward primers of step (i) and which primers are optionally operably linked at their 5' end to an oligonucleotide tag;
   (b) twenty-four to four hundred reverse primers directed to a DNA region of the flanking gene or fragment thereof located 3' to the gene breakpoint, which primers are directed to DNA regions which are located 5' to one or more of the reverse primers of step (i) and which primers are optionally operably linked at their 5' end to an oligonucleotide tag;
   (c) a primer directed to the forward primer oligonucleotide tag of step (iii)(a); and
   (d) a primer directed to the reverse primer oligonucleotide tag of step (iii)(b);
   wherein the oligonucleotide tags of the forward primers are the same relative to the forward primer tags of step (iii)(a) and the oligonucleotide tags of the reverse primers are the same relative to the reverse primer tags of step (iii)(a) but which forward primer oligonucleotide tags are different relative to the reverse primer tags and which forward and reverse primer tags of step (iii) are different relative to the forward and reverse primer tags of step (i);
(iv) amplifying the DNA sample of step (iii);
(v) analysing said amplified DNA.

According to this preferred embodiment there is provided a method of identifying a chromosomal BCR-ABL translocation breakpoint, said method comprising:
(i) contacting a DNA sample with:
   (a) one or more forward primers directed to a DNA region of BCR or fragment thereof, which primers are optionally operably linked at their 5' end to an oligonucleotide tag; and
   (b) one or more reverse primers directed to a DNA region of ABL or fragment thereof, which primers are optionally operably linked at their 5' end to an oligonucleotide tag;
   wherein the oligonucleotide tags of the forward primers are the same relative to the forward primer tags of step (a) and the oligonucleotide tags of the reverse primers are the same relative to the reverse primer tags of step (a) but which forward primer oligonucleotide tags are different relative to the reverse primer tags;
(ii) amplifying the DNA sample of step (i);
(iii) optionally contacting the amplicon generated in step (ii) with:
   (a) one or more forward primers directed to a DNA region of BCR or fragment thereof, which primers are directed to DNA regions which are located 3' to one or more of the forward primers of step (i) and which primers are optionally operably linked at their 5' end to an oligonucleotide tag; and
   (b) one or more reverse primers directed to ABL or fragment thereof, which primers are directed to DNA regions which are located 5' to one or more of the reverse primers of step (i) and which primers are optionally operably linked at their 5' end to an oligonucleotide tag;
   wherein the oligonucleotide tags of the forward primers are the same relative to the forward primer tags of step (iii)(a) and the oligonucleotide tags of the reverse primers are the same relative to the reverse primer tags of step (iii)(a) but which forward primer oligonucleotide tags are different relative to the reverse primer tags and which forward and reverse primer tags of step (iii) are different relative to the forward and reverse primer tags of step (i);
(iv) amplifying the DNA sample of step (iii);
(v) analysing said amplified DNA.

The present invention therefore preferably provides a method of identifying a chromosomal BCR-ABL translocation breakpoint, said method comprising:
(i) contacting a DNA sample with:
   (a) one to thirty forward primers directed to a DNA region of BCR or fragment thereof, which primers are optionally operably linked at their 5' end to an oligonucleotide tag;
   (b) twenty-four to four hundred reverse primers directed to a DNA region of ABL or fragment thereof, which primers are optionally operably linked at their 5' end to an oligonucleotide tag;
   wherein the oligonucleotide tags of the forward primers are the same relative to the forward primer tags of step (a) and the oligonucleotide tags of the reverse primers are the same relative to the reverse primer tags of step (a) but which forward primer oligonucleotide tags are different relative to the reverse primer tags;
   (c) a primer directed to the forward primer oligonucleotide tag of step (i)(a); and
   (d) a primer directed to the reverse primer oligonucleotide tag of step (i)(b);
(ii) amplifying the DNA sample of step (i);
(iii) contacting the amplicon generated in step (ii) with:
   (a) one to thirty forward primers directed to a DNA region of BCR or fragment thereof, which primers are directed to DNA regions which are located 3' to one or more of the forward primers of step (i) and which primers are optionally operably linked at their 5' end to an oligonucleotide tag;
   (b) twenty-four to four hundred reverse primers directed to a DNA region of ABL or fragment thereof, which primers are directed to DNA regions which are located 5' to one or more of the reverse primers of step (i) and which primers are optionally operably linked at their 5' end to an oligonucleotide tag;
   (c) a primer directed to the forward primer oligonucleotide tag of step (iii)(a); and
   (d) a primer directed to the reverse primer oligonucleotide tag of step (iii)(b);
   wherein the oligonucleotide tags of the forward primers are the same relative to the forward primer tags of step (iii)(a) and the oligonucleotide tags of the reverse primers are the same relative to the reverse primer tags of step (iii)(a) but which forward primer oligonucleotide tags are different relative to the reverse primer tags and which forward and reverse primer tags of step (iii) are different relative to the forward and reverse primer tags of step (i);
(iv) amplifying the DNA sample of step (iii);
(v) isolating and sequencing said amplified DNA.

BRIEF DESCRIPTION OF THE DRAWINGS

FIG. 4 is a representation of the sequences of the breakpoints in 4 patients with chronic myeloid leukemia. The numbers on the left are the Genbank base numbers for the BCR and ABL genes.

FIG. 5 shows the site of the DNA breakpoints in the ABL and BCR genes in the 27 patients with breakpoints isolated and identified. Blue regions in the ABL gene represent exons 1a, 1b and E2. Red regions in the BCR gene represent exons 13, 14 and 15.

Isolation of the BCR-ABL Breakpoint in Chronic Myeloid Leukemia (CML)

Samples from 29 CML patients have been studied using the invention. In 27 of these patients the breakpoint sequences have been isolated and detailed sequencing information obtained. For one patient it has not been possible to amplify the BCR/ABL breakpoint. For the remaining patient a suspected breakpoint has been amplified. Sequence information shows the BCR gene at the 5' end and ABL sequence at the 3' end, however this breakpoint has not been confirmed with primers made specifically for the suspected regions.

Figure 1:
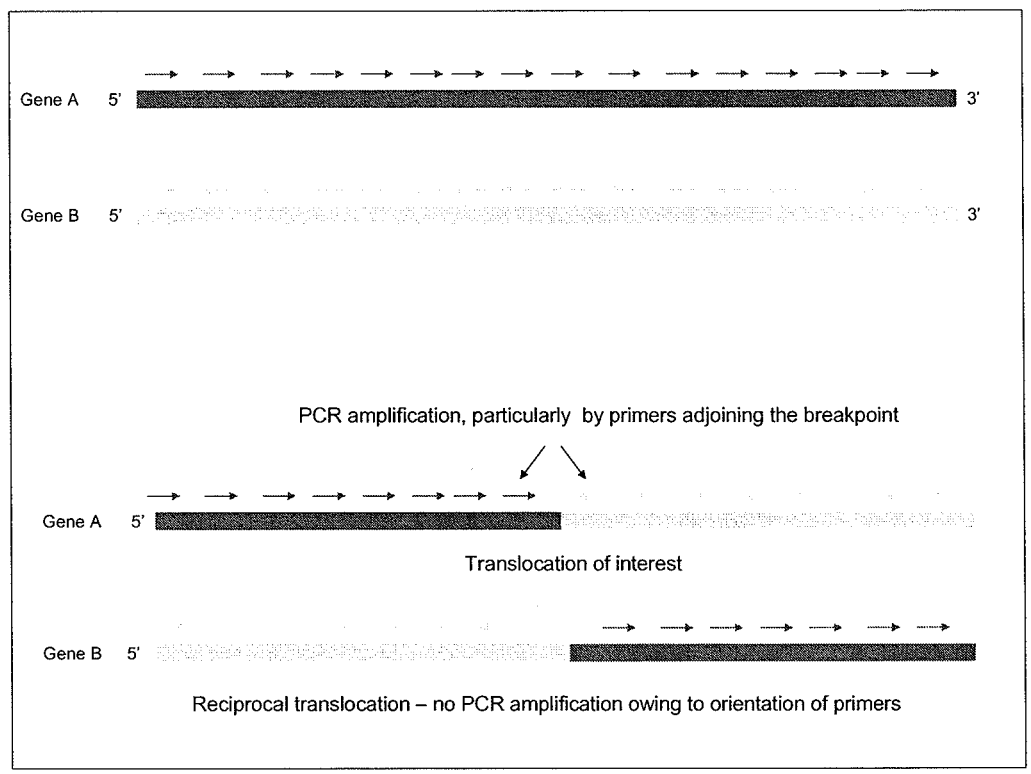
FIG. 1 is a schematic representation of the strategy for amplification of the breakpoint region in the first round PCR. The forward primers for gene A and the reverse primers for gene B are preferably used in pools rather than individually. Only primer pairs which closely straddle the breakpoint will produce efficient amplification. The tags and tag primers are not shown. The strategy for the second round PCR is the same although the forward and reverse primers are just internal to their corresponding primers in the first round. In the case of chronic myeloid leukemia, gene A is the BCR gene and gene B is the ABL gene. Primer binding sites are staggered so that the maximum amplicon size does not exceed 1 kilobase.
Figure 2:
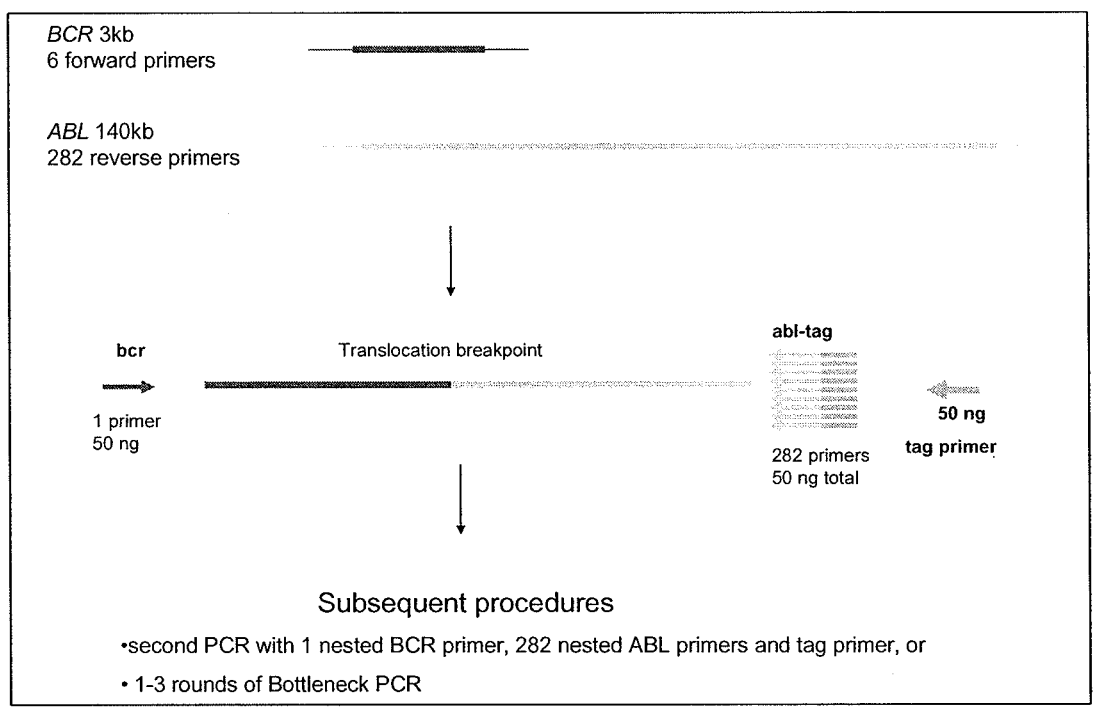
FIG. 2 is a schematic representation of a protocol for isolation of the BCR-ABL translocation breakpoint in chronic myeloid leukemia.
Figure 3:
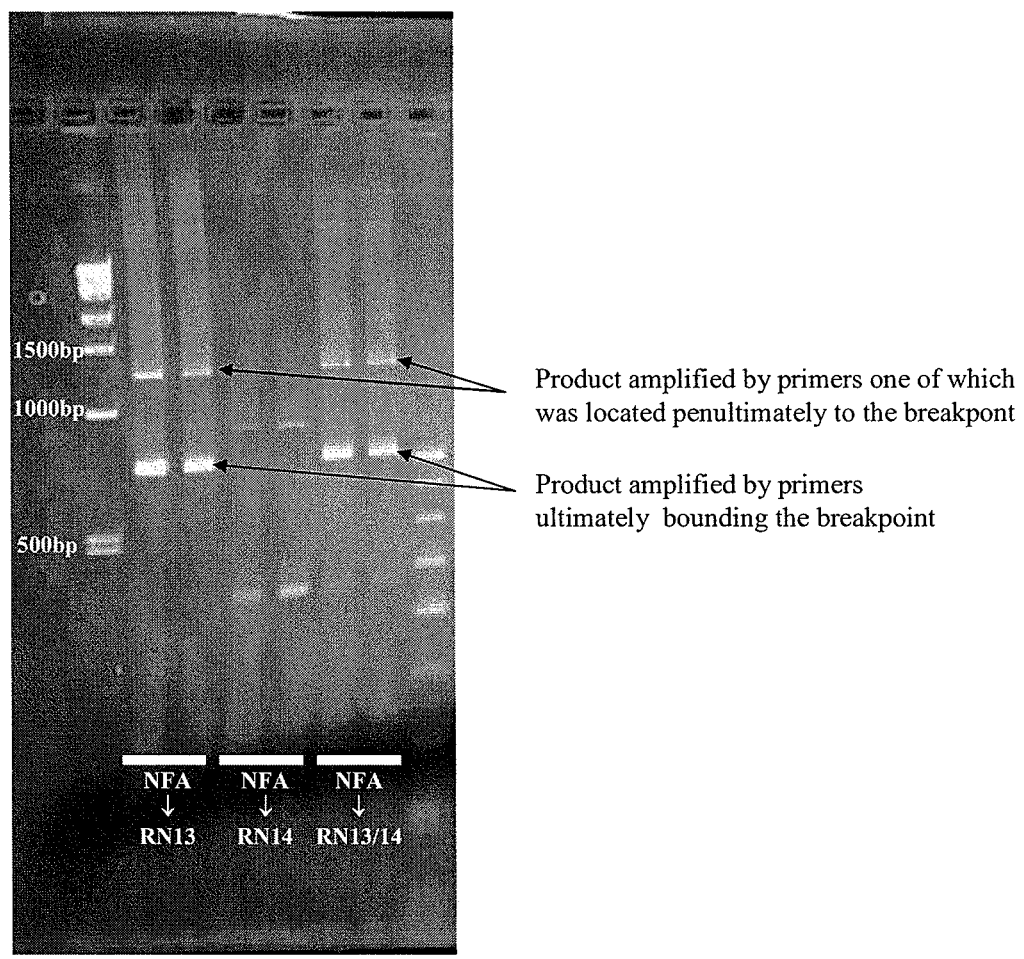
FIG. 3 is an image of the results of electrophoresis showing amplified material from study of one patient. NFA was the pool of 6 forward BCR primers and NFA 13 and NFA 14 were 2 pools each containing 12 reverse ABL primers. NFA 13/14 was a pool containing the 24 ABL primers belonging to pools 13 and 14.
Figure 6:
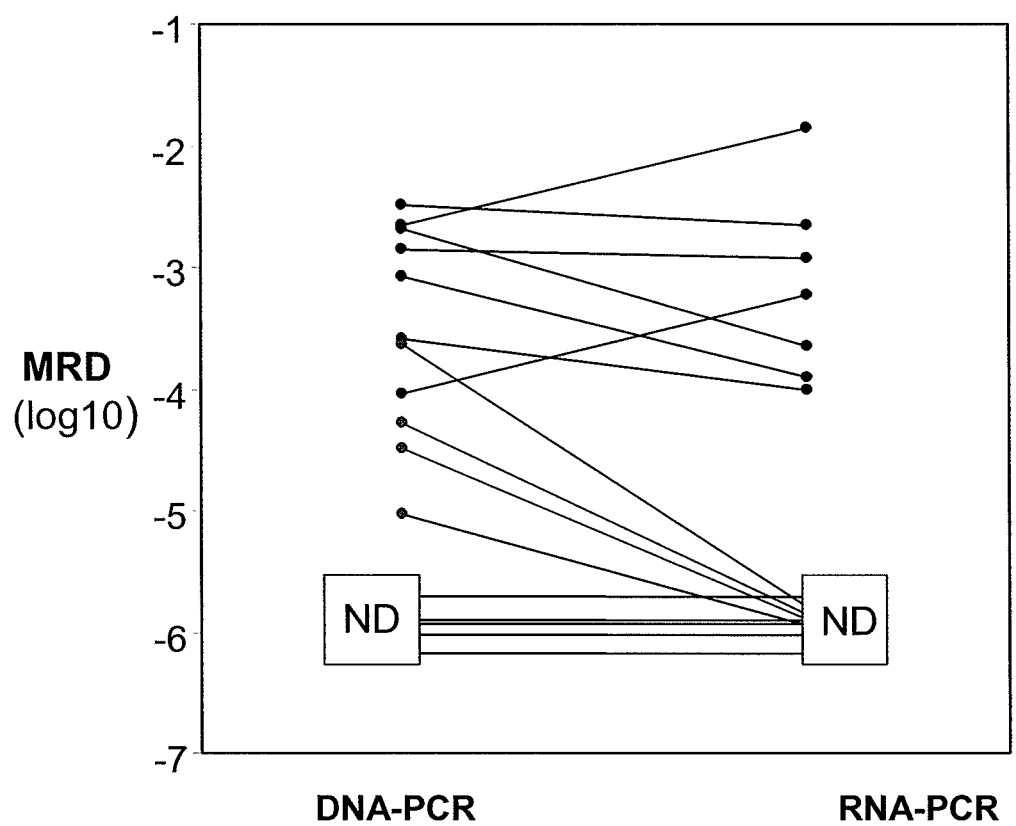

FIG. 6 is a comparison of DNA-based and RNA-based quantification of minimal residual disease (MRD) in samples of blood from 16 patients with CML. ND=not detected. Y-axis shows the number of leukemic cells as a proportion of total cells. The DNA-based PCR used patient-specific primers synthesised using knowledge of the breakpoint sequence in the patient being studied, the RNA-based PCR was the conventional approach using reverse transcription followed by PCR using generic primers. Black symbols show MRD detected by both techniques, red symbols show disease detected only by DNA-PCR and blue symbols show disease not detected. DNA-based PCR appears to be approximately 2 orders of magnitude more sensitive than RNA-based PCR.

Figure 7:
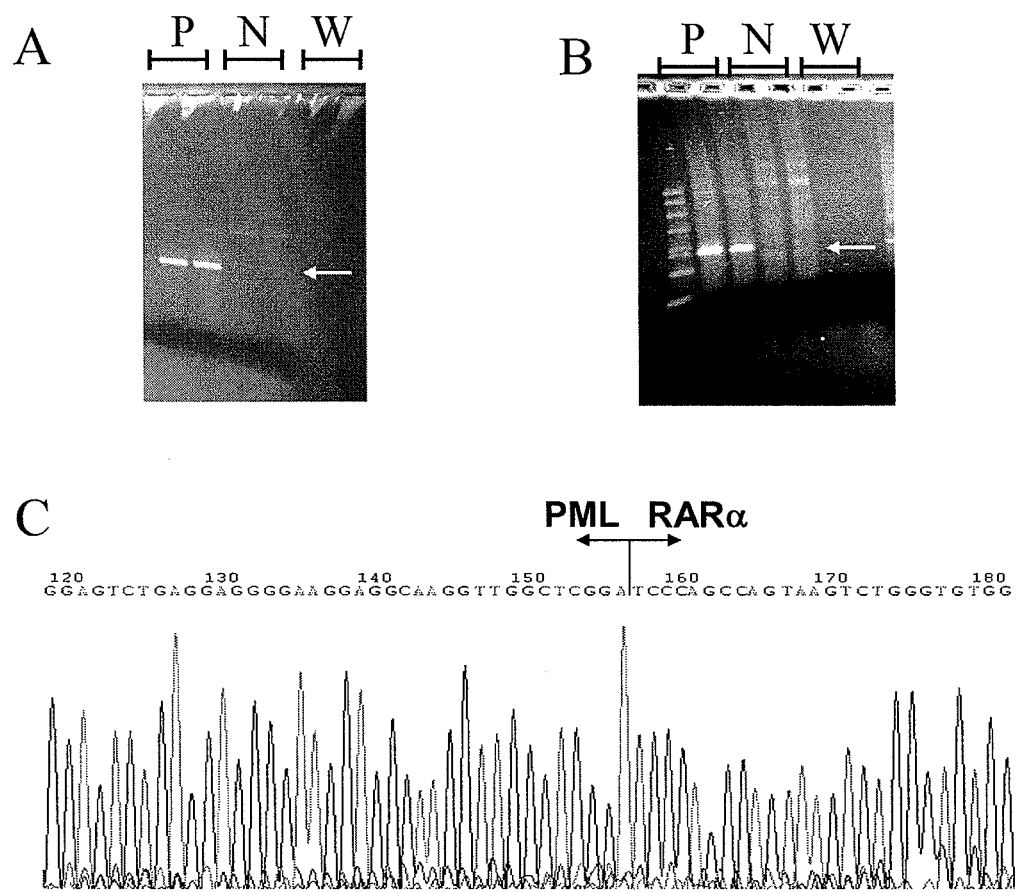

FIG. 7 is an illustration of the isolation of the PML-RARα breakpoint from a sample from the one patient with acute promyelocytic leukemia

DETAILED DESCRIPTION OF THE INVENTION

The present invention is predicated, in part, on the determination that gene translocation breakpoints can be routinely and easily identified, via DNA analysis, by sequentially performing two PCR reactions which use multiple primers directed to the genes flanking the breakpoint which are themselves tagged at their 5' end with a DNA region suitable for use as a primer hybridisation site. The simultaneous use of multiple primers facilitates the performance of a short PCR, rather than the long PCRs which have been performed to date. By sequentially performing a second PCR using primers directed to gene regions internal to those used in the first reaction, amplification of a DNA molecule spanning the breakpoint region can be achieved in a manner which enables the identification and isolation of a smaller amplification product than has been enabled to date in terms of the analysis of genomic DNA. By incorporating unique tag regions which can themselves be targeted by a primer, amplification of the initial amplicon can be rapidly achieved, thereby overcoming any disadvantage associated with the use of a low concentration of starting primer directed to the genes flanking the breakpoint. The method of the present invention therefore provides a simple yet accurate means of identifying and analysing a gene breakpoint using DNA. To this end, it would be appreciated that although the method of the present invention is exemplified by reference to chronic myelogenic leukemia, this method can be applied to any situation in which a gene breakpoint is sought to be identified via a DNA sample.

Accordingly, in one aspect the present invention is directed to a method of identifying a gene breakpoint, said method comprising:

(i) contacting a DNA sample with:
  (a) one or more forward primers directed to a DNA region of the flanking gene or fragment thereof located 5' relative to the gene breakpoint, which primers are optionally operably linked at their 5' end to an oligonucleotide tag; and
  (b) one or more reverse primers directed to a DNA region of the flanking gene or fragment thereof located 3' relative to the gene breakpoint, which primers are optionally operably linked at their 5' end to an oligonucleotide tag; wherein the oligonucleotide tags of the forward primers are the same relative to the forward primer tags of step (a) and the oligonucleotide tags of the reverse primers are the same relative to the reverse primer tags of step (a) but which forward primer oligonucleotide tags are different relative to the reverse primer tags;

(ii) amplifying the DNA sample of step (i);

(iii) optionally contacting the amplicon generated in step (ii) with:
  (a) one or more forward primers directed to a DNA region of the flanking gene or fragment thereof located 5' relative to the gene breakpoint, which primers are directed to DNA regions which are located 3' to one or more of the forward primers of step (i) and which primers are optionally operably linked at their 5' end to an oligonucleotide tag; and
  (b) one or more reverse primers directed to a DNA region of the flanking gene or fragment thereof located 3' relative to the gene breakpoint, which primers are directed to DNA regions which are located 5' to one or more of the reverse primers of step (i) and which primers are optionally operably linked at their 5' end to an oligonucleotide tag
  wherein the oligonucleotide tags of the forward primers are the same relative to the forward primer tags of step (iii)(a) and the oligonucleotide tags of the reverse primers are the same relative to the other reverse primer tags of step (iii)(a) but which forward primer oligonucleotide tags are different relative to the reverse primer tags and which forward and reverse primer tags of step (iii) are different relative to the forward and reverse primer tags of step (i);

(iv) amplifying the DNA sample of step (iii);
(v) analysing said amplified DNA.

It should be understood that in a preferred embodiment of the present invention, where one primer is used in step (i)(a), it is preferable that two or more primers are used in step (i)(b). The converse applies where one primer is used in step (i)(b). Similarly, in another preferred embodiment, where one primer is used in step (iii)(a), it is preferable that two or more primers are used in step (iii)(b). The converse applies where one primer is used in step (iii)(b).

Reference to the "flanking genes" 5' and 3' to the breakpoint should be understood as a reference to the genes or gene fragments on either side of the breakpoint. In terms of the 5' and 3' nomenclature which is utilised in the context of these genes/gene fragments, this should be understood as a reference to the 5'? 3' orientation of the sense strand of double stranded DNA from which the DNA of interest derives. Accordingly, reference to "the flanking gene 5' to the breakpoint" should be understood as a reference to the sense strand of double stranded DNA. To this end, any reference to "gene" or "gene fragment" herein, to the extent that it is not specified, is a reference to the sense strand of double stranded DNA. Reference to the forward primer being directed to the antisense strand of the flanking gene 5' to the breakpoint therefore indicates that the forward primer bears the same DNA sequence as a region of the sense strand 5' to the breakpoint and therefore will bind to and amplify the antisense strand corresponding to that region.

Reference to "gene" should be understood as a reference to a DNA molecule which codes for a protein product, whether that be a full protein or a protein fragment. In terms of chromosomal DNA, the gene will include both intron and exon regions. However, to the extent that the DNA of interest is cDNA, such as might occur if the DNA of interest is vector DNA, there may not exist intron regions. Such DNA may nevertheless include 5' or 3' untranslated regions. Accordingly, reference to "gene" herein should be understood to encompass any form of DNA which codes for a protein or protein fragment including, for example, genomic DNA and cDNA.

Reference to a gene "breakpoint" should be understood as a reference to the point at which a fragment of one gene recombines with another gene or fragment thereof. That is, there has occurred a recombination of two genes such that either one or both genes have become linked at a point within one or both of the genes rather than the beginning or end of one gene being linked to the beginning or end of the other gene. That is, at least one of the subject genes has been cleaved and has recombined with all or part of another gene. The recombination of the two non-homologous gene regions may occur by any method including but not limited to chromosomal gene translocations or in vitro homologous recombinations (such as may occur where a DNA segment is being inserted into a vector or an artificial chromosome or where a vector portion thereof chromosomally integrates in a host cell).

Preferably, the subject gene breakpoint is a chromosomal gene translocation breakpoint. As detailed hereinbefore, chromosomal gene translocations are known to occur and, in some cases, lead to the onset of disease states. Since a gene translocation between two genes will not necessarily result in the breakpoint occurring at precisely the same nucleotide position on the two genes each time the translocation event occurs, it is not possible to assume that the breakpoint position in one patient, such as the Philadelphia chromosome breakpoint in one CML patient, will be the same in another patient. The method of the present invention enables the simple yet accurate determination of a gene breakpoint using DNA.

The present invention therefore preferably provides a method of identifying a chromosomal gene translocation breakpoint, said method comprising:
(i) contacting a genomic DNA sample with:
  (a) one or more forward primers directed to a DNA region of the flanking gene fragment thereof located 5' relative to the gene breakpoint, which primers are optionally operably linked at their 5' end to an oligonucleotide tag; and
  (b) one or more reverse primers directed to a DNA region of the flanking gene or fragment thereof located 3' relative to the gene breakpoint, which primers are optionally operably linked at their 5' end to an oligonucleotide tag;
  wherein the oligonucleotide tags of the forward primers are the same relative to the forward primer tags of step (a) and the oligonucleotide tags of the reverse primers are the same relative to the reverse primer tags of step (a) but which forward primer oligonucleotide tags are different relative to the reverse primer tags;
(ii) amplifying the DNA sample of step (i);
(iii) optionally contacting the amplicon generated in step (ii) with:
  (a) one or more forward primers directed to a DNA region of the flanking gene or fragment thereof located 5' to the gene breakpoint, which primers are directed to DNA regions which are located 3' to one or more of the forward primers of step (i) and which primers are optionally operably linked at their 5' end to an oligonucleotide tag; and
  (b) one or more reverse primers directed to a DNA region of the flanking gene or fragment thereof located 3' to the gene breakpoint, which primers are directed to DNA regions which are located 5' to one or more of the reverse primers of step (i) and which primers are optionally operably linked at their 5' end to an oligonucleotide tag;
  wherein the oligonucleotide tags of the forward primers are the same relative to the forward primer tags of step (iii)(a) and the oligonucleotide tags of the reverse primers are the same relative to the reverse primer tags of step (iii)(a) but which forward primer oligonucleotide tags are different relative to the reverse primer tags and which forward and reverse primer tags of step (iii) are different relative to the forward and reverse primer tags of step (i);
(iv) amplifying the DNA sample of step (iii);
(v) analysing said amplified DNA.

Reference to "DNA" should be understood as a reference to deoxyribonucleic acid or derivative or analogue thereof. In this regard, it should be understood to encompass all forms of DNA, including cDNA and genomic DNA. The nucleic acid molecules of the present invention may be of any origin including naturally occurring (such as would be derived from a biological sample), recombinantly produced or synthetically produced.

Reference to "derivatives" should be understood to include reference to fragments, homologs or orthologs of said DNA from natural, synthetic or recombinant sources. "Functional derivatives" should be understood as derivatives which exhibit any one or more of the functional activities of DNA. The derivatives of said DNA sequences include fragments having particular regions of the DNA molecule fused to other proteinaceous or non-proteinaceous molecules. "Analogs" contemplated herein include, but are not limited to, modifications to the nucleotide or nucleic acid molecule such as modifications to its chemical makeup or overall conformation. This includes, for example, modification to the manner in which nucleotides or nucleic acid molecules interact with other nucleotides or nucleic acid molecules such as at the level of backbone formation or complementary base pair hybridisation. The biotinylation or other form of labelling of a nucleotide or nucleic acid molecules is an example of a "functional derivative" as herein defined.

As detailed hereinbefore, the method of the present invention is predicated on the use of multiple oligonucleotide primers to facilitate the multiplexed amplification of a DNA sample of interest. In one embodiment of the present invention, the DNA sample of interest is a hybrid gene which comprises a portion of one gene (gene A) which is located 5' to the translocation breakpoint and a second gene (gene B) which is located 3' to the translocation breakpoint. In a particular embodiment, gene A is BCR and gene B is ABL. The identification of the existence and nature of a gene translocation breakpoint is achieved by using two or more forward primers directed to gene A and two or more reverse primers directed towards gene B. The primers directed to gene A are designed to hybridise at intervals along gene A and the primers directed to gene B are similarly designed to hybridise at intervals along gene B. In the first round PCR, the primers which will amplify the hybrid gene are the upstream primers which hybridise to that portion of gene A which lies 5' to the breakpoint and the downstream primers which hybridise to that portion of gene B which lies 3' to the breakpoint. Furthermore, since small amplicons are amplified more efficiently than larger amplicons, there will occur selection for amplification directed by the primer pair which hybridises closest to the breakpoint. The same principle holds for the second round primers and, since in one embodiment each second round primer corresponds to an individual first-round primer but hybridises internal to it with regard to the breakpoint, there will be further selection for amplification by the pair of the second round primers which bound the breakpoint. Without limiting the present invention in any way, the second round of PCR amplification provides additional specificity for amplification of the breakpoint region. Following the second round PCR, successful amplification of the sequence surrounding the breakpoint will be evident as a band of amplified material on electrophoresis.

Since it is not known precisely where the breakpoint lies, it is possible that one or more of the internal primers may not hybridise to their target region sequence due to this sequence having been effectively spliced out during the translocation event. However, in one embodiment, the forward and reverse primers selected for the first round amplification are directed to amplifying from the 5' and 3' end regions, respectively, of the gene fragments flanking the breakpoint. The second round primers are then directed to internal regions of the gene fragments flanking the breakpoint, that is, the regions which are closer to the breakpoint than the regions targeted by the first round primers. Again, it would be appreciated that since the precise location of the breakpoint is not known, one or more of these forward and/or reverse primers may not hybridise to the DNA sample due to their target region sequence having been spliced out. In terms of the second round "internal primers", it should be understood that this is a reference to a population of primers of which at least one primer, but preferably all the primers, are designed to amplify the subject DNA from a point which, when considered in the context of the translocated gene itself (rather than the antisense strand or the amplification product), is 3' of the most 3' of the forward primers used in the first round amplification and 5' of the most 5' of the reverse primers used in the first round amplification. By using the approach of a two step amplification using progressively more internally localised primers, amplification of DNA spanning the breakpoint region can be achieved without the requirement to perform long PCRs or to generate very long and cumbersome amplification products.

Reference to a "primer" or an "oligonucleotide primer" should be understood as a reference to any molecule comprising a sequence of nucleotides, or functional derivatives or analogues thereof, the function of which includes hybridisation to a region of a nucleic acid molecule of interest (the DNA of interest also being referred to as a "target DNA") and the amplification of the DNA sequence 5' to that region. It should be understood that the primer may comprise non-nucleic acid components. For example, the primer may also comprise a non-nucleic acid tag such as a fluorescent or enzymatic tag or some other non-nucleic acid component which facilitates the use of the molecule as a probe or which otherwise facilitates its detection or immobilisation. The primer may also comprise additional nucleic acid components, such as the oligonucleotide tag which is discussed in more detail hereinafter. In another example, the primer may be a protein nucleic acid which comprises a peptide backbone exhibiting nucleic acid side chains. preferably, said oligonucleotide primer is a DNA primer.

Reference to "forward primer" should be understood as a reference to a primer which amplifies the target DNA in the DNA sample of interest by hybridising to the antisense strand of the target DNA.

Reference to "reverse primer" should be understood as a reference to a primer which amplifies the target DNA in the DNA sample of interest and in the PCR by hybridising to the sense strand of the target DNA.

The design and synthesis of primers suitable for use in the present invention would be well known to those of skill in the art. In one embodiment, the subject primer is 4 to 60 nucleotides in length, in another embodiment 10 to 50 in length, in yet another embodiment 15 to 45 in length, in still another embodiment 20 to 40 in length, in yet another embodiment 25 to 35 in length. In yet still another embodiment, primer is about 26, 27, 28, 29, 30, 31, 32, 33 or 34 nucleotides in length. Without limiting the invention in any way, the primers are designed in one embodiment to have a $T_M$ of 65 to 70° C. This enables the PCR to use a high annealing temperature, which minimises non-specific annealing and amplification. Each forward or reverse primer for the second round PCR is designed to hybridise to a sequence which is close, either downstream for the forward primer or upstream for the reverse primer, to the hybridisation sequence for its corresponding forward or reverse first-round primer. Designing the corresponding primers to hybridise to closely adjoining sequences minimises the probability that the translocation breakpoint will involve or occur between the hybridisation sequences. even if this does occur, the sequence surrounding the translation breakpoint can still be amplified by the immediately upstream or downstream, as the case may be, primer pair.

In the exemplified embodiment described herein, primers were chosen so that their binding sites were staggered with the separation between adjacent binding sites being approximately 500 bases. This was done so that the amplified material would have range in size, up to a maximum length of approximately 1 kilobase. This strategy is in contrast to the strategy of "Long PCR" which would require fewer primers and a less complex multiplex PCR reaction. The advantages of the strategy of the present invention are that the standard shorter PCR reaction is more robust and the amplified product can be sequenced immediately rather than requiring another set of PCR reactions to break it up into smaller amplicons which are suitable for sequencing.

In terms of the number of primers which are used in the method of the invention, this can be determined by the person of skill in the art. With regard to the total number of primers, the variables which require consideration are the size of the gene region which is being targeted and the distance between the sequences to which the primers hybridise. In order to amplify PCR fragments which are no larger than about 1 kb, the primers can be designed to hybridise at intervals of approximately 500 bases. With regard to CML, nearly all BCR translocations involve one of two regions, each of approximately 3 kb in length. In this case, 12 outer forward primers and 12 corresponding inner primers may be used. The ABL gene, however, is larger, approximately 140 kb in length, and up to 280 outer reverse primers and 280 inner reverse primers may be used. In one particular embodiment, a combination of 6 forward primers and 24 reverse primers is used and in another embodiment a combination of 6 forward primers and 140 reverse primers. The primer number which is selected to be used will depend on the genes involved in the translocation and thus may vary from translocation to translocation and will involve consideration of the competing issues of the number of PCR reactions which are required to be performed versus the probability of generating non-specific products during a PCR reaction. As would be understood by the person of skill in the art, a large number of primers in each individual PCR reaction decreases the number of PCR reactions but increases the probability of non-specific amplification reactions.

In one embodiment, the method of the present invention is performed using at least three primers, in another embodiment at least four primers. In yet another embodiment said invention is performed using 6-10 primers, 6-15 primers, 6-20 primers, 6-25 primers or 6-30 primers. In still another embodiment there is used 5, 6, 7, 8, 9, 10, 11, 12, 13, 14, 15, 16, 17, 18, 19, 20, 21, 22, 23, 24, 25, 26, 27, 28, 29 or 30 primers.

There is therefore preferably provided a method of identifying a gene breakpoint, said method comprising:
(i) contacting a DNA sample with
  (a) one to thirty forward primers directed to a DNA region of the flanking gene or fragment thereof located 5' relative to the gene breakpoint, which primers are optionally operably linked at their 5' end to an oligonucleotide tag; and
  (b) twenty-four to four hundred reverse primers directed to a DNA region of the flanking gene or fragment thereof located 3' relative to the gene breakpoint, which primers are optionally operably linked at their 5' end to an oligonucleotide tag;
  wherein the oligonucleotide tags of the forward primers are the same relative to the forward primer tags of step (a) and the oligonucleotide tags of the reverse primers are the same relative to the reverse primer tags of step (a) but which forward primer oligonucleotide tags are different relative to the reverse primer tags;
(ii) amplifying the DNA sample of step (i);
(iii) optionally contacting the amplicon generated in step (ii) with:
  (a) one to thirty forward primers directed to a DNA region of the flanking gene or fragment thereof located 5' relative to the gene breakpoint, which primers are directed to DNA regions which are located 3' to one or more of the forward primers of step (i) and which primers are optionally operably linked at their 5' end to an oligonucleotide tag; and
  (b) twenty-four to four hundred reverse primers directed to a DNA region of the flanking gene or fragment thereof located 3' to the gene breakpoint, which primers are directed to DNA regions which are located 5' to one or more of the reverse primers of step (i) and which primers are optionally operably linked at their 5' end to an oligonucleotide tag;
  wherein the oligonucleotide tags of the forward primers are the same relative to the forward primer tags of step (iii)(a) and the oligonucleotide tags of the reverse primers are the same relative to the reverse primer tags of step (iii)(a) but which forward primer oligonucleotide tags are different relative to the reverse primer tags and which forward and reverse primer tags of step (iii) are different relative to the forward and reverse primer tags of step (i);
(iv) amplifying the DNA sample of step (iii);
(v) analysing said amplified DNA.

preferably, said gene breakpoint is a gene translocation breakpoint and still more preferably a chromosomal gene translocation breakpoint.

The primers which are used in the method of the present invention are of a relatively low individual concentration due to the starting primer pool comprising multiple individual primers. This reduces the risk of inducing inhibition of PCR. In order to facilitate a successful amplification result, it is therefore necessary to enable the generation of sufficient amplicons for detection and isolation. In one aspect of the present invention, this can be facilitated by tagging the primers with an oligonucleotide which can be used as a primer hybridisation site. In addition to the primers directed towards genes A and B, each PCR reaction may therefore also contain concentrations of two oligonucleotides which are directed to the tag, as a primer hybridisation site. These oligonucleotide sequences act as primers and enable efficient secondary amplification of the amplicons generated by the initial hybridisation and extension of the primers directed towards genes A and B. In one embodiment, the primer which is directed to the tag exhibits a $T_M$ of 65° C.-70° C. in order to minimise non-specific amplification. Thus these primers are directed towards overcoming the potential problem posed by the low concentrations of the primers directed towards A and B. Nevertheless, in some situations it may not be necessary to use one or both tag primers. For example, when there are only six forward primers for the BCR gene each primer may be at a concentration which is sufficient for relatively efficient amplification. Still further, it should be appreciated that the oligonucleotide tags provide an additional use when they are present in the final PCR round, since the tag primers can also be used for sequencing. Accordingly, although the tag is suitable for use as a site for primer hybridisation, it should be understood that the subject tag may also be useful for other purposes, such as a probe binding site in the context of Southern gel analysis or to enable isolation of the primer or the amplicon extended therefrom. To this end, the tag may comprise a non-nucleic acid component, such as a protein molecule or biotin which would enable isolation, for example by affinity chromatography, streptavidin binding or visualisation.

In order to ensure that these tags do not interfere with the extension of the primer, the primers are linked to the oligonucleotide tag at their 5' end. Reference to "oligonucleotide tag" should therefore be understood as a reference to a nucleotide sequence of less than 50 nucleotides which is linked to the 5' end of the forward and reverse primers of the present invention. In one embodiment, the tag is 25-30 bases in length. It should also be understood that consistently with the definitions provided in relation to the forward and reverse primers, the oligonucleotide tags herein described may also comprise non-nucleic acid components such as isolation or visualisation tags eg. biotin, enzymatic labels, fluorescent labels and the like. This enables quick and simple isolation or visualisation of the tagged primers or amplicons via non-molecular methods.

That the oligonucleotide tag is "operably linked" to the primer should be understood as a reference to those regions being linked such that the functional objectives of the tagged primer, as detailed hereinbefore, can be achieved. In terms of the means by which these regions are linked and, further, the means by which the subject oligonucleotide primer binds to its target DNA region, these correspond to various types of interactions. In this regard, reference to "interaction" should be understood as a reference to any form of interaction such as hybridisation between complementary nucleotide base pairs or some other form of interaction such as the formation of bonds between any nucleic or non-nucleic acid portion of the primer molecule or tag molecule with any other nucleic acid or non-nucleic acid molecule, such as the target molecule, a visualisation means, an isolation means or the like. This type of interaction may occur via the formation of bonds such as, but not limited to, covalent bonds, hydrogen bonds, van der Wals forces or any other mechanism of interaction. preferably, to the extent that the interaction occurs between the primer and a region of the target DNA, said interaction is hybridisation between complementary nucleotide base pairs. In order to facilitate this interaction, it is preferable that the target DNA is rendered partially or fully single stranded for a time and under conditions sufficient for hybridisation with the primer to occur.

Without limiting the present invention to any one theory or mode of action, the inclusion of an oligonucleotide tag which can itself function as a primer hybridisation site can assist in facilitating the convenient and specific amplification of the amplicon generated by the forward and reverse primers of the present invention. Accordingly, this overcomes somewhat the amplification limitation which is inherent where a relatively low starting concentration of the forward and reverse primers is used. Where the starting concentration of forward and reverse primers is sufficiently high, it may not be necessary to use a tag. Accordingly, in a preferred embodiment, the DNA sample of interest is contacted with both the forward and reverse primers of the present invention and primers directed to the oligonucleotide tags of the forward and reverse primers such that the amplification reaction of step (ii) proceeds in the context of all these primers. It should be understood, however, that although it is preferred that amplification based on both the gene primers and the tag primers is performed simultaneously, the method can be adapted to perform the tag primer based amplification step after the completion of the gene primer based amplification.

The DNA sequence of the tags may be the same or different. With respect to a first round amplification, the tags may be the same if the purpose is to amplify the initial amplification product. However, if one wishes to selectively enrich for amplicons containing the sequence of one of the flanking genes, the primer directed to the tag region of the primer of the gene of interest (eg. gene A) should differ to the primer directed to the tag region of the primer of the other gene (eg. gene B). In another example, in terms of a second or subsequent round of amplification, the tags which are used for sequencing would be required to be different to prevent the simultaneous sequencing of both strands.

The present invention therefore provides a method of identifying a gene translocation breakpoint, said method comprising:

(i) contacting a DNA sample with:
  (a) one to thirty forward primers directed to a DNA region of the antisense strand of the flanking gene or fragment thereof located 5' relative to the gene breakpoint, which primers are optionally operably linked at their 5' end to an oligonucleotide tag;
  (b) twenty-four to four hundred reverse primers directed to a DNA region of the flanking gene or fragment thereof located 3' relative to the gene breakpoint, which primers are optionally operably linked at their 5' end to an oligonucleotide tag;
  wherein the oligonucleotide tags of the forward primers are the same relative to the forward primer tags of step (a) and the oligonucleotide tags of the reverse primers are the same relative to the reverse primer tags of step (a) but which forward primer oligonucleotide tags are different relative to the reverse primer tags;
  (c) a primer directed to the forward primer oligonucleotide tag of step (i)(a); and
  (d) a primer directed to the reverse primer oligonucleotide tag of step (i)(b);
(ii) amplifying the DNA sample of step (i);
(iii) optionally contacting the amplicon generated in step (ii) with:
  (a) one to thirty forward primers directed to a DNA region of the flanking gene or fragment thereof located 5' relative to the gene breakpoint, which primers are directed to DNA regions which are located 3' to one or more of the forward primers of step (i) and which primers are optionally operably linked at their 5' end to an oligonucleotide tag;
  (b) twenty-four to four hundred reverse primers directed to a DNA region of the flanking gene or fragment thereof located 3' to the gene breakpoint, which primers are directed to DNA regions which are located 5' to one or more of the reverse primers of step (i) and which primers are optionally operably linked at their 5' end to an oligonucleotide tag;
  (c) a primer directed to the forward primer oligonucleotide tag of step (iii)(a); and
  (d) a primer directed to the reverse primer oligonucleotide tag of step (iii)(b);
  wherein the oligonucleotide tags of the forward primers are the same relative to the forward primer tags of step (iii)(a) and the oligonucleotide tags of the reverse primers are the same relative to the reverse primer tags of step (iii)(a) but which forward primer oligonucleotide tags are different relative to the reverse primer tags and which forward and reverse primer tags of step (iii) are different relative to the forward and reverse primer tags of step (i);
(iv) amplifying the DNA sample of step (iii);
(v) analysing said amplified DNA.

preferably said gene translocation breakpoint is a chromosomal gene translocation breakpoint.

It should be understood that the oligonucleotide primers and tags of the present invention should not be limited to the specific structure exemplified herein (being a linear, single-stranded molecule) but may extend to any suitable structural configuration which achieves the functional objectives detailed herein. For example, it may be desirable that all or part of the oligonucleotide is double stranded, comprises a looped region (such as a hairpin bend) or takes the form of an open circle confirmation, that is, where the nucleotide primer is substantially circular in shape but its terminal regions do not connect.

Facilitating the interaction of the nucleic acid primer with the target DNA may be performed by any suitable method. Those methods will be known to those skilled in the art.

Methods for achieving primer directed amplification are also very well known to those of skill in the art. In a preferred method, said amplification is polymerase chain reaction, NASBA or strand displacement amplification. Most preferably, said amplification is polymerase chain reaction. To this end, in one embodiment of the invention, a 20 minute hybridisation provides good amplification in the first round PCR.

Reference to a "sample" should be understood as a reference to either a biological or a non-biological sample. Examples of non-biological samples includes, for example, the nucleic acid products of synthetically produced nucleic acid populations. Reference to a "biological sample" should be understood as a reference to any sample of biological material derived from an animal, plant or microorganism (including cultures of microorganisms) such as, but not limited to, cellular material, blood, mucus, faeces, urine, tissue biopsy specimens, fluid which has been introduced into the body of an animal and subsequently removed (such as, for example, the saline solution extracted from the lung following lung lavage or the solution retrieved from an enema wash), plant material or plant propagation material such as seeds or flowers or a microorganism colony. The biological sample which is tested according to the method of the present invention may be tested directly or may require some form of treatment prior to testing. For example, a biopsy sample may require homogenisation prior to testing or it may require sectioning for in situ testing. Further, to the extent that the biological sample is not in liquid form, (if such form is required for testing) it may require the addition of a reagent, such as a buffer, to mobilise the sample.

To the extent that the target DNA is present in a biological sample, the biological sample may be directly tested or else all or some of the nucleic acid material present in the biological sample may be isolated prior to testing. It is within the scope of the present invention for the target nucleic acid molecule to be pre-treated prior to testing, for example inactivation of live virus or being run on a gel. It should also be understood that the biological sample may be freshly harvested or it may have been stored (for example by freezing) prior to testing or otherwise treated prior to testing (such as by undergoing culturing).

Reference to "contacting" the sample with the primer should be understood as a reference to facilitating the mixing of the primer with the sample such that interaction (for example, hybridisation) can occur. Means of achieving this objective would be well known to those of skill in the art.

The choice of what type of sample is most suitable for testing in accordance with the method disclosed herein will be dependent on the nature of the situation, such as the nature of the condition being monitored. For example, in a preferred embodiment a neoplastic condition is the subject of analysis. If the neoplastic condition is a lymphoid leukemia, a blood sample, lymph fluid sample or bone marrow aspirate would likely provide a suitable testing sample. Where the neoplastic condition is a lymphoma, a lymph node biopsy or a blood or marrow sample would likely provide a suitable source of tissue for testing. Consideration would also be required as to whether one is monitoring the original source of the neoplastic cells or whether the presence of metastases or other forms of spreading of the neoplasia from the point of origin is to be monitored. In this regard, it may be desirable to harvest and test a number of different samples from any one mammal. Choosing an appropriate sample for any given detection scenario would fall within the skills of the person of ordinary skill in the art.

The term "mammal" to the extent that it is used herein includes humans, primates, livestock animals (e.g. horses, cattle, sheep, pigs, donkeys), laboratory test animals (e.g. mice, rats, rabbits, guinea pigs), companion animals (eg. dogs, cats) and captive wild animals (eg. kangaroos, deer, foxes). preferably, the mammal is a human or a laboratory test animal. Even more preferably the mammal is a human.

As detailed hereinbefore, in one embodiment the method of the present invention is performed as a sequential two step amplification using multiple second round primers each of which is directed to a gene region which is either 3' (for the forward primers) or 5' (for the reverse primers) to that which is targeted by the corresponding first round primers. The person of skill in the art would appreciate that in some cases it may not be necessary to conduct a second round amplification. The necessity to perform a second round amplification may also be obviated if a selective or enrichment step as described below is performed. This situation may arise when the sequence around the breakpoint is amplified very efficiently and there is very little non-specific amplification such that a clearly defined band of amplification product is observed on electrophoresis of the product of the first round amplification or if the subsequent selection step is very efficient. In general, however, it is expected that a sequential two step amplification process would be used in order to minimise non-specific amplification and to generate a relatively short amplification product which spans the breakpoint region. In general, it is expected that the amplification product would be less than 1.5 kb, less than 1 kb, less than 0.8 kb or less than 0.5 kb. It should be understood that depending on the size of the genes which have been translocated, the method of the invention may be adapted to incorporate third or fourth round amplification steps in order to further minimise non-specific amplification. This can be an issue owing to the number of primers present in the multiplexed reaction and to the fact that one of the genes participating in the translocation often contains multiple repetitive sequences such as Alu. Nevertheless, it is expected that the need for further rounds of amplification would be unlikely.

Although the method of the present invention has been designed such that the amplification steps can be sequentially performed directly on the amplification product of a previous amplification, this should not be understood as a limitation in terms of whether any additional steps are sought to be incorporated by the skilled person, such as enrichment/selection steps. For example, one may seek to select for the desired amplicons after the first round amplification and to thereafter conduct the second round amplification on their material alone. Methods which one could utilise to select or enrich include:

(i) a selection step based on the unique oligonucleotide tags which are linked to the primers. Accordingly, since the tags themselves are also amplified and therefore form part of the amplicon, they could be used as a probe site to enable isolation of amplicons which are the result of both forward and reverse primer amplification and therefore should span the breakpoint. Alternatively, biotinylation of one of the tags provides means of identifying and isolating amplicons which have resulted from extension by either the forward or reverse primers. For example, by flooding the amplification product with biotinylated primer, the primer can act as a probe to identify the amplicons of interest and the biotinylation can provide a basis for isolating those amplicons. By ensuring that each of the primer groups of the present invention comprises a unique tag, it is possible to select out, with significant particularity, only specific amplicons of interest. In particular, the skilled person would seek to exclude amplicons which have been amplified by a forward primer but which have not then been amplified by a reverse primer, thereby indicating that the subject amplicon possibly does not extend across the breakpoint. By selecting out the amplicons which are most likely spanning the breakpoint, a subsequent round of amplification is more specifically targeted and less likely to generate unwanted amplicons as a result of either inherent cross-hybridisation of primers or the amplification of amplicons which do not flank both sides of the breakpoint.

(ii) One may seek to run the products on a gel and excise out only certain bands or regions which are likely to be relevant and thereafter subject these to a further amplification step. When a band is present on the gel after the second round amplification, if there are any problems in sequencing an attempt can be made to clean it up by cutting the product out of the gel and performing a series of PCR reactions using individual primers and/or smaller pools of primers. For example, one might use individual forward BCR primers and pools containing only 12 reverse ABL primers.

(iii) one may expose the amplified products to one or more rounds of bottleneck PCR in order to provide negative selection against non-specific amplified products.

Without limiting the application of the present invention to any one theory or mode of action, in a classical PCR, the primers and reaction conditions are designed so that primer hybridisation and extension of the forward and reverse primers occur at or close to the maximum efficiency so that the number of amplicons approximately doubles with each cycle resulting in efficient exponential amplification. Bottleneck PCR, however, is predicated on the use of forward and reverse primer sets where the primers of one set have been designed or are otherwise used under conditions wherein they do not hybridise and extend efficiently. Accordingly, although the efficient primer set will amplify normally, the inefficient set will not. As a consequence, when a sequence of interest is amplified, the number of amplicon strands is significantly less than that which would occur in a classical PCR. Efficient amplification only commences once amplicons have been generated which incorporate, at one end, the tag region of the inefficient primer. At this point, the primers directed to the tag regions effect a normal amplification rate. A "bottleneck" is therefore effectively created in terms of the generation of transcripts from the inefficient primer set.

A more severe bottleneck is usefully created where the inefficient primers are directed to commonly repeated sequences, such as an alu sequence. Amplification of unwanted product may result if such binding sites are closely apposed and if the inefficient primers can act as forward primers and reverse primers. However, owing to both primers being inefficient, amplification is initially extremely inefficient and there is a severe bottleneck. Efficient amplification only commences once amplicon strands have been generated which comprise the tag region of the inefficient primer at one end and its complement at the other. After any given number of cycles, the number of such amplicons is, however, substantially less than that which occurs during amplification of the sequence of interest. The amount of unwanted product at the end of the amplification reaction is correspondingly reduced.

Hybridisation and extension of an inefficient primer which has correctly hybridised to the sequence of interest followed in a subsequent cycle by hybridisation and extension of an efficient primer to the previously synthesised amplicon generates a template to which the tag primer can efficiently hybridise and extend. Since such molecules together with their complements provide upstream and downstream binding sites, each for an efficient primer (the tag primer and one member of the efficient set), succeeding cycles of amplification from such templates are both efficient and exponential. The result is that, after an initial lag or "bottleneck", the overall rate of amplification speeds up in later cycles so that a near doubling of amplicon number with each cycle results. However, the net result is that there is negative selection against amplification of undesired amplicons as compared to amplicons of the sequence of interest, owing to the bottleneck at each end for the former and only at one end for the latter.

Accordingly, if the same number of commencing target sequences is considered and comparison to the amplification produced by classical PCR is made, application of the bottleneck PCR will produce a lesser increase in the number of amplicons of the sequence of interest and an even lesser increase in the number of amplicons of unwanted sequences. Although amplification of both wanted and unwanted products occurs, there is relative enrichment of the sequence of interest relative to the unwanted sequences. There is an inverse relationship between absolute amplification and enrichment since decreasing the efficiency of the inefficient primer set produces increased enrichment at the expense of lesser amplification.

Once the amplification rounds have been completed, the amplicons spanning the breakpoint region can be analysed. In a preferred embodiment, the subject amplicon is isolated by excision of a gel band containing that amplicon and sequenced in order to characterise the breakpoint region. To the extent that a band excised from a gel is to be analysed, it may be necessary to further amplify the DNA contained therein in order to provide sufficient material for sequencing. The oligonucleotide tags hereinbefore described provide a suitable primer hybridisation site to facilitate further amplification of the isolated amplicons.

As detailed hereinbefore, the method of the present invention provides a simple and routine means of identifying and characterising any breakpoint region, such as the nature, accuracy and stability of a site directed insertion of a gene into a chromosome or vector (this being important in the context of gene therapy), but in particular the chromosomal gene translocation breakpoints that are characteristic of many diseases. Examples of such translocations and diseases include, but are not limited to:

t(2;5)(p23;q35)—anaplastic large cell lymphoma
t(8;14)—Burkitt's lymphoma (c-myc)
t(9;22)(q34;q11)—Philadelphia chromosome, CML, ALL (BCR-ABL recombination)
t(11;14)—Mantle cell lymphoma (Bcl-1)
t(11;22)(q24;q11.2-12)—Ewing's sarcoma
t(14;18)(q32;q21)—follicular lymphoma (Bcl-2)
t(17;22)—dermatofibrosarcoma protuberans
t(15;17)—acute promyelocytic leukemia (pml and retinoic acid receptor genes)
t(1;12)(q21;p13)—acute myelogenous leukemia
t(9;12)(p24;p13)—CML, ALL (TEL-JAK2)
t(X;18)(p11.2;q11.2)—Synovial sarcoma
t(1;11)(q42.1;q14.3)—Schizophrenia
t(1;19)—acute pre-B cell leukemia (PBX-1 and E2A genes).

preferably, said chromosomal gene translocation is a BCR-ABL translocation or a PML-RARalpha translocation.

According to this preferred embodiment there is provided a method of identifying a chromosomal BCR-ABL translocation breakpoint, said method comprising:

(i) contacting a DNA sample with:
   (a) one or more forward primers directed to a DNA region of BCR or fragment thereof, which primers are optionally operably linked at their 5' end to an oligonucleotide tag; and
   (b) one or more reverse primers directed to a DNA region of ABL or fragment thereof, which primers are optionally operably linked at their 5' end to an oligonucleotide tag;
   wherein the oligonucleotide tags of the forward primers are the same relative to the forward primer tags of step (a) and the oligonucleotide tags of the reverse primers are the same relative to the reverse primer tags of step (a) but which forward primer oligonucleotide tags are different relative to the reverse primer tags;
(ii) amplifying the DNA sample of step (i);
(iii) optionally contacting the amplicon generated in step (ii) with:
   (a) one or more forward primers directed to a DNA region of BCR or fragment thereof, which primers are directed to DNA regions which are located 3' to one or more of the forward primers of step (i) and which primers are optionally operably linked at their 5' end to an oligonucleotide tag; and
   (b) one or more reverse primers directed to ABL or fragment thereof, which primers are directed to DNA regions which are located 5' to one or more of the reverse primers of step (i) and which primers are optionally operably linked at their 5' end to an oligonucleotide tag;
   wherein the oligonucleotide tags of the forward primers are the same relative to the forward primer tags of step (iii)(a) and the oligonucleotide tags of the reverse primers are the same relative to the reverse primer tags of step (iii)(a) but which forward primer oligonucleotide tags are different relative to the reverse primer tags and which forward and reverse primer tags of step (iii) are different relative to the forward and reverse primer tags of step (i);
(iv) amplifying the DNA sample of step (iii);
(v) analysing said amplified DNA.

preferably, said amplification steps are performed using 1-30 forward primers and 24-300 reverse primers.

In terms of the embodiment of the invention exemplified herein, primers were chosen so that their binding sites were staggered with the separation between adjacent binding sites being approximately 500 bases. This was done so that the amplified material would have range in size, up to a maximum length of approximately 1 kilobase. This strategy may be contrasted to the prior art strategy of "Long PCR" which would require fewer primers and a less complex multiplex PCR reaction. One of the advantages of the strategy of the present invention is that the standard shorter PCR reaction is more robust and the amplified product can be sequenced immediately rather than requiring another set of PCR reactions to break it up into smaller amplicons which are suitable for sequencing.

The present invention therefore preferably provides a method of identifying a chromosomal BCR-ABL translocation breakpoint, said method comprising:
(i) contacting a DNA sample with:
   (a) one to thirty forward primers directed to a DNA region of BCR or fragment thereof, which primers are optionally operably linked at their 5' end to an oligonucleotide tag;
   (b) twenty-four to four hundred reverse primers directed to a DNA region of ABL or fragment thereof, which primers are optionally operably linked at their 5' end to an oligonucleotide tag;
   wherein the oligonucleotide tags of the forward primers are the same relative to the forward primer tags of step (a) and the oligonucleotide tags of the reverse primers are the same relative to the reverse primer tags of step (a) but which forward primer oligonucleotide tags are different relative to the reverse primer tags;
   (c) a primer directed to the forward primer oligonucleotide tag of step (i)(a); and
   (d) a primer directed to the reverse primer oligonucleotide tag of step (i)(b);
(ii) amplifying the DNA sample of step (i);
(iii) contacting the amplicon generated in step (ii) with:
   (a) one to thirty forward primers directed to a DNA region of BCR or fragment thereof, which primers are directed to DNA regions which are located 3' to one or more of the forward primers of step (i) and which primers are optionally operably linked at their 5' end to an oligonucleotide tag;
   (b) twenty-four to four hundred reverse primers directed to a DNA region of ABL or fragment thereof, which primers are directed to DNA regions which are located 5' to one or more of the reverse primers of step (i) and which primers are optionally operably linked at their 5' end to an oligonucleotide tag;
   (c) a primer directed to the forward primer oligonucleotide tag of step (iii)(a); and
   (d) a primer directed to the reverse primer oligonucleotide tag of step (iii)(b);
   wherein the oligonucleotide tags of the forward primers are the same relative to the forward primer tags of step (iii)(a) and the oligonucleotide tags of the reverse primers are the same relative to the reverse primer tags of step (iii)(a) but which forward primer oligonucleotide tags are different relative to the reverse primer tags and which forward and reverse primer tags of step (iii) are different relative to the forward and reverse primer tags of step (i);
(iv) amplifying the DNA sample of step (iii);
(v) isolating and sequencing said amplified DNA.

More preferably, said DNA sequence is a blood derived sample.

The method of the present invention has broad application including, but not limited to:
(i) enabling the design and generation of patient specific probes which can be used for the ongoing monitoring of a patient who is diagnosed with a disease condition characterised by chromosomal gene translocation. Results obtained by this means for chronic myeloid leukemia are shown in FIG. 6.
(ii) the analysis and monitoring of in vitro and in vivo gene transfection systems which are directed to integrating a gene or other DNA region into a chromosome, vector, plasmid, artificial chromosome or the like. Where the general site at which recombination should occur is known, the present invention can be applied to determine the specific point and nature of the integration (i.e. the breakpoint). It can also be used to monitor the ongoing stability of the genetic recombination event by virtue of enabling the generation of specific primers.

Accordingly, in yet another aspect there is provided a method of monitoring a disease condition in a mammal, which disease condition is characterised by a gene breakpoint, said method comprising screening for the presence of said breakpoint in a biological sample derived from said mammal, which breakpoint has been identified in accordance with the method hereinbefore defined.

Methods of screening for the subject breakpoint would be well known to those skilled in the art and include any suitable probe-based screening technique, such as PCR based methods. By virtue of the identification of the breakpoint region in accordance with the method of the invention, one can design an appropriate probe set to specifically amplify the subject breakpoint.

In one embodiment, said gene breakpoint is a chromosomal gene translocation breakpoint such as:
t(2;5)(p23;q35)
t(8;14)
t(9;22)(q34;q11)
t(11;14)
t(11;22)(q24;q11.2-12)
t(14;18)(q32;q21)
t(17;22)
t(15;17)
t(1;12)(q21;p3)
t(9;12)(p24;p13)
t(X;18)(p11.2;q11.2)
t(1;11)(q42.1;q14.3)
t(1;19).

In another embodiment, said condition is:
anaplastic large cell lymphoma
Burkitt's lymphoma
CML, ALL
Mantle cell lymphoma
Ewing's sarcoma
follicular lymphoma
dermatofibrosarcoma protuberans
acute promyelocytic leukemia
acute myelogenous leukemia
Synovial sarcoma
Schizophrenia; or
acute pre-B cell leukemia.

Still another aspect of the present invention is directed to a DNA primer set, which primer set is designed to amplify and/or otherwise detect a gene breakpoint, which breakpoint has been identified in accordance with the method hereinbefore defined.

The present invention is now described by reference to the following non-limiting examples and figures.

Example 1

Isolation of BCR/ABL Breakpoint Product from gDNA of Patient 1

Genomic DNA extracted by Qiagen Flexigene kit
$1^{st}$ Round PCR (50 ng genomic DNA)—all reactions performed in duplicate
Forward primer pool—FA (Contains 7 forward BCR primers BCRF1-BCRF7 each with same 5' tag sequence (A), Total 50 ng (7.14 ng each)
Reverse primer pool—R3/4 (Pool of 24 oligonucleotide reverse ABL primers, each with same 5' tag sequence (C), Total 50 ng (2.08 ng each)
Forward and reverse tag sequence primers (A,C)—25 ng of each
PCR Conditions
1×PCR buffer, 5 mM MgCl$_2$, 0.75 ul dUTP (300 uM each), 0.4 ul Platinum Taq (2 U)
Cycling Conditions
95/4 min
(97° C./1 min, 65° C./20 min, 72° C./1 min)×5
(96° C./30 sec, 65° C./20 min, 72° C./1 min)×5
(92° C./30 sec, 65° C./20 min, 72° C./1 min)×10
$2^{nd}$ Round PCR ($1^{st}$ round reaction diluted 1/200 in sterile water)
Forward primer pool—NFA (Contains 7 forward internal BCR primers BFN1-BFN7 each with same 5' tag sequence (B), Total 50 ng (7.14 ng each)
Reverse primer pool—RN3/4 (Pool of 24 oligonucleotide reverse internal ABL primers, each with same 5' tag sequence (D), Total 50 ng (2.08 ng each)
Forward and reverse tags (B,D)-25 ng of each
PCR Conditions
1×PCR buffer, 5 mM MgCl$_2$, 0.75 ul dUTP (300 uM), 0.4 ul Pt Taq (2 U)
Cycling Conditions
95/4 min
(94° C./30 sec, 65° C./10 min, 72° C./1 min)×10
(94° C./30 sec, 65° C./5 min, 72° C./1 min)×15
PCR products (7 ul) resolved on 1.5% (v/v) agarose gel at 120 volts
Identification of BCR/ABL Breakpoint from Patient 1
PCR products resolved on 1.5% (v/v) agarose gel at 120 volt
Band excised and purified via Flexigene kit
Reamplification of bands by PCR (1/1000 dilution of purified product)
Forward primer—Tag B (25 ng)
Reverse primer—TagD (25 ng)
PCR Conditions
1×PCR buffer, 5 mM MgCl$_2$, 0.75 ul dUTP (300 uM), 0.4 ul Pt Taq (2 U)
Cycling Conditions
95/4 min
(94° C./30 sec, 65° C./30 sec, 72° C./30 sec)×35
PCR Product Sequenced with TagB Primer (Flinders Sequencing Facility)
Confirmation of Breakpoint by PCR
PCR performed on gDNA (50 ng) across breakpoint
Patient 1 gDNA vs 10× Normal gDNA (several primer combinations)
Forward primer—BCR (patient specific) (25 ng)
Reverse primer—ABL (patient specific) (25 ng)
PCR Conditions
1×PCR buffer, 5 mM MgCl$_2$, 0.75 ul dUTP (300 uM), 0.4 ul Pt Taq (2 U)
Cycling Conditions
95/4 min
(97° C./1 min, 65° C./30 sec, 72° C./30 sec)×5
(96° C./30 sec, 65° C./30 sec, 72° C./30 sec)×5
(92° C./30 sec, 65° C./30 sec, 72° C./30 sec)×25
PCR products resolved on 3% (v/v) agarose gel at 120 volt
Band excised and purified via Qiagen minElute kit
Products sequenced with 5' BCR specific primer to confirm BCR/ABL breakpoint (Flinders sequencing facility).

Nearly all translocations involve a 3 kb region of the BCR gene and 140 kb region of the ABL gene. Six forward primers used to cover the region of the BCR gene and 282 primers used to cover the region of the ABL gene. Six PCRs are set up, each containing one of the BCR primers, all of the ABL primers, and the common tag primer.

If necessary, a second round of PCR is performed with a nested internal BCR primer and 282 nested internal ABL primers Alternatively, 1-3 rounds of Bottleneck PCR are performed in order to remove non-specific amplified products and reveal the amplified translocation sequence.

The ABL gene is very rich in Alu sequences, and the BCR gene also contains one such sequence. The ABL primers have therefore undergone a selection procedure which sequentially involves, for each ABL primer:
  design using standard criteria
  pairing with each BCR primer and testing by electronic PCR for amplification off the BCR template. Primers that fail this criterion are discarded.
  incorporation in a pool of 12 or 24 ABL primers, pairing the pool with each BCR primer, and testing by experimental PCR using a BCR template which has been previously produced by PCR amplification. Any pool that produces amplification and thus fails this test is further analysed by testing each of the individual ABL primers to determine which is responsible for amplification. When identified, this primer is discarded.

The BCR and ABL primers used in Example 1 are shown in Example 2.

Example 2

Primers Used for Isolation of BCR-ABL Translocation Breakpoint in Chronic Myeloid Leukemia BCR Primers

```
1st Rd
BCRF1-FT0            cttctccctgacatccgtgg
BCRF2-FT0 (-5)       acacagcatacgctatgcacatgtg
BCRF3-FT0            gaggttgttcagatgaccacgg
BCRF4-FT1 (-10)      cagctactggagctgtcagaacag
BCRF5-FT0            tgggcctccctgcatcc
BCRF6-FT0            tccccctgcacccacg 2nd Rd
BCRF1-FT1            tgacatccgtggagctgcagatgc
BCRF2-FT1            acatgtgtccacacacaccccacc
BCRF3-FT1            accacgggacacctttgaccctgg
BCRF4-FT1 (-4)       ctggagctgtcagaacagtgaagg
BCRF5-FT1            tccctgcatccctgcatctcctcc
BCRF6-FT1            cccacgacttctccagcactgagc
```

The second round primers were internal to the first round primers and were used either for a second round together with internal ABL primers or for performing Bottleneck PCR in order to eliminate non-specific amplified material and facilitate isolation of the translocation breakpoint.

Various combinations of the forward and reverse primers can be used. In one embodiment, the protocol that was used was to set up 6 PCRs, each containing a different BCR primer and all 282 ABL primers
282 Reverse ABL Primers Used for the First PCR Round and the Tag Sequence which was on the 5' End of Each Primer

```
Tag A    gcaacactgtgacgtactggagg
R1       gtctatctaaaattcacaaggaatgc
R2       aggcaaagtaaaatccaagcaccc
```

-continued

```
R3       cactcctgcactccagcctgg
R4       caaccaccaaagtgcttttcctgg
R5       atatggcatctgtaaatattaccacc
R6       tgcctcggcctcccaaagtgc
R7       agccaccacacccagccagg
R8       aataactgttttctcccccaaaac
R9       tgttttacaaaaatggggccatacc
R10      acttaagcaaattctttcataaaaggg
R11      ctttcaattgttgtaccaactctcc
R12      acctcctgcatctctccttttgc
R13      aaataaagttttgagaaccataagtgg
R14      caccatcacagctcactgcagc
R15      aacctctttgagaatcggatagcc
R16      aaataaagtacatacctccaattttgc
R17      gacacattcctatgggtttaattcc
R18      tgtaaaatatggtttcagaagggagg
R19      gcaggtggataacgaggtcagg
R20      ccagccaagaatttcaaagattagc
R21      gaagggagatgacaaagggaacg
R22      gcagaagaactgcttgaacctgg
R23      gtggtcccagctactcgagagg
R24      ccctcagcaaaactaactgaaaagg
R25      tagaaaccaagatatctagaattccc
R26      ccacgcccggcggaataaatgc
R27      acaaaaaaagaggcaaaaactgagag
R28      ctgggcgcagtggctcatgcc
R29      tggctgtgaggctgagaactgc
R30      ctgggcgacagagtgagactcc
R31      aagtctggctgggcgcagtgg
R32      aatggacaaaagaggtgaactggc
R33      gatagagtgaaaacgcacaatggc
R34      aattaaacagctaggtcaatatgagg
R35      ggtctccactatcaagggacaag
R36      aagcagctgttagtcatttccagg
R37      aggcatcctcagattatggctcc
R38      cctgagtaacactgagaccctgc
R39      aacactcaagctgtcaagagacac
R40      attcaggccaggcgcagtggc
R41      taaatcgtaaaactgccacaaagc
R42      cagaggagtaggagaaggaaaagg
```

| | |
|---|---|
| R43 | ggtagctatctaccaagtagaatcc |
| R44 | atcagattggaaaaagtcccaaagc |
| R45 | ctcctgaaaagcacctactcagc |
| R46 | ctccttaaacctgaggtactggg |
| R47 | tttctcctaatagaccaccattcc |
| R48 | ctgctgtattaccatcactcatgtc |
| R49 | ctggccaacatagtgaaaccacg |
| R50 | atttgaatagggttaaagtatcattg |
| R51 | cacttcagtggaagttggcatgc |
| R52 | gttttcttcgaagtgataaacatacg |
| R53 | gctccttagtctatgtacctgtgg |
| R54 | tactctggcatggtaactggtgc |
| R55 | acaaaggactaggtctgtgggagc |
| R56 | ccaagtttaccaaattaccaaagttacc |
| R57 | tgagccgatatcacgccactgc |
| R58 | tcccaataaaggttttggcccagg |
| R59 | ctgggtagcaaattagggaacagg |
| R60 | ctggccagaaaagacagttttatcc |
| R61 | ggttcccaggaagggataacacc |
| R62 | tcactccaggaggttccatttcc |
| R63 | aggcttggaaataagcagcagtgg |
| R64 | attcatacaatggaatactactcagc |
| R65 | taagtgatcctcccacctcaacc |
| R66 | tataagaggaagactggggctgg |
| R67 | tcatacttatgcaggttataggagg |
| R68 | caagatcacgccactgcactcc |
| R69 | aaaataaatagctggtgctcaagatc |
| R70 | caccagcctcattcaacagatgg |
| R71 | caatgcagcctcaacctcctgg |
| R72 | gttaggtcaggtgctcatgtctg |
| R73 | aagtttcaaaaggacatgtacaaaatg |
| R74 | tcctgaagaggctgcagcttcc |
| R75 | ctggtgcacattcccaagtgtgc |
| R76 | catgttggccatgttcttctgagg |
| R77 | ctcagcctcccgagtagctgg |
| R78 | aaagacatttaagaggagatgaggc |
| R79 | tgctgggattacaggcgtgagc |
| R80 | tgtgacttccatccgcagctcc |
| R81 | gacacttttgtggagcttcatgg |
| R82 | catgtgaggggcacgtcttgc |
| R83 | tcttctctatgagaaaagtggttgc |
| R84 | tggcaaaatgctatcgagctgcc |
| R85 | tatgaacacagccggcctcagg |
| R86 | gaggttgcagtgagctgagatcg |
| R87 | gtcaagcacccagtccgatacc |
| R88 | atctgggcttggtggcgcacg |
| R89 | gttaagcgggtcccacatcagc |
| R90 | cagccagtttcagtagaaagatgc |
| R91 | gacccaagcataaggggactagc |
| R92 | cccaaaaagtttacaagagaaattttc |
| R93 | cgcctgtagtcccagctactcg |
| R94 | cgcgtgatgcggaaaagaaatcc |
| R95 | tctactatgaaccctccttcagac |
| R96 | gtgctgggattacaggtgtgagc |
| R97 | ttatccaaatgtcccagggcagg |
| R98 | ctgccagcactgctcgccagc |
| R99 | gctactgcaggcagtgccttcc |
| R100 | catccaagcccaaggtgtcagg |
| R101 | tgtttgcatgtaatttcaggaagcc |
| R102 | gatccgtcactgttaacactcagg |
| R103 | ctcacagtcacaagctcctgagc |
| R104 | gagatgatgctggggtcacagg |
| R105 | ttagaagaatgggatcgcaaagg |
| R106 | cggtattcaaatatgaggtcaggc |
| R107 | gtaaatcctgctgccagtcttcc |
| R108 | acagggtcagacagagccttgg |
| R109 | agttattgatctaactatacaacaagc |
| R110 | aaagactaggggccggggacg |
| R111 | ctggtagaaataaagacaacaaagcc |
| R112 | gtgccaagtaattaaaagtttgaaacc |
| R113 | ggcttttgaagggagcaccacc |
| R114 | gaaggataaatacctatgatactttcc |
| R115 | ggcagggaaatactgtgcttcaag |
| R116 | gtggtgaaattccacctcagtacc |
| R117 | tcccaaagtgctgggattacagg |
| R118 | gaaattagcaaacaatgccaagacg |
| R119 | taagtattggaccgggaaggagg |
| R120 | ctatcattttgctcaaagtgtagcc |
| R121 | atttcacaaactacagaggccagg |
| R122 | tagacttctgtctctctatgctgc |
| R123 | tgagtgagctgccatgtgataccc |

| | |
|---|---|
| R124 | acttcacaccagcctgtccacc |
| R125 | taactcatatcctcagagaccc |
| R126 | agaggttcctcgattcccctgc |
| R127 | gtgtcagcgtcccaacacaaagc |
| R128 | gaaagtggatgggcaagcattgc |
| R129 | gtgatcacctcacagctgcagg |
| R130 | gtttgtttagtcaaggcatttcacc |
| R131 | cctcagcctccagagtagctgg |
| R132 | taaaagaaaactcctccttcctgg |
| R133 | aatgtgctatgtctttaaatccatgg |
| R134 | agctggcaaatctggtaatataaaag |
| R135 | gcttgaacctggaaggtggagg |
| R136 | gcaggcatgctaagaccttcagc |
| R137 | cagctccatgaataactccacagg |
| R138 | gcttgaacccaggaggcagagg |
| R139 | atcgaagatgccactgcaagagg |
| R140 | ccaaccacacttcaggggatacc |
| R141 | cacgccagtccactgatactcac |
| R142 | gggtttcaccatgttggccagg |
| R143 | cccaacaaaggctctggcctgg |
| R144 | atgacagcagaggagcttcatcc |
| R145 | gcaggctacgagtaaaaggatgg |
| R146 | cgggtaaaatcttgcctccttcc |
| R147 | aaacttaaaccaatggtggatgtgg |
| R148 | agagactgaggaactgttccagc |
| R149 | gaaacggtcttggatcactgatcc |
| R150 | tgcgcatgatatcttgtttcaggg |
| R151 | ggcctccgtttaaactgttgtgc |
| R152 | gaatgctggcccgacacagtgg |
| R153 | tcttggtatagaaaagccagctgg |
| R154 | gcaaaagcccaagagcccctgg |
| R155 | ttctcccaaaatgagccccaagg |
| R156 | gtggtgacgtaaacaaaaggtacc |
| R157 | gcaaattccatgtgaatcttattggc |
| R158 | cctgatctatggaacagtggtgg |
| R159 | gttacaaacgttgcagtttgcaacg |
| R160 | gaaccccgtcaacagtgatcacc |
| R161 | acaggacctcaaggcaaggagc |
| R162 | catacctaaaatagaaatgtctatccc |
| R163 | gagttgcatatatgttttataaatccc |
| R164 | tgagcccacatccataaagttagc |
| R165 | accgcaacctttgccgcctgg |
| R166 | taaatattttgtatggagtcaccacc |
| R167 | aaagccaggagaaaaagttatgagg |
| R168 | tcccaaagtcccaggattacagg |
| R169 | tcactatggagcatctccgatgg |
| R170 | agttccctggaagtctccgagg |
| R171 | aaaataatcacccagcccacatcc |
| R172 | acaaaactacagacacagaaagtgg |
| R173 | tttgggaggctgaggtaggtgg |
| R174 | aaagacagtgaaacatctataaggg |
| R175 | cattttgggagaccagggcagg |
| R176 | gcatgggacagacacaaagcagc |
| R177 | gaataacaaagagagccggctgg |
| R178 | taaaccttttattgaaaattgtcaaatgg |
| R179 | cgcctcagcctcccaaagtgc |
| R180 | tacattagtttttataggtccagtagg |
| R181 | gaaggtttattcatattaaaatgtgcc |
| R182 | ctggcttctgtggtttgagttgg |
| R183 | acagacctacctcctaaggatgg |
| R184 | gctagcttttgtgtgtaagaatggg |
| R185 | ggcctactcacacaatagaatacc |
| R186 | gcaccattgcactccagcctgg |
| R187 | gaaattaggataaaggttgtcacagc |
| R188 | cagaagtgttcaaggtgaaactgtc |
| R189 | ctgaatcatgaaatgttctactctgc |
| R190 | tgtcaacttgactgggccatacg |
| R191 | ctcccgtatagttgggattatagg |
| R192 | gcttggagttccttgaaattcttgg |
| R193 | cctggtggctccagttttctacc |
| R194 | aactcctgacctcatgatccacc |
| R195 | gctgggattacaggcatgagcc |
| R196 | ttctcctttatccttggtgacattc |
| R197 | tcccaaagtgctgggattacagg |
| R198 | gtcataagtcagggaccatctgc |
| R199 | ctgtttcattgatttccagactggc |
| R200 | gcaatctcggctcactgcaagc |
| R201 | gaagaagtgactatatcagatctgg |
| R202 | ttcaccatgttggccaggctgg |
| R203 | catcactgaagatgacaactgagc |
| R204 | gtccagcctgggcgatagagc |

| | |
|---|---|
| R205 | gaggaaagtctttgaagaggaacc |
| R206 | ggtacactcaccagcagttttgc |
| R207 | gagcaactggtgtgaatacatatgg |
| R208 | caatacctggcaccacatacacc |
| R209 | gggactacaggcatgtgccacc |
| R210 | cggtggctcacgcgtgtaatcc |
| R211 | caactgttaaatctctcatggaaacc |
| R212 | gacaaaggattagaaatgcaccc |
| R213 | ggaaatgttctaaaactggattgtgg |
| R214 | aataataatagccaggtgtggtagc |
| R215 | ctggaacactcacacattgctgg |
| R216 | ctgggtgacagagcgagactcc |
| R217 | cccaaatcatcccgtgaaacatgc |
| R218 | gaccctgcaatcccaacactgg |
| R219 | ctctcaggccttcaaactacacc |
| R220 | caggaaagggctcgctcagtgg |
| R221 | atctgcaaaagcagcagagcagg |
| R222 | gtacccatgacagacaagttttagg |
| R223 | cttatcccctactgtctcctttgg |
| R224 | ggatggtctcgatctcctgacc |
| R225 | aggttagagaccttcctctaatgc |
| R226 | agctgggattacaggtgcctgc |
| R227 | gctgaggcaggttggggctgc |
| R228 | acatttaacgtctcctaacttctcc |
| R229 | gtgctgcgattacaggtgtgagc |
| R230 | tatgacagcagtattatactatcacc |
| R231 | ctggggaccaaatctgaactgcc |
| R232 | gtagctattgttatttccaaaagagg |
| R233 | gcttgggaccccaggacaagg |
| R234 | cctggccaacatggggaaatcc |
| R235 | aattgcttgaacctgggaggtgg |
| R236 | gcctaagacccaaaagctattagc |
| R237 | catattaaagggccatattcaaattgg |
| R238 | ggatgtaaccagtgtatatcacagg |
| R239 | ggaagtttagtccacatcttctagc |
| R240 | gcacccacaggacaaccacacg |
| R241 | gggacgcgcctgttaacaaagg |
| R242 | gggctgggggccacgctcc |
| R243 | cgcaaaagtgaagccctcctgg |
| R244 | gaaatcctacttgatctaaagtgagc |
| R245 | tttgagcaacttggaaaaaataagcg |
| R246 | ttcccaaaagacaaatagcacttcc |
| R247 | ccattttgaaaatcacagtgaattcc |
| R248 | gaaaagaaaaccctgaattcaaaagg |
| R249 | tgctgaaaagaagcatttaaaagtgg |
| R250 | ctcttaccagtttcagagctttcc |
| R251 | ttttcagccaaaaatcaaggacagg |
| R252 | cttgagcccaggagtttgagacc |
| R253 | cgcctgtagtaccctctactagg |
| R254 | ggtaaagaaagaaggatttgaaaacc |
| R255 | taagagtaatgaggttaaagtttatgc |
| R256 | cattttattgtcacaggccatttgc |
| R257 | gccacgccttctcttctgccacc |
| R258 | tgcctctcctgactgcactgtg |
| R259 | ccatgctctaccacgcccttgg |
| R260 | cattcaggctggagtgcggtgg |
| R261 | cttaaaaattgtctggctaagacattg |
| R262 | ttgctcttgttgcccgggttgg |
| R263 | gagcttagaggaaaagtattatttcc |
| R264 | tggtgctgtgccagacgctgg |
| R265 | cagatcttttggctattgtcttgg |
| R266 | gaaggaaagggcctcccactgc |
| R267 | catgaaaagcatgctggggagg |
| R268 | caaacataaaaaagctttaatagaagcc |
| R269 | tcccaactatgaaaaaatagaagacg |
| R270 | cacaaattagccgggcatggtgg |
| R271 | cttcctttactgagtctttctaaagc |
| R272 | tgtcctttgaaatgtaggtatgtgg |
| R273 | ggatcttgcaatactgacatctcc |
| R274 | atttgaaaagaactgaaggatctacc |
| R275 | gtgagctgagatctcgtctctgc |
| R276 | tttgtctgaaacagattctaaaagttgg |
| R277 | gcaggtgcctgtagtcccagc |
| R278 | gtttgagcttctaaaattcatggattc |
| R279 | gtggtaggtcaaaccgcaattcc |
| R280 | accaaatcagacatatcagctttgg |
| R281 | cacagaacggatcctcaataaagg |
| R282 | gttaactcctcccttctctttatgg |

282 Reverse ABL Primers Used for the Second PCR Round and the Tag Sequence which was on the 5' End of Each Primer

| | | |
|---|---|---|
| 2nd Round Tag D | gtgttcagagagcttgatttccagg | |
| RN1 | cccacttgattttttcccacatgg | |
| RN2 | atttatttagatgaagtgaatattttcc | |
| RN3 | atttagtttgtttaactgtgagtgc | |
| RN4 | gtacagaagtgcttgatgcatacc | |
| RN5 | aggcagataaaaattctccattagc | |
| RN6 | acaagcacgagccacagcacc | |
| RN7 | cgctcttgttgcccaggctgg | |
| RN8 | cccaaaacagactttctagataacc | |
| RN9 | ttcaaattgcttttttttctactcacc | |
| RN10 | gatctgaaaaagtgacaggttgg | |
| RN11 | cactgaaatttgaaaggaacatatgg | |
| RN12 | tctggtgcagtggcctctagg | |
| RN13 | accataagtggttttacctgatgg | |
| RN14 | cccaggcgcaggtgattctcc | |
| RN15 | ggtggctcacgcctgaaatcc | |
| RN16 | cacagtccacgtgccacaatcc | |
| RN17 | aatcatgttaacacatccctctcc | |
| RN18 | gaagagagtgttgaaaggttaagc | |
| RN19 | cgagaccatactggctaagatgg | |
| RN20 | attagccacacaataaatgttctgg | |
| RN21 | tttgaaaagcgttgcaatatgatgc | |
| RN22 | ggttgcagtgagccgagatcg | |
| RN23 | ggtgggaggactgcctgagc | |
| RN24 | aacagagagaaaaaacacaaattacc | |
| RN25 | gatatctagaattcccaaatacttgg | |
| RN26 | gtgatagaattaaaggaaaaaataaacg | |
| RN27 | attgttccttttctaaatattctacc | |
| RN28 | cagcactttgggaggctgagg | |
| RN29 | cacagaggtttcacagtgctgg | |
| RN30 | aacttctgcttctgtccataatgc | |
| RN31 | gcctgtaatcccagcactttgg | |
| RN32 | gccagtaaacatatgaaaaggtgc | |
| RN33 | aattatgtaaataaagagtgaaaagg | |
| RN34 | cccctacacagaaaaaacaattcc | |
| RN35 | tgagtgtcaaagaaaaatacaattgg | |
| RN36 | atacacagagaaaatgagtccacc | |
| RN37 | aacactccccttctctgtttagc | |
| RN38 | gatattctttgcaacctaggatgc | |
| RN39 | ctctaaaactaatcagcaatgtaacc | |
| RN40 | cacctgtaatcccagcactttgg | |
| RN41 | cgtaaaactgccacaaagcttgtagg | |
| RN42 | gtggcagaggtgcaagcaagc | |
| RN43 | acagaaatgacaaacgcatgtacc | |
| RN44 | acactctcttagctaggctttgg | |
| RN45 | gagcttggaatagggcagttcc | |
| RN46 | ctgggttctttaaacatgtccagg | |
| RN47 | tcaagaaaggacactgcagtggc | |
| RN48 | catgcacacaaactatctcattcc | |
| RN49 | tagccgggcatggtggcacg | |
| RN50 | atcatgctgattgaatttcaaatagc | |
| RN51 | ttggcatgcagggcagtgacc | |
| RN52 | ggtggtgagataataacacctgc | |
| RN53 | ttgctatataataatcatttgtgatcc | |
| RN54 | cggtaactgttactctgggatgg | |
| RN55 | aggctaggttcccttctcttcc | |
| RN56 | gtagtgcctagcacagagaaagc | |
| RN57 | ctagcctgggcaacaagagcg | |
| RN58 | tctctctcctctctgggatcag | |
| RN59 | gtttgaatatttgtatgcagcaagc | |
| RN60 | tagaacaaattctggcttataaaagc | |
| RN61 | ccactctacctttattccttgcc | |
| RN62 | agaccagaatatgcaagcagagg | |
| RN63 | ggacgttttgctggtgtctgcg | |
| RN64 | aaggaacaaactgttgtcacatgc | |
| RN65 | atgtagctgggactacaggtgc | |
| RN66 | ggctcatgcctgtaatcccagc | |
| RN67 | atgaggttttcacacaaaaagatgc | |
| RN68 | tgggcgacagagcaagactcc | |
| RN69 | aaatgtccctaaaagtgatcaacagc | |
| RN70 | cagactcagttttacctcatcagc | |
| RN71 | agtgatctttcctctttaacctcc | |
| RN72 | ccagctattcaggaggccaagg | |
| RN73 | cttaaacattatgacactgtcttgc | |
| RN74 | ccaggtctatgaggccgttcc | |
| RN75 | tccaaagcatccctacattatacc | |
| RN76 | acatacatatgcagtgactagc | |
| RN77 | tacaggtgccagccaccatgc | |
| RN78 | gcctgtaatcccagcactctgg | |

-continued

| | |
|---|---|
| RN79 | gacagagtcccactcttgttgc |
| RN80 | gtgccttccaaagcagtgtagg |
| RN81 | tatcttactgggtatgtataatgcc |
| RN82 | caaaggaaatacgtcctaccagg |
| RN83 | cctttctcacagacatgcttcc |
| RN84 | taaacacagtgagcagaatccc |
| RN85 | ataaagcaaacttctaaaagggtcc |
| RN86 | accactacactccagcctggg |
| RN87 | gatacctgggtcagagtaagtgc |
| RN88 | tgtaatctcagctacttgggagg |
| RN89 | gtgtcgtcttctcttcctctacg |
| RN90 | ctggctagtatgaggttggtgc |
| RN91 | ggactagccacatttcaaccagg |
| RN92 | gcagtatactgagaatttagtttcc |
| RN93 | gaggctgaggcaggagaatgg |
| RN94 | cattgtttgatgaaggtcaacagc |
| RN95 | cagacaagagtggctacggcag |
| RN96 | acgcccagccagattattcagg |
| RN97 | ggaaccagaaagaagtgcaaagg |
| RN98 | tgagccatcttggaggcaggc |
| RN99 | caggaccttcctacaaacctcc |
| RN100 | aacacaacatatctgaccttacgc |
| RN101 | gccttagaagtccagaggaaagc |
| RN102 | tgacgtacccagtagaccttcc |
| RN103 | ctctgcaagcctgggaaacagg |
| RN104 | gccttgtccccaagtcctaagg |
| RN105 | gcaaagggactcctggaattcc |
| RN106 | gctcctgcctgtaatcccagc |
| RN107 | gaaggaaacagaaaaagcagaggc |
| RN108 | cttactaccgttcttcttcactgg |
| RN109 | actattctgtttctttaggtttactgc |
| RN110 | cggtggctcacacctgtaatcc |
| RN111 | agccagagttctgtgctctagg |
| RN112 | taatttgcatttcgtgccgctcc |
| RN113 | cacttttaatacagatcccaatagg |
| RN114 | atgtatttttctttcctgtcaagc |
| RN115 | aaatgttaacattattctccctaagg |
| RN116 | catatgcccagatcccgtctcc |
| RN117 | acaggtgtgagccgctgcacc |
| RN118 | gccaagacgtttacagttttggc |
| RN119 | aggaaacttctgaggatgatggg |
| RN120 | gctttatagggcagtctgaattcc |
| RN121 | ttagaataaaagttatctcgggagg |
| RN122 | taatttcttcagctttatccctcag |
| RN123 | cacatgactaattctctattcattcc |
| RN124 | aaagacctcaagaaaagagtcacc |
| RN125 | gacccataaagattatatgcccag |
| RN126 | aaagtactaatgcagtgtgtcagc |
| RN127 | gaggttcctcgattcccctgc |
| RN128 | ggagagcagaggaattcacagg |
| RN129 | agtaattagaaactgattctaagacg |
| RN130 | cataccattgccaatccagttcc |
| RN131 | attacgggtgcctgccactgc |
| RN132 | cagccaggcagaggagagagg |
| RN133 | ttttcattccaagtttctgtttggg |
| RN134 | tttcaaataggaatttggataatccc |
| RN135 | taagccgagatcacaccactgc |
| RN136 | ccttcagcgcattatatcttggc |
| RN137 | ccatctaatccatcttaaattcacc |
| RN138 | gagtggagactgcgccactgc |
| RN139 | aatcatgtgccaattaaaccatggc |
| RN140 | cccagggaccagaccagacc |
| RN141 | ctcactcaccagtgaaaatcagc |
| RN142 | ggttgctctcgaactcctgacc |
| RN143 | gttcccccagctcctttctgc |
| RN144 | agaaagatgtagaagggtccagc |
| RN145 | gggaaaggtgtattatgcaagcg |
| RN146 | ctctctcagacctaatgcaaaagc |
| RN147 | aactatacatacagtatttgtattagc |
| RN148 | aaattaatgcaatccatgatccagg |
| RN149 | ctttctccactctaagagaaccc |
| RN150 | ttttggtgtgttcatattggctgc |
| RN151 | gcttccacaaatgacagacaaagg |
| RN152 | ggctcatgcttgtaatcccagc |
| RN153 | catatgaattgttgttcctttgtagg |
| RN154 | cactggtacaagtccaagagtcc |
| RN155 | gaccctgtgtctacttcctggg |
| RN156 | tatttgaactatctcttgaaatgtcc |
| RN157 | ctgattaaaaagtattacccttgc |
| RN158 | tttgaaactgcactcaataacttgg |
| RN159 | agtaatgtgtcatgatccaatggc |

| | |
|---|---|
| RN169 | gaaagcatttcccaatgtctcacc |
| RN161 | caatggacaaaaggcccaactgc |
| RN162 | tccagctctggcttttttgttaag |
| RN163 | acggagtctcactccgtgacc |
| RN164 | ctatgtcatagtcaagagactttgc |
| RN165 | gttcaagcgattctcctgtctcg |
| RN166 | ccacctaatacttaaatacggaagc |
| RN167 | atattcaacaaacttaatagtgaagtg |
| RN168 | ttacaggcgtgagtcaccatgc |
| RN169 | aacacctccaagaggccaaacg |
| RN170 | tactattggcaaatttcaattatatgg |
| RN171 | agcccacatcctaaaattcaataag |
| RN172 | gaaagtggataagtgtttgtctgg |
| RN173 | ggccaggcattcaagaccagc |
| RN174 | agccaacaacaaaaagacacaacc |
| RN175 | ttgagcccaggagttcaagacc |
| RN176 | cagactaaagatctcagagagaaac |
| RN177 | cgcttgtaatcccagcacttgg |
| RN178 | aaaagtgaaatcagaatttgtttcc |
| RN179 | caggcgtgagcaactgtgtcc |
| RN180 | ggtccagtaggatctcgtttgc |
| RN181 | actttgaaaatgttgttatagctggg |
| RN182 | ttccctgcatctaagtcttctcc |
| RN183 | agatatctaccattgaagagtttgc |
| RN184 | agtcttcacttcactttgttgtcc |
| RN185 | ccatgcaggtatgaaatataaaagc |
| RN186 | tgggtgacagagtgagactcc |
| RN187 | acagcaataccgggttaacatgc |
| RN188 | tttatgtaaaagatgaatgcgaggc |
| RN189 | ctactctgctactgggaacagg |
| RN190 | caaacgttagtctggcaaaatgcg |
| RN191 | tgcacgctaccacacccagc |
| RN192 | aattcttggatctgtgtgtttactgc |
| RN193 | taccagttatcattctctttctgc |
| RN194 | atccacccacctcggcctcc |
| RN195 | cactctgcctggcccttaatgg |
| RN196 | atagtttgttaatatgccactaagg |
| RN197 | gcgtgagccaccgcacctgg |
| RN198 | ctccatcacacaaattttatgtggc |
| RN199 | agacggagtctcgttctgtcgc |
| RN200 | tcccaggttcaagccattctcc |
| RN201 | tattttgagagtctcactctgtcg |
| RN202 | gtctcgaactcctgacctcagg |
| RN203 | aaggaggtgaagagtgaactacg |
| RN204 | gtctcaggttttggacttacttgg |
| RN205 | tttacagatcttaaatgcattaggac |
| RN206 | gtacactgaacaaaggagacagg |
| RN207 | ctggtagtaatgcaaaatagcacc |
| RN208 | catttaatgtgaaatgaattataagcc |
| RN209 | gagacagggtttcactatgttgg |
| RN210 | ccagcactttggaaggctgagg |
| RN211 | gaaaccaagtatcatggtaaattgc |
| RN212 | cagtgagggctgctcagttcc |
| RN213 | gccaggtgcggtggctcacg |
| RN214 | catgcctgtaatcccagctacc |
| RN215 | atgtaaatggtacagtcactttagg |
| RN216 | cccacaatacagagaactcttacc |
| RN217 | tgaaacatgcagcccagtgtcc |
| RN218 | tgttttttctcctgccttcaatcc |
| RN219 | gctttcctgggtctccatctgg |
| RN220 | gcagccgcttgaaaacaaaacagc |
| RN221 | gatcacgttacatttgggggtgg |
| RN222 | taggctgaaaaactaaaatttgttgc |
| RN223 | ctcctttgggctcctttagtcc |
| RN224 | gcctcggcctcccaaagtgc |
| RN225 | aatgcctagagagatttggcagg |
| RN226 | gagatggggtttcactatgttgg |
| RN227 | tgtgatcttgccactgcactcc |
| RN228 | acttctcctccattgtttcttcg |
| RN229 | cgtgcccgggctcagttctac |
| RN230 | ccaaaacaataaaatcacaatttggg |
| RN231 | ctgaactgccttagagtaaatccg |
| RN232 | atttctgtatcaggtctgtgttcc |
| RN233 | ggctgaccccttcactgtttcc |
| RN234 | caaaaattagccaggcatggtgg |
| RN235 | gcagtgagcagtgatcgcacc |
| RN236 | aaagactgtgaactaacttgtttgc |
| RN237'1 | tgccaagaattacacattattaggc |
| RN238 | ggccaggatgtcattaactttcc |
| RN239 | gtaagagctgacgtgtattgtgc |
| RN240 | cccggtgaggccgcacatcc |

-continued

| | |
|---|---|
| RN241 | cctgcgccttaacccctcc |
| RN242 | cggcgcctaggggccatcg |
| RN243 | acttaaggaaacgaacatgacacc |
| RN244 | gagaccgagtcttgctgtgtcg |
| RN245 | gtattaattgaagatgatttggaatgc |
| RN246 | tcttaaaagactatcgctgaggc |
| RN247 | aaaagagacatcagtagagcatcc |
| RN248 | gttcatgttttctttgacgtctcc |
| RN249 | tttcgaaagttcaggctgagtgc |
| RN250 | gaccctcaaaacaatcctctaagg |
| RN251 | caaaacacacttagaaacaaactgc |
| RN252 | gcctgggcgacatagtgagacc |
| RN253 | ggcaggagaatggcgtgaacc |
| RN254 | tttgctcgttgcccaggctgg |
| RN255 | gcaacttaatgtgatagaataatagc |
| RN256 | cctccccttctgctgccagc |
| RN257 | ccacaacaatgtaaactcctctgg |
| RN258 | tactctccctagagttcgttccc |
| RN259 | gggtcccctttggccattcc |
| RN260 | gatcttggctcacttcaacctcc |
| RN261 | aggggaaatatttaaaccttgg |
| RN262 | aatgcaatggtgcatttacagagg |
| RN263 | tcattttatctatttctacatggtcc |
| RN264 | ggaagggaaatgcccatgaacc |
| RN265 | agtgaacattttctgcagcctcc |
| RN266 | caacaggacgtcaggcgatcc |
| RN267 | ccttcaggctgtcctgaaaagg |
| RN268 | agtctcactccatcgcccagg |
| RN269 | actgtgaacagtagttaactcagg |
| RN270 | gcatgcctgtaatccaagctgc |
| RN271 | gaaacaattctcttttcacacttgc |
| RN272 | ggctcatgcctgttatcccagc |
| RN273 | agaagaagcttagtcatatgtttgg |
| RN274 | cagatgcttgagccaaacaaatgg |
| RN275 | ctggcagacagagtgagactcc |
| RN276 | aatgtgtgaatattattcattacaggg |
| RN277 | gcaggagaattgcttgaacctgg |
| RN278 | ctttagtcaaattaaaacagtctatcc |
| RN279 | gatttctatctcctgcaaccacc |
| RN280 | ttcttgtgtaactactaaaaatctcc |
| RN281 | aaagggtcttcataaggctaatgg |
| RN282 | ctcttaaggattatttatatgaagacc |

Example 3

Identification of the PML-RARalpha Breakpoint

Amplified patient DNA was electrophoresed on a 2% agarose gel. P is patient DNA, N is the normal DNA and W is the water control. The patient DNA was amplified using multiple RARα primers and a single PML primer a) Amplified patient DNA electrophoresed on a 2% agarose gel, P is patient DNA, N is the normal DNA and W is the water control. The patient DNA was amplified for one round using an RARα primer and a PML primer designed using the breakpoint sequence.

b) The sequence chromatogram obtained from the patient DNA. The breakpoint between PML and RARα is shown.

Isolation of the PML-RARalpha Breakpoint in Acute Promyelocytic Leukemia

Two patients have been studied and the breakpoint has been isolated and sequenced in both. The primers used are shown in Example 4.

Example 4

Primers Used for Isolation of PML-RARalpha Translocation Breakpoint in Acute Promyelocytic Leukemia PML Forward Primers

| 1st Rd | |
|---|---|
| PML F1-FT1 | caggaggagccccagagc |
| PML F2-FT1 | tcctggggatggttggatgc |
| PML F3-FT1 | tgacccacagagtttacacagc |
| PML F4-FT1 | agtcagggcaggctctgcc |
| PML F5-FT1 | tattttggcccatccagaaagc |
| PML F6-FT1 | cacccagagtacagctttgttcc |
| 2nd Rd | |
| PML F1-FT2 | gaggagccccagagcctgc |
| PML F2-FT2 | tggggatggttggatgcttacc |
| PML F3-FT2 | cccacagagtttacacagcttgc |
| PML F4-FT2 | caggctctgcccactcacc |
| PML F5-FT2 | ccatccagaaagcccaaagcc |
| PML F6-FT2 | ccagagtacagctttgttcctcattc |

The second round primers were internal to the first round primers and were used for performing Bottleneck PCR in order to eliminate non-specific amplified material and facilitate isolation of the translocation breakpoint.

Various combinations of the forward and reverse primers can be used. 2 exemplary protocols were either to set up 6 PCRs, each containing a different PML primer and all 34 RARalpha primers, or to set up 1 PCR which contained all 6 forward and all 34 reverse primers.

34 Reverse RARalpha Reverse Primers Used for the First PCR Round and the Tag Sequence which was on the 5' End of Each Primer

| | |
|---|---|
| Tag R1 | gcagtacaaacaacgcacagcg |
| RAR1 | ctgccaccctccacagtccc |
| RAR2 | gccaagaccatgcatgcg |
| RAR3 | cccagggacaaagagactccc |
| RAR4 | caggaagcagacagtcttctagttcc |
| RAR5 | tgcctgtaatcccaacactttgg |
| RAR6 | tccctctggccaggatggg |
| RAR7 | atggggaatgggagtaggaagc |
| RAR8 | cagatcagttctcccctccagc |
| RAR9 | acaaaaaagaaacatgctcagagagg |
| RAR10 | tggtggcatgcatctgtagtcc |
| RAR11 | aggtgctctatagatgttagcatccc |
| RAR12 | ccaggacaggatggagatctgg |
| RAR13 | agggaacctgtgcattatccttgc |
| RAR14 | cagaagtcttgctttaaggaggagg |
| RAR15 | gggtacgtgaaactcaccaagg |
| RAR16 | cagagtgtggcaagcaaggg |
| RAR17 | aacattttaaaggtacaaataacgtggg |
| RAR18 | tagggagcaacagccattaagc |
| RAR19 | ggtgcactgtccagctctgg |
| RAR20 | actctcgctgaactcgcctgg |
| RAR21 | ctcggtctctggtggtacgc |
| RAR22 | gcaagaggtccgagctggg |
| RAR23 | ggaagaagtgaaacaagagatgaagg |
| RAR24 | cccagagaacaaaccggattagg |
| RAR25 | cccttcaaccttctccaatctgc |
| RAR26 | cccatgtccagtggtttaggg |
| RAR27 | gagattggtgggagacagatgg |
| RAR28 | cttctcagctcaaagttccagcg |
| RAR29 | gaatgggagagatgaccagagg |
| RAR30 | aagggcaaggggggtatgtgg |
| RAR31 | ggaaggaagcatgggaacacc |
| RAR32 | ccatcaatgctctgtctgtctgg |
| RAR33 | gtgccgtgactgtgcttgg |
| RAR34 | acatcccattgacctcatcaagc |

Nearly all translocations involve a 3 kb region of the BCR gene and 140 kb region of the ABL gene. Six forward primers used to cover the region of the BCR gene and 282 primers used to cover the region of the ABL gene. Six PCRs are set up, each containing one of the BCR primers, all of the ABL primers, and the common tag primer.

If necessary, a second round of PCR is performed with a nested internal BCR primer and 282 nested internal ABL primers Alternatively, 1-3 rounds of Bottleneck PCR are performed in order to remove non-specific amplified products and reveal the amplified translocation sequence.

The ABL gene is very rich in Alu sequences, and the BCR gene also contains one such sequence. The ABL primers have therefore undergone a selection procedure which sequentially involves, for each ABL primer:

design using standard criteria pairing with each BCR primer and testing by electronic PCR for amplification off the BCR template. Primers that fail this criterion are discarded.

incorporation in a pool of 12 or 24 ABL primers, pairing the pool with each BCR primer, and testing by experimental PCR using a BCR template which has been previously produced by PCR amplification. Any pool that that produces amplification and thus fails this test is further analysed by testing each of the individual ABL primers to determine which is responsible for amplification. When identified, this primer is discarded.

The BCR and ABL primers used in Example 1 are shown in Example 2.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

| Sequence Identifier | Sequence |
|---|---|
| SEQ ID NO:001 | gtgggccccccgtttccgtgtacagggcac ctgcagggagggcaggcagctagcctgaagg ctgatccccccttcctgttagcacttttgat gggactagtggactttggttcagaaggaaga gctatgcttgtttagggcctcttgtctcctcc caggagtggacaaggtgggttaggagcagtt tctccctgagtggctgc |
| SEQ ID NO:002 | caccacgtctggctaattttgtattttag tagagatggggtttcaacatgttagccaggc tggtctcgaactcctgacctcaggtgatcca cccgcctgggccctccaaagtgctgggatta caggcaggagccactgtgcccggcctgacct catatttgaataccgagttttagttctggag gagctgcaggttttatgaaaagggaacacat ttgattcctcagagcagccacaggccagctc tctgaagtaaagtgcacgtgtgcatgtgtgt gcacactcacacacacgtacacacacattca caaataactgtgcccggcctgacctcatatt tgaataccgagttttagttctggaggagctg cagg |
| SEQ ID NO:003 | tttgggaggctgaggcaggtggatcgcttga gctcaggagttggagaccagcctgaccaaca tggtgaaaccctgtgtctactaaaaatacaa agattagccgggctaggcagtgggcacctgt aatcacaactgcttgggaggctgagggaaga gaatcgcttgaacccaggaggcggaggttgc agtgagccgagcttgtgccactgcattccag cctgggcgacagag |

TABLE 1-continued

| Sequence Identifier | Sequence |
|---|---|
| SEQ ID NO:004 | ggtctcactctgttgaactcctggtggcctc aagggatcctcctacctcggcctcacaaagt attggaattacaggtgtgagtcactgcagct ggccttcacttatcactgtgaggagtaaaca gctgcatggtgggcttaatgccatctaacac gagtgactccatgttcagacagtaggatcac aaatgattattatatagcaatgaatggccac aggtacatagactaaggagccacatccctgc t |
| SEQ ID NO:005 | cctccagctacctgccagccggcacttttgg tcaagctgttttgcattcactgttgcacata tgctcagtcacacacacagcatacgctatgc acatgtgtccacacacaccccacccacatcc cacatcaccccgaccccctctgctgtccttg gaaccttattacacttcgagtcactggtttg cctgtattgtgaaaccagctggatcc |
| SEQ ID NO:006 | ttatttataacaacattttcagcgtggcaac tgcagtttcagaatggtggaattataccagt cagagagagatgcaaatgatttaaaatagga agaaagcaggtgtctggcccagaggaccaga ttaagaagacccccatgagagttacaatagtt agtgaaaatggtgcttctgcaaacctcatgt ctacagaagctggt |
| SEQ ID NO:007 | tgcaccttcataacataatctttctcctggg cccctgtctctggctgcctcataaacgctgg tgtttccctcgtgggcctccctgcatccctg catctcctcccgggtcctgtctgtgagcaat acagcgtgacacccacgctgccccgtggtc ccggggcttgtctctccttgcctccctgttac ctttcttcctatctcttccttgccccg |
| SEQ ID NO:008 | gtgagctccgcctcctgtcagatcagtggcg gcattagtttctcataggagcatgaaatcta ttgtgaacagtacatgcgatggatccaggtt gcgtgctcctagtgagaatctaatgcctgag gatctctcattgtctcttatcactcccagat aggactgtctagttgcaggaaaacaagctca gggctcccactgattctacattacagtgggt tgtataattattatatattacaatgtaataa taa |
| SEQ ID NO:009 | ggagtctgaggaggggaaggaggcaaggttg gctcggatcccagccagtaagtctgggtgtg g |
| SEQ ID NO:010 | cttctccctgacatccgtgg |
| SEQ ID NO:011 | acacagcatacgctatgcacatgtg |
| SEQ ID NO:012 | gaggttgttcagatgaccacgg |
| SEQ ID NO:013 | cagctactgagctgtcagaacag |
| SEQ ID NO:014 | tgggcctccctgcatcc |
| SEQ ID NO:015 | tccccctgcaccccacg |
| SEQ ID NO:016 | tgacatccgtgggagctgcagatgc |
| SEQ ID NO:017 | acatgtgtccacacacaccccacc |
| SEQ ID NO:018 | accacgggacacctttgaccctgg |
| SEQ ID NO:019 | ctggagctgtcagaacagtgaagg |
| SEQ ID NO:020 | tccctgcatccctgcatctcctcc |
| SEQ ID NO:021 | cccacgacttctccagcactgagc |
| SEQ ID NO:022 | gcaacactgtgacgtactggagg |
| SEQ ID NO:023 | gtctatctaaaattcacaaggaatgc |
| SEQ ID NO:024 | aggcaaagtaaaatccaagcaccc |
| SEQ ID NO:025 | cactcctgcactccagcctgg |
| SEQ ID NO:026 | caaccaccaaagtgcttttcctgg |
| SEQ ID NO:027 | atatggcatctgtaaatattaccacc |
| SEQ ID NO:028 | tgcctcggcctcccaaagtgc |
| SEQ ID NO:029 | agccaccacacccagccagg |
| SEQ ID NO:030 | aataactgttttctccccccaaaac |
| SEQ ID NO:031 | tgttttacaaaaatggggccatacc |
| SEQ ID NO:032 | acttaagcaaattctttcataaaaggg |
| SEQ ID NO:033 | cttcaattgttgtaccaactctcc |
| SEQ ID NO:034 | acctcctgcatctctccttttgc |
| SEQ ID NO:035 | aaataaagttttgagaaccataagtgg |
| SEQ ID NO:036 | caccatcacagctcactgcagc |
| SEQ ID NO:037 | aacctctttgagaatcggatagcc |
| SEQ ID NO:038 | aaataaagtacatacctccaattttgc |
| SEQ ID NO:039 | gacacattcctatgggtttaattcc |
| SEQ ID NO:040 | tgtaaaatatggtttcagaagggagg |
| SEQ ID NO:041 | gcaggtggataacgaggtcagg |
| SEQ ID NO:042 | ccagccaagaatttcaaagattagc |
| SEQ ID NO:043 | gaagggagatgacaaagggaacg |
| SEQ ID NO:044 | gcagaagaactgcttgaacctgg |
| SEQ ID NO:045 | gtggtcccagctactcgagagg |
| SEQ ID NO:046 | ccctcagcaaaactaactgaaaagg |
| SEQ ID NO:047 | tagaaaccaagatatctagaattccc |
| SEQ ID NO:048 | ccacgcccggcggaataaatgc |
| SEQ ID NO:049 | acaaaaaaagaggcaaaaactgagag |
| SEQ ID NO:050 | ctgggcgcagtggctcatgcc |
| SEQ ID NO:051 | tggctgtgaggctgagaactgc |
| SEQ ID NO:052 | ctgggcgacagagtgagactcc |
| SEQ ID NO:053 | aagtctggctgggcgcagtgg |
| SEQ ID NO:054 | aatggcaaaagaggtgaactggc |
| SEQ ID NO:055 | gatagagtgaaaacgcacaatggc |
| SEQ ID NO:056 | aattaaacagctaggtcaatatgagg |
| SEQ ID NO:057 | ggtctccactatcaagggacaag |
| SEQ ID NO:058 | aagcagctgttagtcatttccagg |
| SEQ ID NO:059 | aggcatcctcagattatggctcc |
| SEQ ID NO:060 | cctgagtaacactgagaccctgc |
| SEQ ID NO:061 | aacactcaagctgtcaagagacac |
| SEQ ID NO:062 | attcaggccaggcgcagtggc |
| SEQ ID NO:063 | taaatcgtaaaactgccacaaagc |

TABLE 1-continued

| Sequence Identifier | Sequence |
|---|---|
| SEQ ID NO:064 | cagaggagtaggagaaggaaaagg |
| SEQ ID NO:065 | ggtagctatctaccaagtagaatcc |
| SEQ ID NO:066 | atcagattggaaaaagtcccaaagc |
| SEQ ID NO:067 | ctcctgaaaagcacctactcagc |
| SEQ ID NO:068 | ctccttaaacctgaggtactggg |
| SEQ ID NO:069 | ttttctcctaatagaccaccattcc |
| SEQ ID NO:070 | ctgctgtattaccatcactcatgtc |
| SEQ ID NO:071 | ctggccaacatagtgaaaccacg |
| SEQ ID NO:072 | atttgaataggggttaaagtatcattg |
| SEQ ID NO:073 | cacttcagtggaagttggcatgc |
| SEQ ID NO:074 | gtttttcttcgaagtgataaacatacg |
| SEQ ID NO:075 | gctccttagtctatgtacctgtgg |
| SEQ ID NO:076 | tactctggcatggtaactggtgc |
| SEQ ID NO:077 | acaaaggactaggtctgtggagc |
| SEQ ID NO:078 | ccaagtttaccaaattaccaaagttacc |
| SEQ ID NO:079 | tgagccgatatcacgccactgc |
| SEQ ID NO:080 | tcccaataaaggttttggcccagg |
| SEQ ID NO:081 | ctgggtagcaaattagggaacagg |
| SEQ ID NO:082 | ctggccagaaaagacagttttatcc |
| SEQ ID NO:083 | ggttcccaggaagggataacacc |
| SEQ ID NO:084 | tcactccaggaggttccatttcc |
| SEQ ID NO:085 | aggcttggaaataagcagcagtgg |
| SEQ ID NO:086 | attcatacaatggaatactactcagc |
| SEQ ID NO:087 | taagtgatcctcccacctcaacc |
| SEQ ID NO:088 | tataagaggaagactggggctgg |
| SEQ ID NO:089 | tcatacttatgcaggttataggagg |
| SEQ ID NO:090 | caagatcacgccactgcactcc |
| SEQ ID NO:091 | aaaataaatagctggtgctcaagatc |
| SEQ ID NO:092 | caccagcctcattcaacagatgg |
| SEQ ID NO:093 | caatgcagcctcaacctcctgg |
| SEQ ID NO:094 | gttaggtcaggtgctcatgtctg |
| SEQ ID NO:095 | aagtttcaaaaggacatgtacaaaatg |
| SEQ ID NO:096 | tcctgaagaggctgcagcttcc |
| SEQ ID NO:097 | ctggtgcacattccaagtgtgc |
| SEQ ID NO:098 | catgttggccatgttcttctgagg |
| SEQ ID NO:099 | ctcagcctcccgagtagctgg |
| SEQ ID NO:100 | aaagacatttaagaggagatgaggc |
| SEQ ID NO:101 | tgctgggattacaggcgtgagc |
| SEQ ID NO:102 | tgtgacttccatccgcagctcc |
| SEQ ID NO:103 | gacactttgtggagctttcatgg |
| SEQ ID NO:104 | catgtgaggggcacgtcttgc |
| SEQ ID NO:105 | tcttctctatgagaaaagtggttgc |
| SEQ ID NO:106 | tggcaaaatgctatcgagctgcc |
| SEQ ID NO:107 | tatgaacacagccggcctcagg |
| SEQ ID NO:108 | gaggttgcagtgagctgagatcg |
| SEQ ID NO:109 | gtcaagcacccagtccgatacc |
| SEQ ID NO:110 | atctgggcttggtggcgcacg |
| SEQ ID NO:111 | gttaagcgggtcccacatcagc |
| SEQ ID NO:112 | cagccagtttcagtagaaagatgc |
| SEQ ID NO:113 | gacccaagcataaggggactagc |
| SEQ ID NO:114 | cccaaaaagtttacaagagaaattttc |
| SEQ ID NO:115 | cgcctgtagtcccagctactcg |
| SEQ ID NO:116 | cgcgtgatgcggaaaagaaatcc |
| SEQ ID NO:117 | tctactatgaaccctccttcagac |
| SEQ ID NO:118 | gtgctgggattacaggtgtgagc |
| SEQ ID NO:119 | ttatccaaatgtcccagggcagg |
| SEQ ID NO:120 | ctgccagcactgctcgccagc |
| SEQ ID NO:121 | gctactgcaggcagtgccttcc |
| SEQ ID NO:122 | catccaagcccaaggtgtcagg |
| SEQ ID NO:123 | tgtttgcatgtaatttcaggaagcc |
| SEQ ID NO:124 | gatccgtcactgttaacactcagg |
| SEQ ID NO:125 | ctcacagtcacaagctcctgagc |
| SEQ ID NO:126 | gagatgatgctggggtcacagg |
| SEQ ID NO:127 | ttagaagaatgggatcgcaaagg |
| SEQ ID NO:128 | cggtattcaaatatgaggtcaggc |
| SEQ ID NO:129 | gtaaatcctgctgccagtcttcc |
| SEQ ID NO:130 | acagggtcagacagagccttgg |
| SEQ ID NO:131 | agttattgatctaactatacaacaagc |
| SEQ ID NO:132 | aaagactagggggccggggacg |
| SEQ ID NO:133 | ctggtagaaataaagacaacaaagcc |
| SEQ ID NO:134 | gtgccaagtaattaaaagtttgaaacc |
| SEQ ID NO:135 | ggcttttgaagggagcaccacc |
| SEQ ID NO:136 | gaaggataaatacctatgatactttcc |
| SEQ ID NO:137 | ggcagggaaatactgtgcttcaag |
| SEQ ID NO:138 | gtggtgaaattccacctcagtacc |
| SEQ ID NO:139 | tcccaaagtgctgggattacagg |
| SEQ ID NO:140 | gaaattagcaaacaatgccaagacg |
| SEQ ID NO:141 | taagtattggaccgggaaggagg |

TABLE 1-continued

| Sequence Identifier | Sequence |
| --- | --- |
| SEQ ID NO:142 | ctatcattttgctcaaagtgtagcc |
| SEQ ID NO:143 | atttcacaaactacagaggccagg |
| SEQ ID NO:144 | tagacttctgtctctctatgctgc |
| SEQ ID NO:145 | tgagtgagctgccatgtgatacc |
| SEQ ID NO:146 | acttcacaccagcctgtccacc |
| SEQ ID NO:147 | taactcatatcctcagagagaccc |
| SEQ ID NO:148 | agaggttcctcgattcccctgc |
| SEQ ID NO:149 | gtgtcagcgtcccaacacaaagc |
| SEQ ID NO:150 | gaaagtggatgggcaagcattgc |
| SEQ ID NO:151 | gtgatcacctcacagctgcagg |
| SEQ ID NO:152 | gtttgtttagtcaaggcatttcacc |
| SEQ ID NO:153 | cctcagcctccagagtagctgg |
| SEQ ID NO:154 | taaaagaaaactcctccttcctgg |
| SEQ ID NO:155 | aatgtgctatgtctttaaatccatgg |
| SEQ ID NO:156 | agctggcaaatctggtaatataaaag |
| SEQ ID NO:157 | gcttgaacctggaaggtggagg |
| SEQ ID NO:158 | gcaggcatgctaagaccttcagc |
| SEQ ID NO:159 | cagctccatgaataactccacagg |
| SEQ ID NO:160 | gcttgaaccaggaggcagagg |
| SEQ ID NO:161 | atcgaagatgccactgcaagagg |
| SEQ ID NO:162 | ccaaccacacttcaggggatacc |
| SEQ ID NO:163 | cacgccagtccactgatactcac |
| SEQ ID NO:164 | gggtttcaccatgttggccagg |
| SEQ ID NO:165 | cccaacaaaggctctggcctgg |
| SEQ ID NO:166 | atgacagcagaggagcttcatcc |
| SEQ ID NO:167 | gcaggctacgagtaaaaggatgg |
| SEQ ID NO:168 | cgggtaaaatcttgcctccttcc |
| SEQ ID NO:169 | aaacttaaaccaatggtggatgtgg |
| SEQ ID NO:170 | agagactgaggaactgttccagc |
| SEQ ID NO:171 | gaaacggtcttggatcactgatcc |
| SEQ ID NO:172 | tgcgcatgatatcttgtttcaggg |
| SEQ ID NO:173 | ggcctccgtttaaactgttgtgc |
| SEQ ID NO:174 | gaatgctggcccgacacagtgg |
| SEQ ID NO:175 | tcttggtatagaaaagccagctgg |
| SEQ ID NO:176 | gcaaaagcccaagagcccctgg |
| SEQ ID NO:177 | ttctcccaaaatgagcccaagg |
| SEQ ID NO:178 | gtggtgacgtaaacaaaaggtacc |
| SEQ ID NO:179 | gcaaattccatgtgaatctattggc |
| SEQ ID NO:180 | cctgatctatggaacagtggtgg |
| SEQ ID NO:181 | gttacaaacgttgcagtttgcaacg |
| SEQ ID NO:182 | gaaccccgtcaacagtgatcacc |
| SEQ ID NO:183 | acaggacctcaaggcaaggagc |
| SEQ ID NO:184 | catacctaaaatagaaatgtctatccc |
| SEQ ID NO:185 | gagttgcatatatgttttataaatccc |
| SEQ ID NO:186 | tgagcccacatccataaagttagc |
| SEQ ID NO:187 | accgcaacctttgccgcctgg |
| SEQ ID NO:188 | taaatattttgtatggagtcaccacc |
| SEQ ID NO:189 | aaagccaggagaaaaagttatgagg |
| SEQ ID NO:190 | tcccaaagtcccaggattacagg |
| SEQ ID NO:191 | tcactatggagcatctccgatgg |
| SEQ ID NO:192 | agttccctggaagtctccgagg |
| SEQ ID NO:193 | aaaataatcacccagcccacatcc |
| SEQ ID NO:194 | acaaaactacagacacagaaagtgg |
| SEQ ID NO:195 | tttgggaggctgaggtaggtgg |
| SEQ ID NO:196 | aaagacagtgaaacatctataaggg |
| SEQ ID NO:197 | cattttgggagaccagggcagg |
| SEQ ID NO:198 | gcatgggacagacacaaagcagc |
| SEQ ID NO:199 | gaataacaaagagagccggctgg |
| SEQ ID NO:200 | taaacctttattgaaaattgtcaaatgg |
| SEQ ID NO:201 | cgcctcagcctcccaaagtgc |
| SEQ ID NO:202 | tacattagttttataggtccagtagg |
| SEQ ID NO:203 | gaaggtttattcatattaaaatgtgcc |
| SEQ ID NO:204 | ctggcttctgtggtttgagttgg |
| SEQ ID NO:205 | acagacctacctcctaaggatgg |
| SEQ ID NO:206 | gctagttttgtgtgtaagaatggg |
| SEQ ID NO:207 | ggcctactcacacaatagaatacc |
| SEQ ID NO:208 | gcaccattgcactccagcctgg |
| SEQ ID NO:209 | gaaattaggataaaggttgtcacagc |
| SEQ ID NO:210 | cagaagtgttcaaggtgaaactgtc |
| SEQ ID NO:211 | ctgaatcatgaaatgttctactctgc |
| SEQ ID NO:212 | tgtcaacttgactgggccatacg |
| SEQ ID NO:213 | ctcccgtatagttgggattatagg |
| SEQ ID NO:214 | gcttggagttccttgaaattcttgg |
| SEQ ID NO:215 | cctggtggctccagttttctacc |
| SEQ ID NO:216 | aactcctgacctcatgatccacc |
| SEQ ID NO:217 | gctgggattacaggcatgagcc |
| SEQ ID NO:218 | ttctcctttatccttggtgacattc |
| SEQ ID NO:219 | tcccaaagtgctgggattacagg |

TABLE 1-continued

| Sequence Identifier | Sequence |
|---|---|
| SEQ ID NO:220 | gtcataagtcagggaccatctgc |
| SEQ ID NO:221 | ctgtttcattgatttccagactggc |
| SEQ ID NO:222 | gcaatctcggctcactgcaagc |
| SEQ ID NO:223 | gaagaagtgactatatcagatctgg |
| SEQ ID NO:224 | ttcaccatgttggccaggctgg |
| SEQ ID NO:225 | catcactgaagatgacaactgagc |
| SEQ ID NO:226 | gtccagcctgggcgatagagc |
| SEQ ID NO:227 | gaggaaagtctttgaagaggaacc |
| SEQ ID NO:228 | ggtacactcaccagcagttttgc |
| SEQ ID NO:229 | gagcaactggtgtgaatacatatgg |
| SEQ ID NO:230 | caatacctggcaccacatacacc |
| SEQ ID NO:231 | gggactacaggcatgtgccacc |
| SEQ ID NO:232 | cggtggctcacgcgtgtaatcc |
| SEQ ID NO:233 | caactgttaaatctctcatggaaacc |
| SEQ ID NO:234 | gacaaaggattagaaatgcaccc |
| SEQ ID NO:235 | ggaaatgttctaaaactggattgtgg |
| SEQ ID NO:236 | aataataatagccaggtgtggtagc |
| SEQ ID NO:237 | ctggaacactcacacattgctgg |
| SEQ ID NO:238 | ctgggtgacagagcgagactcc |
| SEQ ID NO:239 | cccaaatcatccccgtgaaacatgc |
| SEQ ID NO:240 | gaccctgcaatcccaacactgg |
| SEQ ID NO:241 | ctctcaggccttcaaactacacc |
| SEQ ID NO:242 | caggaaagggctcgctcagtgg |
| SEQ ID NO:243 | atctgcaaaagcagcagagcagg |
| SEQ ID NO:244 | gtacccatgacagacaagttttagg |
| SEQ ID NO:245 | cttatcccctactgtctcctttgg |
| SEQ ID NO:246 | ggatggtctcgatctcctgacc |
| SEQ ID NO:247 | aggttagagaccttcctctaatgc |
| SEQ ID NO:248 | agctgggattacaggtgcctgc |
| SEQ ID NO:249 | gctgaggcaggttgggctgc |
| SEQ ID NO:250 | acatttaacgtctcctaacttctcc |
| SEQ ID NO:251 | gtgctgcgattacaggtgtgagc |
| SEQ ID NO:252 | tatgacagcagtattatactatcacc |
| SEQ ID NO:253 | ctggggaccaaatctgaactgcc |
| SEQ ID NO:254 | gtagctattgttatttccaaaagagg |
| SEQ ID NO:255 | gcttgggaccccaggacaagg |
| SEQ ID NO:256 | cctggccaacatggggaaatcc |
| SEQ ID NO:257 | aattgcttgaacctgggaggtgg |
| SEQ ID NO:258 | gcctaagacccaaaagctattagc |
| SEQ ID NO:259 | catattaaagggccatattcaaattgg |
| SEQ ID NO:260 | ggatgtaaccagtgtatatcacagg |
| SEQ ID NO:261 | ggaagtttagtccacatcttctagc |
| SEQ ID NO:262 | gcacccacaggacaaccacacg |
| SEQ ID NO:263 | gggacgcgcctgttaacaaagg |
| SEQ ID NO:264 | gggctgggggccacgctcc |
| SEQ ID NO:265 | cgcaaaagtgaagccctcctgg |
| SEQ ID NO:266 | gaaatcctacttgatctaaagtgagc |
| SEQ ID NO:267 | tttgagcaacttggaaaaaataagcg |
| SEQ ID NO:268 | ttcccaaaagacaaatagcacttcc |
| SEQ ID NO:269 | ccattttgaaaatcacagtgaattcc |
| SEQ ID NO:270 | gaaagaaaaccctgaattcaaaagg |
| SEQ ID NO:271 | tgctgaaaagaagcatttaaaagtgg |
| SEQ ID NO:272 | ctcttaccagtttcagagctttcc |
| SEQ ID NO:273 | ttttcagccaaaaatcaaggacagg |
| SEQ ID NO:274 | cttgagcccaggagtttgagacc |
| SEQ ID NO:275 | cgcctgtagtaccctctactagg |
| SEQ ID NO:276 | ggtaaagaaagaaggatttgaaaacc |
| SEQ ID NO:277 | taagagtaatgaggttaaagtttatgc |
| SEQ ID NO:278 | cattttattgtcacaggccatttgc |
| SEQ ID NO:279 | gccacgccttctcttctgccacc |
| SEQ ID NO:280 | tgcctctcctgactgcactgtg |
| SEQ ID NO:281 | ccatgctctaccacgcccttgg |
| SEQ ID NO:282 | cattcaggctggagtgcggtgg |
| SEQ ID NO:283 | cttaaaaattgtctggctaagacattg |
| SEQ ID NO:284 | ttgctcttgttgcccgggttgg |
| SEQ ID NO:285 | gagcttagaggaaaagtattatttcc |
| SEQ ID NO:286 | tggtgctgtgccagacgctgg |
| SEQ ID NO:287 | cagatcttttggctattgtcttgg |
| SEQ ID NO:288 | gaaggaaagggcctcccactgc |
| SEQ ID NO:289 | catgaaaagcatgctggggagg |
| SEQ ID NO:290 | caaacataaaaagctttaatagaagcc |
| SEQ ID NO:291 | tcccaactatgaaaaaatagaagacg |
| SEQ ID NO:292 | cacaaattagccgggcatggtgg |
| SEQ ID NO:293 | cttcctttactgagtctttctaaagc |
| SEQ ID NO:294 | tgtcctttgaaatgtaggtatgtgg |
| SEQ ID NO:295 | ggatcttgcaatactgacatctcc |
| SEQ ID NO:296 | atttgaaaagaactgaaggatctacc |
| SEQ ID NO:297 | gtgagctgagatctcgtctctgc |

TABLE 1-continued

| Sequence Identifier | Sequence |
|---|---|
| SEQ ID NO:298 | tttgtctgaaacagattctaaaagttgg |
| SEQ ID NO:299 | gcaggtgcctgtagtcccagc |
| SEQ ID NO:300 | gtttgagcttctaaaattcatggattc |
| SEQ ID NO:301 | gtggtaggtcaaaccgcaattcc |
| SEQ ID NO:302 | accaaatcagacatatcagctttgg |
| SEQ ID NO:303 | cacagaacggatcctcaataaagg |
| SEQ ID NO:304 | gttaacttctcccttctctttatgg |
| SEQ ID NO:305 | gtgttcagagagcttgatttccagg |
| SEQ ID NO:306 | cccacttgattttcccacatgg |
| SEQ ID NO:307 | atttatttagatgaagtgaatattttcc |
| SEQ ID NO:308 | atttagtttgtttaactgtgagtgc |
| SEQ ID NO:309 | gtacagaagtgcttgatgcatacc |
| SEQ ID NO:310 | aggcagataaaaattctccattagc |
| SEQ ID NO:311 | acaagcacgagccacagcacc |
| SEQ ID NO:312 | cgctcttgttgcccaggctgg |
| SEQ ID NO:313 | cccaaaacagactttctagataacc |
| SEQ ID NO:314 | ttcaaattgctttttttctactcacc |
| SEQ ID NO:315 | gatctgaaaaaagtgacaggttgg |
| SEQ ID NO:316 | cactgaaatttgaaaggaacatatgg |
| SEQ ID NO:317 | tctggtgcagtggcctctagg |
| SEQ ID NO:318 | accataagtggttttacctgatgg |
| SEQ ID NO:319 | cccaggcgcaggtgattctcc |
| SEQ ID NO:320 | ggtggctcacgcctgaaatcc |
| SEQ ID NO:321 | cacagtccacgtgccacaatcc |
| SEQ ID NO:322 | aatcatgttaacacatccctctcc |
| SEQ ID NO:323 | gaagagagtgttgaaaggttaagc |
| SEQ ID NO:324 | cgagaccatactggctaagatgg |
| SEQ ID NO:325 | attagccacacaataaatgttctgg |
| SEQ ID NO:326 | tttgaaaagcgttgcaatatgatgc |
| SEQ ID NO:327 | ggttgcagtgagccgagatcg |
| SEQ ID NO:328 | ggtgggaggactgcctgagc |
| SEQ ID NO:329 | aacagagagaaaaacacaaattacc |
| SEQ ID NO:330 | gatatctagaattcccaaatacttgg |
| SEQ ID NO:331 | gtgatagaattaaaggaaaaaataaacg |
| SEQ ID NO:332 | attgttccttttctaaatattctacc |
| SEQ ID NO:333 | cagcactttgggaggctgagg |
| SEQ ID NO:334 | cacagaggtttcacagtgctgg |
| SEQ ID NO:335 | aacttctgcttctgtccataatgc |
| SEQ ID NO:336 | gcctgtaatcccagcactttgg |
| SEQ ID NO:337 | gccagtaaacatatgaaaaggtgc |
| SEQ ID NO:338 | aattatgtaaataaagagtgaaaagg |
| SEQ ID NO:339 | cccctacacagaaaaaacaattcc |
| SEQ ID NO:340 | tgagtgtcaaagaaaaatacaattgg |
| SEQ ID NO:341 | atacacagagaaaatgagtccacc |
| SEQ ID NO:342 | aacactccccttctctgtttagc |
| SEQ ID NO:343 | gatattctttgcaacctaggatgc |
| SEQ ID NO:344 | ctctaaaactaatcagcaatgtaacc |
| SEQ ID NO:345 | cacctgtaatcccagcactttgg |
| SEQ ID NO:346 | cgtaaaactgccacaaagcttgtagg |
| SEQ ID NO:347 | gtggcagaggtgcaagcaagc |
| SEQ ID NO:348 | acagaaatgacaaacgcatgtacc |
| SEQ ID NO:349 | acactctcttagctaggctttgg |
| SEQ ID NO:350 | gagcttggaatagggcagttcc |
| SEQ ID NO;351 | ctgggttctttaaacatgtccagg |
| SEQ ID NO:352 | tcaagaaaggacactgcagtggc |
| SEQ ID NO:353 | catgcacacaaactatctcattcc |
| SEQ ID NO:354 | tagccgggcatggtggcacg |
| SEQ ID NO:355 | atcatgctgattgaatttcaaatagc |
| SEQ ID NO:356 | ttggcatgcagggcagtgacc |
| SEQ ID NO:357 | ggtggtgagataataacacctgc |
| SEQ ID NO:358 | ttgctatataataatcatttgtgatcc |
| SEQ ID NO:359 | cggtaactgttactctgggatgg |
| SEQ ID NO:360 | aggctaggttcccttctcttcc |
| SEQ ID NO:361 | gtagtgcctagcacagagaaagc |
| SEQ ID NO:362 | ctagcctgggcaacaagagcg |
| SEQ ID NO:363 | tctctctcctctctgggatcag |
| SEQ ID NO:364 | gtttgaatatttgtatgcagcaagc |
| SEQ ID NO:365 | tagaacaaattctggcttataaaagc |
| SEQ ID NO:366 | ccactctacctttattccttgcc |
| SEQ ID NO:367 | agaccagaatatgcaagcagagg |
| SEQ ID NO:368 | ggacgtttgctggtgtctgcg |
| SEQ ID NO:369 | aaggaacaaactgttgtcacatgc |
| SEQ ID NO:370 | atgtagctgggactacaggtgc |
| SEQ ID NO:371 | ggctcatgcctgtaatcccagc |
| SEQ ID NO:372 | atgaggttttcacacaaaagatgc |
| SEQ ID NO:373 | tgggcgacagagcaagactcc |
| SEQ ID NO:374 | aaatgtccctaaaagtgatcaacagc |
| SEQ ID NO:375 | cagactcagttttacctcatcagc |

TABLE 1-continued

| Sequence Identifier | Sequence |
|---|---|
| SEQ ID NO:376 | agtgatctttcctctttaacctcc |
| SEQ ID NO:377 | ccagctattcaggaggccaagg |
| SEQ ID NO:378 | cttaaacattatgacactgtcttgc |
| SEQ ID NO:379 | ccaggtctatgaggccgttcc |
| SEQ ID NO:380 | tccaaagcatccctacattatacc |
| SEQ ID NO:381 | acatacatacatgcagtgactagc |
| SEQ ID NO:382 | tacaggtgccagccaccatgc |
| SEQ ID NO:383 | gcctgtaatcccagcactctgg |
| SEQ ID NO:384 | gacagagtcccactcttgttgc |
| SEQ ID NO:385 | gtgccttccaaagcagtgtagg |
| SEQ ID NO:386 | tatcttactgggtatgtataatgcc |
| SEQ ID NO:387 | caaaggaaatacgtcctaccagg |
| SEQ ID NO:388 | ccttttctcacagacatgcttcc |
| SEQ ID NO:389 | taaacacagtgagcagaatccc |
| SEQ ID NO:390 | ataaagcaaacttctaaaagggtcc |
| SEQ ID NO:391 | accactacactccagcctggg |
| SEQ ID NO:392 | gatacctgggtcagagtaagtgc |
| SEQ ID NO:393 | tgtaatctcagctacttgggagg |
| SEQ ID NO:394 | gtgtcgtcttctcttcctctacg |
| SEQ ID NO:395 | ctggctagtatgaggttggtgc |
| SEQ ID NO:396 | ggactagccacatttcaaccagg |
| SEQ ID NO:397 | gcagtatactgagaatttagtttcc |
| SEQ ID NO:398 | gaggctgaggcaggagaatgg |
| SEQ ID NO:399 | cattgtttgatgaaggtcaacagc |
| SEQ ID NO:400 | cagacaagagtggctacggcag |
| SEQ ID NO:401 | acgcccagccagattattcagg |
| SEQ ID NO:402 | ggaaccagaaagaagtgcaaagg |
| SEQ ID NO:403 | tgagccatcttggaggcaggc |
| SEQ ID NO:404 | caggaccttcctacaaacctcc |
| SEQ ID NO:405 | aacacaacatatctgaccttacgc |
| SEQ ID NO:406 | gccttagaagtccagaggaaagc |
| SEQ ID NO:407 | tgacgtacccagtagaccttcc |
| SEQ ID NO:408 | ctctgcaagcctgggaaacagg |
| SEQ ID NO:409 | gccttgtcccaagtcctaagg |
| SEQ ID NO:410 | gcaaagggactcctggaattcc |
| SEQ ID NO:411 | gctcctgcctgtaatcccagc |
| SEQ ID NO:412 | gaaggaaacagaaaaagcagaggc |
| SEQ ID NO:413 | cttactaccgttcttcttcactgg |
| SEQ ID NO:414 | actattctgtttctttaggtttactgc |
| SEQ ID NO:415 | cggtggctcacacctgtaatcc |
| SEQ ID NO:416 | agccagagttctgtgctctagg |
| SEQ ID NO:417 | taatttgcatttcgtgccgctcc |
| SEQ ID NO:418 | cacttttaatacagatcccaatagg |
| SEQ ID NO:419 | atgtattttttcttttcctgtcaagc |
| SEQ ID NO:420 | aaatgttaacattattctccctaagg |
| SEQ ID NO:421 | catatgcccagatcccgtctcc |
| SEQ ID NO:422 | acaggtgtgagccgctgcacc |
| SEQ ID NO:423 | gccaagacgtttacagttttggc |
| SEQ ID NO:424 | aggaaacttctgaggatgatggg |
| SEQ ID NO:425 | gctttatagggcagtctgaattcc |
| SEQ ID NO:426 | ttagaataaaagttatctcgggagg |
| SEQ ID NO:427 | taatttcttcagctttatccctcag |
| SEQ ID NO:428 | cacatgactaattctctattcattcc |
| SEQ ID NO:429 | aaagacctcaagaaaagagtcacc |
| SEQ ID NO:430 | gacccataaagattatatgcccag |
| SEQ ID NO:431 | aaagtactaatgcagtgtgtcagc |
| SEQ ID NO:432 | gaggttcctcgattcccctgc |
| SEQ ID NO:433 | ggagagcagaggaattcacagg |
| SEQ ID NO:434 | agtaattagaaactgattctaagacg |
| SEQ ID NO:435 | cataccattgccaatccgttcc |
| SEQ ID NO:436 | attacgggtgcctgccactgc |
| SEQ ID NO:437 | cagccaggcagaggagagagg |
| SEQ ID NO:438 | ttttcattccaagtttctgtttggg |
| SEQ ID NO:439 | tttcaaataggaatttggataatccc |
| SEQ ID NO:440 | taagccgagatcacaccactgc |
| SEQ ID NO:441 | ccttcagcgcattatatcttggc |
| SEQ ID NO:442 | ccatctaatccatcttaaattcacc |
| SEQ ID NO:443 | gagtggagactgcgccactgc |
| SEQ ID NO:444 | aatcatgtgccaattaaaccatggc |
| SEQ ID NO:445 | cccagggaccagaccagacc |
| SEQ ID NO:446 | ctcactcaccagtgaaaatcagc |
| SEQ ID N0:447 | ggttgctctcgaactcctgacc |
| SEQ ID NO:448 | gttcccccagctccttctgc |
| SEQ ID NO:449 | agaaagatgtagaagggtccagc |
| SEQ ID NO:450 | gggaaaaggtgtattatgcaagcg |
| SEQ ID NO:451 | ctctctcagacctaatgcaaaagc |
| SEQ ID NO:452 | aactatacatacagtatttgtattagc |
| SEQ ID NO:453 | aaattaatgcaatccatgatccagg |

TABLE 1-continued

| Sequence Identifier | Sequence |
|---|---|
| SEQ ID NO:454 | ctttctccactctaagagaaccc |
| SEQ ID NO:455 | ttttggtgtgttcatattggctgc |
| SEQ ID NO:456 | gcttccacaaatgacagacaaagg |
| SEQ ID NO:457 | ggctcatgcttgtaatcccagc |
| SEQ ID NO:458 | catatgaattgttgttcctttgtagg |
| SEQ ID NO:459 | cactggtacaagtccaagagtcc |
| SEQ ID NO:460 | gaccctgtgtctacttcctggg |
| SEQ ID NO:461 | tatttgaactatctcttgaaatgtcc |
| SEQ ID NO:462 | ctgattaaaaagtattacccttggc |
| SEQ ID NO:463 | tttgaaactgcactcaataacttgg |
| SEQ ID NO:464 | agtaatgtgtcatgatccaatggc |
| SEQ ID NO:465 | gaaagcatttcccaatgtctcacc |
| SEQ ID NO:466 | caatggacaaaaggcccaactgc |
| SEQ ID NO:467 | tccagctctggcttttttgttaag |
| SEQ ID NO:468 | acggagtctcactccgtgacc |
| SEQ ID NO:469 | ctatgtcatagtcaagagactttgc |
| SEQ ID NO:470 | gttcaagcgattctcctgtctcg |
| SEQ ID NO:471 | ccacctaatacttaaatacggaagc |
| SEQ ID NO:472 | atattcaacaaacttaatagtgaagtg |
| SEQ ID NO:473 | ttacaggcgtgagtcaccatgc |
| SEQ ID NO:474 | aacacctccaagaggccaaacg |
| SEQ ID NO:475 | tactattggcaaatttcaattatatgg |
| SEQ ID NO:476 | agcccacatcctaaaattcaataag |
| SEQ ID NO:477 | gaaagtggataagtgtttgtctgg |
| SEQ ID NO:478 | ggccaggcattcaagaccagc |
| SEQ ID NO:479 | agccaacaacaaaaagacacaacc |
| SEQ ID NO:480 | ttgagcccaggagttcaagacc |
| SEQ ID NO:481 | cagactaaagatctcagagagaaac |
| SEQ ID NO:482 | cgcttgtaatcccagcacttgg |
| SEQ ID NO:483 | aaaagtgaaatcagaatttgtttcc |
| SEQ ID NO:484 | caggcgtgagcaactgtgtcc |
| SEQ ID NO:485 | ggtccagtaggatctcgtttgc |
| SEQ ID NO:486 | actttgaaaatgttgttatagctggg |
| SEQ ID NO:487 | ttccctgcatctaagtcttctcc |
| SEQ ID NO:488 | agatatctaccattgaagagtttgc |
| SEQ ID NO:489 | agtcttcacttcactttgttgtcc |
| SEQ ID NO:490 | ccatgcaggtatgaaatataaagc |
| SEQ ID NO:491 | tgggtgacagagtgagactcc |
| SEQ ID NO:492 | acagcaataccgggttaacatgc |
| SEQ ID NO:493 | tttatgtaaaagatgaatgcgaggc |
| SEQ ID NO:494 | ctactctgctactgggaacagg |
| SEQ ID NO:495 | caaacgttagtctggcaaaatgcg |
| SEQ ID NO:496 | tgcacgctaccacacccagc |
| SEQ ID NO:497 | aattcttggatctgtgtgtttactgc |
| SEQ ID NO:498 | taccagttatcattctctttctgc |
| SEQ ID NO:499 | atccacccacctcggcctcc |
| SEQ ID NO:500 | cactctgcctggcccttaatgg |
| SEQ ID NO:501 | atagtttgtttaatatgccactaagg |
| SEQ ID NO:502 | gcgtgagccaccgcacctgg |
| SEQ ID NO:503 | ctccatcacacaaattttatgtggc |
| SEQ ID NO:504 | agacggagtctcgttctgtcgc |
| SEQ ID NO:505 | tcccaggttcaagccattctcc |
| SEQ ID NO:506 | tattttgagagtctcactctgtcg |
| SEQ ID NO:507 | gtctcgaactcctgacctcagg |
| SEQ ID NO:508 | aaggaggtgaagagtgaactacg |
| SEQ ID NO:509 | gtctcaggttttggacttacttgg |
| SEQ ID NO:510 | tttacagatcttaaatgcattaggac |
| SEQ ID NO:511 | gtacactgaacaaaggagacagg |
| SEQ ID NO:512 | ctggtagtaatgcaaaatagcacc |
| SEQ ID NO:513 | catttaatgtgaaatgaattataagcc |
| SEQ ID NO:514 | gagacagggtttcactatgttgg |
| SEQ ID NO:515 | ccagcactttggaaggctgagg |
| SEQ ID NO:516 | gaaaccaagtatcatggtaaattgc |
| SEQ ID NO:517 | cagtgagggctgctcagttcc |
| SEQ ID NO:518 | gccaggtgcggtggctcacg |
| SEQ ID NO:519 | catgcctgtaatcccagctacc |
| SEQ ID NO:520 | atgtaaatggtacagtcactttagg |
| SEQ ID NO:521 | cccacaatacagagaactcttacc |
| SEQ ID NO:522 | tgaaacatgcagcccagtgtcc |
| SEQ ID NO:523 | tgttttttctcctgccttcaatcc |
| SEQ ID NO:524 | gctttcctgggtctccatctgg |
| SEQ ID NO:525 | gcagccgcttgaaaacaaaacagc |
| SEQ ID NO:526 | gatcacgttacatttgggggtgg |
| SEQ ID NO:527 | taggctgaaaaactaaaatttgttgc |
| SEQ ID NO:528 | ctcctttgggctccttagtcc |
| SEQ ID NO:529 | gcctcggcctcccaaagtgc |
| SEQ ID NO:530 | aatgcctagagagatttggcagg |
| SEQ ID NO:531 | gagatggggtttcactatgttgg |

TABLE 1-continued

| Sequence Identifier | Sequence |
|---|---|
| SEQ ID NO:532 | tgtgatcttgccactgcactcc |
| SEQ ID NO:533 | acttctcctccatttgtttcttcg |
| SEQ ID NO:534 | cgtgcccgggctcagttctac |
| SEQ ID NO:535 | ccaaaacaataaaatcacaatttggg |
| SEQ ID NO:536 | ctgaactgccttagagtaaatccg |
| SEQ ID NO:537 | atttctgtatcaggtctgtgttcc |
| SEQ ID NO:538 | ggctgaccccttcactgtttcc |
| SEQ ID NO:539 | caaaaattagccaggcatggtgg |
| SEQ ID NO:540 | gcagtgagcagtgatcgcacc |
| SEQ ID NO:541 | aaagactgtgaactaacttgtttgc |
| SEQ ID NO:542 | tgccaagaattacacattattaggc |
| SEQ ID NO:543 | ggccaggatgtcattaactttcc |
| SEQ ID NO:544 | gtaagactgacgtgtattgtgc |
| SEQ ID NO:545 | cccggtgaggccgcacatcc |
| SEQ ID NO:546 | cctgcgccttaaccccctcc |
| SEQ ID NO:547 | cggcgcctaggggccatcg |
| SEQ ID NO:548 | acttaaggaaacgaacatgacacc |
| SEQ ID NO:549 | gagaccgagtcttgctgtgtcg |
| SEQ ID NO:550 | gtattaattgaagatgatttggaatgc |
| SEQ ID NO:551 | tctttaaaagactatcgctgaggc |
| SEQ ID NO:552 | aaaagagacatcagtgagcatcc |
| SEQ ID NO:553 | gttcatgttttctttgacgtctcc |
| SEQ ID NO:554 | tttcgaaagttcaggctgagtgc |
| SEQ ID NO:555 | gaccctcaaaacaatcctctaagg |
| SEQ ID NO:556 | caaaacacacttagaaacaaactgc |
| SEQ ID NO:557 | gcctgggcgacatagtgagacc |
| SEQ ID NO:558 | ggcaggagaatggcgtgaacc |
| SEQ ID NO:559 | tttgctcgttgcccaggctgg |
| SEQ ID NO:560 | gcaacttaatgtgatagaataatagc |
| SEQ ID NO:561 | cctcccttctgctgccagc |
| SEQ ID NO:562 | ccacaacaatgtaaactcctctgg |
| SEQ ID NO:563 | tactctccctagagttcgttccc |
| SEQ ID NO:564 | gggtccccctttggccattcc |
| SEQ ID NO:565 | gatcttggctcacttcaacctcc |
| SEQ ID NO:566 | agggaaatatttaaaccttgg |
| SEQ ID NO:567 | aatgcaatggtgcatttacagagg |
| SEQ ID NO:568 | tcattttatctatttctacatggtcc |
| SEQ ID NO:569 | ggaagggaaatgccatgaacc |
| SEQ ID NO:570 | agtgaacattttctgcagcctcc |
| SEQ ID NO:571 | caacaggacgtcaggcgatcc |
| SEQ ID NO:572 | ccttcaggctgtcctgaaaagg |
| SEQ ID NO:573 | agtctcactccatcgcccagg |
| SEQ ID NO:574 | actgtgaacagtagttaactcagg |
| SEQ ID NO:575 | gcatgcctgtaatccaagctgc |
| SEQ ID NO:576 | gaaacaattctcttttcacacttgc |
| SEQ ID NO:577 | ggctcatgcctgttatcccagc |
| SEQ ID NO:578 | agaagaagcttagtcatatgtttgg |
| SEQ ID NO:579 | cagatgcttgagccaaacaaatgg |
| SEQ ID NO:580 | ctggcagacagagtgagactcc |
| SEQ ID NO:581 | aatgtgtgaatattattcattacaggg |
| SEQ ID NO:582 | gcaggagaattgcttgaacctgg |
| SEQ ID NO:583 | ctttagtcaaattaaaacagtctatcc |
| SEQ ID NO:584 | gatttctatctcctgcaaccacc |
| SEQ ID NO:585 | ttcttgtgtaactactaaaaatctcc |
| SEQ ID NO:586 | aaagggtcttcataaggctaatgg |
| SEQ ID NO:587 | ctcttaaggattatttatatgaagacc |
| SEQ ID NO:588 | caggaggagccccagagc |
| SEQ ID NO:589 | tcctggggatggttggatgc |
| SEQ ID NO:590 | tgaccccacagagtttacacagc |
| SEQ ID NO:591 | agtcagggcaggctctgcc |
| SEQ ID NO:592 | tattttggccccatccagaaagc |
| SEQ ID NO:593 | cacccagagtacagctttgttcc |
| SEQ ID NO:594 | gaggagccccagagcctgc |
| SEQ ID NO:595 | tggggatggttggatgcttacc |
| SEQ ID NO:596 | cccacagagtttacacagcttgc |
| SEQ ID NO:597 | caggctctgcccactcacc |
| SEQ ID NO:598 | ccatccagaaagcccaaagcc |
| SEQ ID NO:599 | ccagagtacagctttgttcctcattc |
| SEQ ID NO:600 | gcagtacaaacaacgcacagcg |
| SEQ ID NO:601 | ctgccaccctccacagtccc |
| SEQ ID NO:602 | gccaagaccatgcatgcg |
| SEQ ID NO:603 | cccagggacaaagagactccc |
| SEQ ID NO:604 | caggaagcagacagtcttctagttcc |
| SEQ ID NO:605 | tgcctgtaatcccaacactttgg |
| SEQ ID NO:606 | tccctctggccaggatggg |
| SEQ ID NO:607 | atggggaatgggagtaggaagc |
| SEQ ID NO:608 | cagatcagttctcccctccagc |
| SEQ ID NO:609 | acaaaaaagaaacatgctcagagagg |

TABLE 1-continued

| Sequence Identifier | Sequence |
|---|---|
| SEQ ID NO:610 | tggtggcatgcatctgtagtcc |
| SEQ ID NO:611 | aggtgctctatagatgttagcatccc |
| SEQ ID NO:612 | ccaggacaggatggagatctgg |
| SEQ ID NO:613 | agggaacctgtgcattatccttgc |
| SEQ ID NO:614 | cagaagtcttgctttaaggaggagg |
| SEQ ID NO:615 | gggtacgtgaaactcaccaagg |
| SEQ ID NO:616 | cagagtgtggcaagcaaggg |
| SEQ ID NO:617 | aacattttaaaggtacaaataacgtggg |
| SEQ ID NO:618 | tagggagcaacagccattaagc |
| SEQ ID NO:619 | ggtgcactgtccagctctgg |
| SEQ ID NO:620 | actctcgctgaactcgcctgg |
| SEQ ID NO:621 | ctcggtctctggtggtacgc |
| SEQ ID NO:622 | gcaagaggtccgagctggg |

TABLE 1-continued

| Sequence Identifier | Sequence |
|---|---|
| SEQ ID NO:623 | ggaagaagtgaaacaagagatgaagg |
| SEQ ID NO:624 | cccagagaacaaaccggattagg |
| SEQ ID NO:625 | cccttcaaccttctccaatctgc |
| SEQ ID NO:626 | cccatgtccagtggtttaggg |
| SEQ ID NO:627 | gagattggtgggagacagatgg |
| SEQ ID NO:628 | cttctcagctcaaagttccagcg |
| SEQ ID NO:629 | gaatgggagagatgaccagagg |
| SEQ ID NO:630 | aagggcaaggggtatgtgg |
| SEQ ID NO:631 | ggaaggaagcatgggaacacc |
| SEQ ID NO:632 | ccatcaatgctctgtctgtctgg |
| SEQ ID NO:633 | gtgccgtgactgtgcttgg |
| SEQ ID NO:634 | acatcccattgacctcatcaagc |

The invention claimed is:

1. A method of identifying a gene breakpoint, said method comprising:
   (i) in a first round amplification reaction, contacting a DNA sample with:
      (a) one or more forward primers directed to the antisense strand of a genomic DNA region of the flanking gene or fragment thereof, said region being located 5' relative to the gene breakpoint; and
      (b) one or more reverse primers directed to the sense strand of a genomic DNA region of the flanking gene or fragment thereof, said region being located 3' relative to the gene breakpoint;
   wherein all of the forward primers or all of the reverse primers or all of both the forward and reverse primers are operably linked at their 5' end to an oligonucleotide tag; and
      if the forward primers are operably linked to an oligonucleotide tag then the oligonucleotide tags of the forward primers are the same relative to the forward primer tags of step (i)(a);
      if the reverse primers are operably linked to an oligonucleotide tag then the oligonucleotide tags of the reverse primers are the same relative to the reverse primer tags of step (i)(b);
      if both the forward primers and the reverse primers are operably linked to an oligonucleotide tag then forward primer oligonucleotide tags are different relative to the reverse primer tags; and
      (c) if a forward primer tag is present then hybridizing a primer directed to the forward primer oligonucleotide tag of step (i)(a); and
      (d) if a reverse primer tag is present then hybridizing a primer directed to the reverse primer oligonucleotide tag of step (i)(b);
   (ii) amplifying the DNA sample of step (i);
   (iii) in a second round amplification reaction, contacting the amplicon generated in step (ii) with:
      (a) one or more forward primers directed to the antisense strand of a genomic DNA region of the flanking gene or fragment thereof, said region being located 5' relative to the gene breakpoint and 3' relative to one or more of the regions of step (i)(a); and
      (b) one or more reverse primers directed to the sense strand of a genomic DNA region of the flanking gene or fragment thereof, said region being located 3' to the gene breakpoint and 5' relative to one or more of the regions of step (i)(b);
   wherein all of the forward primers or all of the reverse primers or all of both the forward and reverse primers are operably linked at their 5' end to an oligonucleotide tag; and
      if the forward primers are operably linked to an oligonucleotide tag then the oligonucleotide tags of the forward primers are the same relative to the forward primer tags of step (iii)(a);
      if the reverse primers are operably linked to an oligonucleotide tag then the oligonucleotide tags of the reverse primers are the same relative to the reverse primer tags of step (iii)(b);
      if both the forward primers and the reverse primers are operably linked to an oligonucleotide tag then forward primer oligonucleotide tags are different relative to the reverse primer tags and which forward and reverse primer tags of step (iii) are different relative to the forward and reverse primer tags of step (i); and
      (c) if a forward primer tag is present then hybridizing a primer directed to the forward primer oligonucleotide tag of step (iii)(a); and (d) if a reverse primer tag is present then hybridizing a primer directed to the reverse primer oligonucleotide tag of step (iii)(b);

(iv) amplifying the DNA sample of step (iii); and (v) analysing the amplified DNA.

2. The method according to claim 1 wherein:
(i) one primer is used in step (i)(a) and 24-400 primers are used in step (i)(b); or
(ii) one primer is used in step (i)(b) and two or more primers are used in step (i)(a).

3. The method according to claim 1 wherein:
(i) one primer is used in step (iii)(a) and 24-400 primers are used in step (iii)(b); or
(ii) one primer is used in step (iii)(b) and two or more primers are used in step (iii)(a).

4. The method according to claim 1 wherein said gene breakpoint is a homologous recombination point or said gene translocation breakpoint is a chromosomal gene translocation breakpoint.

5. The method according to claim 4 wherein said gene translocation breakpoint is selected from:
(i) BCR-ABL translocation
(ii) PML-RARa translocation
(iii) t(2;5)(p23;q35) translocation
(iv) t(8;14) translocation
(v) t(9;22)(q34;q11) translocation
(vi) t(11;14) translocation
(vii) t(11;22)(q24;q11.2-12) translocation
(viii) t(14;18)(q32;q21) translocation
(ix) t(17;22) translocation
(x) t(15;17) translocation
(xi) t(1;12) (q21;p13) translocation
(xii) t(9;12)(p24;p13) translocation
(xiii) t(X;18)(p11.2;q11.2) translocation
(xiv) t(1;11)(q42.1;q14.3) translocation
(xv) t(1;19) translocation.

6. The method according to claim 1 wherein 1-30 primers are used in step (i)(a) and 24-400 primers are used in step (i)(b).

7. The method according to claim 1 wherein 1-30 primers are used in step (iii)(a) and 24-400 primers are used in step (iii)(b).

8. The method according to claim 1 wherein said amplified DNA of step (iv) is subjected to a further step of amplification, selection or enrichment.

9. The method according to claim 1 wherein said gene breakpoint is a chromosomal BCR-ABL translocation and:
(a) the forward primers of step (i)(a) have the nucleic acid sequences of SEQ ID NOs:10-15;
(b) the reverse primers of step (i)(b) have the nucleic acid sequences of SEQ ID NOs:23-304 and are linked to the oligonucleotide tag having the nucleic acid sequence of SEQ ID NO:22;
(c) the forward primers of step (iii)(a) have the nucleic acid sequences of SEQ ID NOs:16-21; and
(d) the reverse primers of step (iii)(b) have the nucleic acid sequences of SEQ ID NOs:306-587 and are linked to the oligonucleotide tag having the nucleic acid sequence of SEQ ID NO:305.

10. The method according to claim 1 wherein said gene breakpoint is a chromosomal PML-RARalpha translocation and:
(a) the forward primers of step (i)(a) have the nucleic acid sequences of SEQ ID NOs:588-593; and
(b) the reverse primers of step (i)(b) have the nucleic acid sequences of SEQ ID NOs:601-634 and are linked to the oligonucleotide tag having the nucleic acid sequence of SEQ ID NO:22
and wherein step (ii) is followed by bottleneck PCR which is performed using primers having the nucleic acid sequences of SEQ ID NOs:594-599.

11. The method according to claim 8, wherein either the forward primers or the reverse primers of step (iii)(a) or (b) have been designed or are used under conditions wherein they do not hybridize and extend efficiently.

\* \* \* \* \*

SEQUENCE LISTING

<160> NUMBER OF SEQ ID NOS: 634

<210> SEQ ID NO 1
<211> LENGTH: 203
<212> TYPE: DNA
<213> ORGANISM: Homo sapiens
<220> FEATURE:
<223> OTHER INFORMATION: BCR region

<400> SEQUENCE: 1
gtgggccccc ccgtttccgt gtacagggca cctgcaggga gggcaggcag ctagcctgaa    60
ggctgatccc cccttcctgt tagcactttt gatgggacta gtggactttg gttcagaagg   120
aagagctatg cttgttaggg cctcttgtct cctcccagga gtggacaagg tgggttagga   180
gcagtttctc cctgagtggc tgc                                           203

<210> SEQ ID NO 2
<211> LENGTH: 376
<212> TYPE: DNA
<213> ORGANISM: Homo sapiens
<220> FEATURE:
<223> OTHER INFORMATION: ABL region

<400> SEQUENCE: 2
caccacgtct ggctaatttt tgtatttta gtagagatgg ggtttcaaca tgttagccag    60
gctggtctcg aactcctgac ctcaggtgat ccacccgcct gggccctcca agtgctggg   120 attacaggca ggagccactg tgcccggcct gacctcatat ttgaataccg agttttagtt   180
ctggaggagc tgcaggtttt atgaaagggg aacacatttg attcctcaga gcagccacag   240
gccagctctc tgaagtaaag tgcacgtgtg catgtgtgtg cacactcaca cacacgtaca   300
cacacattca caaataactg tgcccggcct gacctcatat ttgaataccg agttttagtt   360
ctggaggagc tgcagg                                                   376

<210> SEQ ID NO 3
<211> LENGTH: 231

```
<212> TYPE: DNA
<213> ORGANISM: Homo sapiens
<220> FEATURE:
<223> OTHER INFORMATION: BCR region

<400> SEQUENCE: 3
tttgggaggc tgaggcaggt ggatcgcttg agctcaggag ttggagacca gcctgaccaa      60
catggtgaaa ccctgtgtct actaaaaata caaagattag ccgggctagg cagtgggcac     120
ctgtaatcac aactgcttgg gaggctgagg gaagagaatc gcttgaaccc aggaggcgga     180
ggttgcagtg agccgagctt gtgccactgc attccagcct gggcgacaga g              231

<210> SEQ ID NO 4
<211> LENGTH: 249
<212> TYPE: DNA
<213> ORGANISM: Homo sapiens
<220> FEATURE:
<223> OTHER INFORMATION: ABL region

<400> SEQUENCE: 4
ggtctcactc tgttgaactc ctggtggcct caagggatcc tcctacctcg gcctcacaaa      60
gtattggaat tacaggtgtg agtcactgca gctggcctcc acttatcact gtgaggagta     120
aacagctgca tggtgggctt aatgccatct aacacgagtg actccatgtt cagacagtag     180
gatcacaaat gattattata tagcaatgaa tggccacagg tacatagact aaggagccac     240
atccctgct                                                             249

<210> SEQ ID NO 5
<211> LENGTH: 212
<212> TYPE: DNA
<213> ORGANISM: Homo sapiens
<220> FEATURE:
<223> OTHER INFORMATION: BCR region

<400> SEQUENCE: 5
cctccagcta cctgccagcc ggcacttttg gtcaagctgt tttgcattca ctgttgcaca      60
tatgctcagt cacacacaca gcatacgcta tgcacatgtg tccacacaca ccccacccac     120
atcccacatc accccgaccc cctctgctgt ccttggaacc ttattacact tcgagtcact     180
ggtttgcctg tattgtgaaa ccagctggat cc                                   212

<210> SEQ ID NO 6
<211> LENGTH: 200
<212> TYPE: DNA
<213> ORGANISM: Homo sapiens
<220> FEATURE:
<223> OTHER INFORMATION: ABL region

<400> SEQUENCE: 6
ttatttataa caacattttc agcgtggcaa ctgcagtttc agaatggtgg aattatacca      60
gtcagagaga gatgcaaatg atttaaaata ggaagaaagc aggtgtctgg cccagaggac     120
cagattaaga agaccccatg agagttacaa tagttagtga aaatggtgct tctgcaaacc     180
tcatgtctac agaagctggt                                                 200

<210> SEQ ID NO 7
<211> LENGTH: 213
<212> TYPE: DNA
<213> ORGANISM: Homo sapiens
<220> FEATURE:
<223> OTHER INFORMATION: BCR region
```

```
<400> SEQUENCE: 7
tgcaccttca taacataatc tttctcctgg gccctgtct ctggctgcct cataaacgct    60
ggtgtttccc tcgtgggcct ccctgcatcc ctgcatctcc tcccgggtcc tgtctgtgag   120
caatacagcg tgacacccta cgctgccccg tggtcccggg cttgtctctc cttgcctccc   180
tgttaccttt ctttctatct cttccttgcc ccg                                213

<210> SEQ ID NO 8
<211> LENGTH: 251
<212> TYPE: DNA
<213> ORGANISM: Homo sapiens
<220> FEATURE:
<223> OTHER INFORMATION: ABL region

<400> SEQUENCE: 8
gtgagctccg cctcctgtca gatcagtggc ggcattagtt tctcatagga gcatgaaatc    60
tattgtgaac agtacatgcg atggatccag gttgcgtgct cctagtgaga atctaatgcc   120
tgaggatctc tcattgtctc ttatcactcc cagataggac tgtctagttg caggaaaaca   180
agctcagggc tcccactgat tctacattac agtgggttgt ataattatta tatattacaa   240
tgtaataata a                                                        251

<210> SEQ ID NO 9
<211> LENGTH: 63
<212> TYPE: DNA
<213> ORGANISM: Homo sapiens

<400> SEQUENCE: 9
ggagtctgag gagggaagg aggcaaggtt ggctcggatc ccagccagta agtctgggtg     60
tgg                                                                  63

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
cttctccctg acatccgtgg                                                20

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 11
acacagcata cgctatgcac atgtg                                          25

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12
gaggttgttc agatgaccac gg                                             22
```

```
<210> SEQ ID NO 13
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 13
cagctactgg agctgtcaga acag                                              24

<210> SEQ ID NO 14
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 14
tgggcctccc tgcatcc                                                      17

<210> SEQ ID NO 15
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 15 tcccctgca ccccacg                                                       17

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 16
tgacatccgt ggagctgcag atgc                                              24

<210> SEQ ID NO 17
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 17
acatgtgtcc acacacccc cacc                                               24

<210> SEQ ID NO 18
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 18
accacgggac acctttgacc ctgg                                              24

<210> SEQ ID NO 19
<211> LENGTH: 24
<212> TYPE: DNA
<213> ORGANISM: Artificial Sequence
<220> FEATURE:
<223> OTHER INFORMATION: Synthetic oligonucleotide
```

```
<400> SEQUENCE: 19
ctggagctgt cagaacagtg aagg                                     24

<210> SEQ ID NO 20
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 20
tccctgcatc cctgcatctc ctcc                                     24

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 21
cccacgactt ctccagcact gagc                                     24

<210> SEQ ID NO 22
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 22
gcaacactgt gacgtactgg agg                                      23

<210> SEQ ID NO 23
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 23
gtctatctaa aattcacaag gaatgc                                   26

<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 24
aggcaaagta aaatccaagc accc                                     24

<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 25
cactcctgca ctccagcctg g                                        21

<210> SEQ ID NO 26
<211> LENGTH: 24
```

```
<212> TYPE: DNA
<213> ORGANISM: Artificial Sequence
<220> FEATURE:
<223> OTHER INFORMATION: Synthetic oligonucleotide

<400> SEQUENCE: 26
caaccaccaa agtgcttttc ctgg                                            24

<210> SEQ ID NO 27
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 27
atatggcatc tgtaaatatt accacc                                          26

<210> SEQ ID NO 28
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 28
tgcctcggcc tcccaaagtg c                                               21

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
agccaccaca cccagccagg                                                 20

<210> SEQ ID NO 30
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 30
aataactgtt ttctcccccc aaaac                                           25

<210> SEQ ID NO 31
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 31
tgttttacaa aaatggggcc atacc                                           25

<210> SEQ ID NO 32
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 32
```
acttaagcaa attctttcat aaaaaggg                                               28

<210> SEQ ID NO 33
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 33
ctttcaattg ttgtaccaac tctcc                                                  25

<210> SEQ ID NO 34
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 34
acctcctgca tctctccttt tgc                                                    23

<210> SEQ ID NO 35
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 35
aaataaagtt ttgagaacca taagtgg                                                27

<210> SEQ ID NO 36
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 36
caccatcaca gctcactgca gc                                                     22

<210> SEQ ID NO 37
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 37
aacctctttg agaatcggat agcc                                                   24

<210> SEQ ID NO 38
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 38
aaataaagta catacctcca attttgc                                                27

<210> SEQ ID NO 39
<211> LENGTH: 25
<212> TYPE: DNA
<213> ORGANISM: Artificial Sequence

```
<220> FEATURE:
<223> OTHER INFORMATION: Synthetic oligonucleotide

<400> SEQUENCE: 39
gacacattcc tatgggttta attcc                                            25

<210> SEQ ID NO 40
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 40
tgtaaaatat ggtttcagaa gggagg                                           26

<210> SEQ ID NO 41
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 41
gcaggtggat aacgaggtca gg                                               22

<210> SEQ ID NO 42
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 42
ccagccaaga atttcaaaga ttagc                                            25

<210> SEQ ID NO 43
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 43
gaagggagat gacaaaggga acg                                              23

<210> SEQ ID NO 44
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 44
gcagaagaac tgcttgaacc tgg                                              23

<210> SEQ ID NO 45
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 45
gtggtcccag ctactcgaga gg                                               22
```

<210> SEQ ID NO 46
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 46
ccctcagcaa aactaactga aaagg                                      25

<210> SEQ ID NO 47
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 47
tagaaaccaa gatatctaga attccc                                     26

<210> SEQ ID NO 48
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 48
ccacgcccgg cggaataaat gc                                         22

<210> SEQ ID NO 49
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 49
acaaaaaaag aggcaaaaac tgagag                                     26

<210> SEQ ID NO 50
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 50
ctgggcgcag tggctcatgc c                                          21

<210> SEQ ID NO 51
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 51
tggctgtgag gctgagaact gc                                         22

<210> SEQ ID NO 52
<211> LENGTH: 22
<212> TYPE: DNA
<213> ORGANISM: Artificial Sequence
<220> FEATURE:
<223> OTHER INFORMATION: Synthetic oligonucleotide

```
<400> SEQUENCE: 52
ctgggcgaca gagtgagact cc                                             22

<210> SEQ ID NO 53
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 53
aagtctggct gggcgcagtg g                                              21

<210> SEQ ID NO 54
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 54
aatggacaaa agaggtgaac tggc                                           24

<210> SEQ ID NO 55
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 55
gatagagtga aaacgcacaa tggc                                           24

<210> SEQ ID NO 56
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 56
aattaaacag ctaggtcaat atgagg                                         26

<210> SEQ ID NO 57
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 57
ggtctccact atcaagggac aag                                            23

<210> SEQ ID NO 58
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 58
aagcagctgt tagtcatttc cagg                                           24

<210> SEQ ID NO 59
```

```
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 59
aggcatcctc agattatggc tcc                                              23

<210> SEQ ID NO 60
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 60
cctgagtaac actgagaccc tgc                                              23

<210> SEQ ID NO 61
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 61
aacactcaag ctgtcaagag acac                                             24

<210> SEQ ID NO 62
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 62
attcaggcca ggcgcagtgg c                                                21

<210> SEQ ID NO 63
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 63
taaatcgtaa aactgccaca aagc                                             24

<210> SEQ ID NO 64
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 64
cagaggagta ggagaaggaa aagg                                             24

<210> SEQ ID NO 65
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 65
```
ggtagctatc taccaagtag aatcc            25

<210> SEQ ID NO 66
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 66
atcagattgg aaaaagtccc aaagc            25

<210> SEQ ID NO 67
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 67
ctcctgaaaa gcacctactc agc              23

<210> SEQ ID NO 68
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 68
ctccttaaac ctgaggtact ggg              23

<210> SEQ ID NO 69
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 69
ttttctccta atagaccacc attcc            25

<210> SEQ ID NO 70
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 70
ctgctgtatt accatcactc atgtc            25

<210> SEQ ID NO 71
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 71
ctggccaaca tagtgaaacc acg              23

<210> SEQ ID NO 72
<211> LENGTH: 27
<212> TYPE: DNA

```
<213> ORGANISM: Artificial Sequence
<220> FEATURE:
<223> OTHER INFORMATION: Synthetic oligonucleotide

<400> SEQUENCE: 72
atttgaatag gggttaaagt atcattg                                              27

<210> SEQ ID NO 73
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 73
cacttcagtg gaagttggca tgc                                                  23

<210> SEQ ID NO 74
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 74
gtttttcttc gaagtgataa acatacg                                              27

<210> SEQ ID NO 75
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 75
gctccttagt ctatgtacct gtgg                                                 24

<210> SEQ ID NO 76
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 76
tactctggca tggtaactgg tgc                                                  23

<210> SEQ ID NO 77
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 77
acaaaggact aggtctgtgg agc                                                  23

<210> SEQ ID NO 78
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 78
ccaagtttac caaattacca aagttacc                                             28
```

<210> SEQ ID NO 79
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 79
tgagccgata tcacgccact gc                                            22

<210> SEQ ID NO 80
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 80
tcccaataaa ggttttggcc cagg                                          24

<210> SEQ ID NO 81
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 81
ctgggtagca aattagggaa cagg                                          24

<210> SEQ ID NO 82
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 82
ctggccagaa aagacagttt tatcc                                         25

<210> SEQ ID NO 83
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 83
ggttcccagg aagggataac acc                                           23

<210> SEQ ID NO 84
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 84
tcactccagg aggttccatt tcc                                           23

<210> SEQ ID NO 85
<211> LENGTH: 24
<212> TYPE: DNA
<213> ORGANISM: Artificial Sequence
<220> FEATURE:

<223> OTHER INFORMATION: Synthetic oligonucleotide

<400> SEQUENCE: 85
aggcttggaa ataagcagca gtgg                                              24

<210> SEQ ID NO 86
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 86
attcatacaa tggaatacta ctcagc                                            26

<210> SEQ ID NO 87
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 87
taagtgatcc tcccacctca acc                                               23

<210> SEQ ID NO 88
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 88
tataagagga agactggggc tgg                                               23

<210> SEQ ID NO 89
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 89
tcatacttat gcaggttata ggagg                                             25

<210> SEQ ID NO 90
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 90
caagatcacg ccactgcact cc                                                22

<210> SEQ ID NO 91
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 91
aaaataaata gctggtgctc aagatc                                            26

```
<210> SEQ ID NO 92
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 92
caccagcctc attcaacaga tgg                                             23

<210> SEQ ID NO 93
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 93
caatgcagcc tcaacctcct gg                                              22

<210> SEQ ID NO 94
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 94
gttaggtcag gtgctcatgt ctg                                             23

<210> SEQ ID NO 95
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 95
aagtttcaaa aggacatgta caaaatg                                         27

<210> SEQ ID NO 96
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 96
tcctgaagag gctgcagctt cc                                              22

<210> SEQ ID NO 97
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 97
ctggtgcaca ttcccaagtg tgc                                             23

<210> SEQ ID NO 98
<211> LENGTH: 24
<212> TYPE: DNA
<213> ORGANISM: Artificial Sequence
<220> FEATURE:
<223> OTHER INFORMATION: Synthetic oligonucleotide
```

<400> SEQUENCE: 98
catgttggcc atgttcttct gagg                                    24

<210> SEQ ID NO 99
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 99
ctcagcctcc cgagtagctg g                                       21

<210> SEQ ID NO 100
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 100
aaagacattt aagaggagat gaggc                                   25

<210> SEQ ID NO 101
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 101
tgctgggatt acaggcgtga gc                                      22

<210> SEQ ID NO 102
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 102
tgtgacttcc atccgcagct cc                                      22

<210> SEQ ID NO 103
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 103
gacacttttg tggagctttc atgg                                    24

<210> SEQ ID NO 104
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 104
catgtgaggg ggcacgtctt gc                                      22

<210> SEQ ID NO 105
<211> LENGTH: 25

```
<212> TYPE: DNA
<213> ORGANISM: Artificial Sequence
<220> FEATURE:
<223> OTHER INFORMATION: Synthetic oligonucleotide

<400> SEQUENCE: 105
tcttctctat gagaaaagtg gttgc                                           25

<210> SEQ ID NO 106
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 106
tggcaaaatg ctatcgagct gcc                                             23

<210> SEQ ID NO 107
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 107
tatgaacaca gccggcctca gg                                              22

<210> SEQ ID NO 108
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 108
gaggttgcag tgagctgaga tcg                                             23

<210> SEQ ID NO 109
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 109
gtcaagcacc cagtccgata cc                                              22

<210> SEQ ID NO 110
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 110
atctgggctt ggtggcgcac g                                               21

<210> SEQ ID NO 111
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 111
```
gttaagcggg tcccacatca gc					22

<210> SEQ ID NO 112
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 112
cagccagttt cagtagaaag atgc					24

<210> SEQ ID NO 113
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 113
gacccaagca taaggggact agc					23

<210> SEQ ID NO 114
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 114
cccaaaaagt ttacaagaga aattttc					27

<210> SEQ ID NO 115
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 115
cgcctgtagt cccagctact cg					22

<210> SEQ ID NO 116
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 116
cgcgtgatgc ggaaaagaaa tcc					23

<210> SEQ ID NO 117
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 117
tctactatga accctccttc agac					24

<210> SEQ ID NO 118
<211> LENGTH: 23
<212> TYPE: DNA
<213> ORGANISM: Artificial Sequence

```
<220> FEATURE:
<223> OTHER INFORMATION: Synthetic oligonucleotide

<400> SEQUENCE: 118
gtgctgggat tacaggtgtg agc                                           23

<210> SEQ ID NO 119
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 119
ttatccaaat gtcccagggc agg                                           23

<210> SEQ ID NO 120
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 120
ctgccagcac tgctcgccag c                                             21

<210> SEQ ID NO 121
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 121
gctactgcag gcagtgcctt cc                                            22

<210> SEQ ID NO 122
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 122
catccaagcc caaggtgtca gg                                            22

<210> SEQ ID NO 123
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 123
tgtttgcatg taatttcagg aagcc                                         25

<210> SEQ ID NO 124
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 124
gatccgtcac tgttaacact cagg                                          24
```

<210> SEQ ID NO 125
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 125
ctcacagtca caagctcctg agc                                           23

<210> SEQ ID NO 126
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 126
gagatgatgc tggggtcaca gg                                            22

<210> SEQ ID NO 127
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 127
ttagaagaat gggatcgcaa agg                                           23

<210> SEQ ID NO 128
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 128
cggtattcaa atatgaggtc aggc                                          24

<210> SEQ ID NO 129
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 129
gtaaatcctg ctgccagtct tcc                                           23

<210> SEQ ID NO 130
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 130
acagggtcag acagagcctt gg                                            22

<210> SEQ ID NO 131
<211> LENGTH: 27
<212> TYPE: DNA
<213> ORGANISM: Artificial Sequence
<220> FEATURE:
<223> OTHER INFORMATION: Synthetic oligonucleotide

```
<400> SEQUENCE: 131
agttattgat ctaactatac aacaagc                                              27

<210> SEQ ID NO 132
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 132
aaagactagg ggccggggac g                                                    21

<210> SEQ ID NO 133
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 133
ctggtagaaa taaagacaac aaagcc                                               26

<210> SEQ ID NO 134
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 134
gtgccaagta attaaaagtt tgaaacc                                              27

<210> SEQ ID NO 135
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 135
ggcttttgaa gggagcacca cc                                                   22

<210> SEQ ID NO 136
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 136
gaaggataaa tacctatgat actttcc                                              27

<210> SEQ ID NO 137
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 137
ggcagggaaa tactgtgctt caag                                                 24

<210> SEQ ID NO 138
```

```
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 138
gtggtgaaat tccacctcag tacc                                          24

<210> SEQ ID NO 139
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 139
tcccaaagtg ctgggattac agg                                           23

<210> SEQ ID NO 140
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 140
gaaattagca aacaatgcca agacg                                         25

<210> SEQ ID NO 141
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 141
taagtattgg accgggaagg agg                                           23

<210> SEQ ID NO 142
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 142
ctatcatttt gctcaaagtg tagcc                                         25

<210> SEQ ID NO 143
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 143
atttcacaaa ctacagaggc cagg                                          24

<210> SEQ ID NO 144
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 144
```

```
tagacttctg tctctctatg ctgc                                              24
```

<210> SEQ ID NO 145
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 145

```
tgagtgagct gccatgtgat acc                                               23
```

<210> SEQ ID NO 146
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 146

```
acttcacacc agcctgtcca cc                                                22
```

<210> SEQ ID NO 147
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 147

```
taactcatat cctcagagag accc                                              24
```

<210> SEQ ID NO 148
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 148

```
agaggttcct cgattcccct gc                                                22
```

<210> SEQ ID NO 149
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 149

```
gtgtcagcgt cccaacacaa agc                                               23
```

<210> SEQ ID NO 150
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 150

```
gaaagtggat gggcaagcat tgc                                               23
```

<210> SEQ ID NO 151
<211> LENGTH: 22
<212> TYPE: DNA

<210> SEQ ID NO 151
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 151
gtgatcacct cacagctgca gg                                    22

<210> SEQ ID NO 152
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 152
gtttgtttag tcaaggcatt tcacc                                 25

<210> SEQ ID NO 153
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 153
cctcagcctc cagagtagct gg                                    22

<210> SEQ ID NO 154
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 154
taaaagaaaa ctcctccttc ctgg                                  24

<210> SEQ ID NO 155
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 155
aatgtgctat gtctttaaat ccatgg                                26

<210> SEQ ID NO 156
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 156
agctggcaaa tctggtaata taaaag                                26

<210> SEQ ID NO 157
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 157
gcttgaacct ggaaggtgga gg                                    22

<210> SEQ ID NO 158
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 158
gcaggcatgc taagaccttc agc                                              23

<210> SEQ ID NO 159
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 159
cagctccatg aataactcca cagg                                             24

<210> SEQ ID NO 160
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 160
gcttgaaccc aggaggcaga gg                                               22

<210> SEQ ID NO 161
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 161
atcgaagatg ccactgcaag agg                                              23

<210> SEQ ID NO 162
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 162
ccaaccacac ttcagggat acc                                               23

<210> SEQ ID NO 163
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 163
cacgccagtc cactgatact cac                                              23

<210> SEQ ID NO 164
<211> LENGTH: 22
<212> TYPE: DNA
<213> ORGANISM: Artificial Sequence
<220> FEATURE:

<223> OTHER INFORMATION: Synthetic oligonucleotide

<400> SEQUENCE: 164
gggtttcacc atgttggcca gg                                    22

<210> SEQ ID NO 165
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 165
cccaacaaag gctctggcct gg                                    22

<210> SEQ ID NO 166
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 166
atgacagcag aggagcttca tcc                                   23

<210> SEQ ID NO 167
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 167
gcaggctacg agtaaaagga tgg                                   23

<210> SEQ ID NO 168
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 168
cgggtaaaat cttgcctcct tcc                                   23

<210> SEQ ID NO 169
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 169
aaacttaaac caatggtgga tgtgg                                 25

<210> SEQ ID NO 170
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 170
agagactgag gaactgttcc agc                                   23

```
<210> SEQ ID NO 171
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 171
gaaacggtct tggatcactg atcc                                          24

<210> SEQ ID NO 172
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 172
tgcgcatgat atcttgtttc aggg                                          24

<210> SEQ ID NO 173
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 173
ggcctccgtt taaactgttg tgc                                           23

<210> SEQ ID NO 174
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 174
gaatgctggc ccgacacagt gg                                            22

<210> SEQ ID NO 175
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 175
tcttggtata gaaaagccag ctgg                                          24

<210> SEQ ID NO 176
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 176
gcaaaagccc aagagcccct gg                                            22

<210> SEQ ID NO 177
<211> LENGTH: 23
<212> TYPE: DNA
<213> ORGANISM: Artificial Sequence
<220> FEATURE:
<223> OTHER INFORMATION: Synthetic oligonucleotide
```

<400> SEQUENCE: 177
ttctcccaaa atgagcccca agg                                    23

<210> SEQ ID NO 178
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 178
gtggtgacgt aaacaaaagg tacc                                   24

<210> SEQ ID NO 179
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 179
gcaaattcca tgtgaatctt attggc                                 26

<210> SEQ ID NO 180
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 180
cctgatctat ggaacagtgg tgg                                    23

<210> SEQ ID NO 181
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 181
gttacaaacg ttgcagtttg caacg                                  25

<210> SEQ ID NO 182
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 182 gaacccgtc aacagtgatc acc                                     23

<210> SEQ ID NO 183
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 183
acaggacctc aaggcaagga gc                                     22

<210> SEQ ID NO 184
<211> LENGTH: 27

<212> TYPE: DNA
<213> ORGANISM: Artificial Sequence
<220> FEATURE:
<223> OTHER INFORMATION: Synthetic oligonucleotide

<400> SEQUENCE: 184 cataccctaaa atagaaatgt ctatccc                                27

<210> SEQ ID NO 185
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 185
gagttgcata tatgttttat aaatccc                                 27

<210> SEQ ID NO 186
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 186
tgagcccaca tccataaagt tagc                                    24

<210> SEQ ID NO 187
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 187
accgcaacct ttgccgcctg g                                       21

<210> SEQ ID NO 188
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 188
taaatatttt gtatggagtc accacc                                  26

<210> SEQ ID NO 189
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 189
aaagccagga gaaaagtta tgagg                                    25

<210> SEQ ID NO 190
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 190
tcccaaagtc ccaggattac agg    23

<210> SEQ ID NO 191
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 191
tcactatgga gcatctccga tgg    23

<210> SEQ ID NO 192
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 192
agttccctgg aagtctccga gg    22

<210> SEQ ID NO 193
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 193
aaaataatca cccagcccac atcc    24

<210> SEQ ID NO 194
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 194
acaaaactac agacacagaa agtgg    25

<210> SEQ ID NO 195
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 195
tttgggaggc tgaggtaggt gg    22

<210> SEQ ID NO 196
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 196
aaagacagtg aaacatctat aaggg    25

<210> SEQ ID NO 197
<211> LENGTH: 22
<212> TYPE: DNA
<213> ORGANISM: Artificial Sequence

```
<220> FEATURE:
<223> OTHER INFORMATION: Synthetic oligonucleotide

<400> SEQUENCE: 197
cattttggga gaccagggca gg                                              22

<210> SEQ ID NO 198
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 198
gcatgggaca gacacaaagc agc                                             23

<210> SEQ ID NO 199
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 199
gaataacaaa gagagccggc tgg                                             23

<210> SEQ ID NO 200
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 200
taaacctttt attgaaaatt gtcaaatgg                                       29

<210> SEQ ID NO 201
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 201
cgcctcagcc tcccaaagtg c                                               21

<210> SEQ ID NO 202
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 202
tacattagtt ttataggtcc agtagg                                          26

<210> SEQ ID NO 203
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 203
gaaggtttat tcatattaaa atgtgcc                                         27
```

<210> SEQ ID NO 204
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 204
ctggcttctg tggtttgagt tgg                                              23

<210> SEQ ID NO 205
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 205
acagacctac ctcctaagga tgg                                              23

<210> SEQ ID NO 206
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 206
gctagctttt gtgtgtaaga atggg                                            25

<210> SEQ ID NO 207
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 207
ggcctactca cacaatagaa tacc                                             24

<210> SEQ ID NO 208
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 208
gcaccattgc actccagcct gg                                               22

<210> SEQ ID NO 209
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 209
gaaattagga taaaggttgt cacagc                                           26

<210> SEQ ID NO 210
<211> LENGTH: 25
<212> TYPE: DNA
<213> ORGANISM: Artificial Sequence
<220> FEATURE:
<223> OTHER INFORMATION: Synthetic oligonucleotide

```
<400> SEQUENCE: 210
cagaagtgtt caaggtgaaa ctgtc                                           25

<210> SEQ ID NO 211
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 211
ctgaatcatg aaatgttcta ctctgc                                          26

<210> SEQ ID NO 212
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 212
tgtcaacttg actgggccat acg                                             23

<210> SEQ ID NO 213
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 213
ctcccgtata gttgggatta tagg                                            24

<210> SEQ ID NO 214
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 214
gcttggagtt ccttgaaatt cttgg                                           25

<210> SEQ ID NO 215
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 215
cctggtggct ccagttttct acc                                             23

<210> SEQ ID NO 216
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 216
aactcctgac ctcatgatcc acc                                             23

<210> SEQ ID NO 217
```

```
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 217
gctgggatta caggcatgag cc                                                  22

<210> SEQ ID NO 218
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 218
ttctccttta tccttggtga cattc                                               25

<210> SEQ ID NO 219
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 219
tcccaaagtg ctgggattac agg                                                 23

<210> SEQ ID NO 220
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 220
gtcataagtc agggaccatc tgc                                                 23

<210> SEQ ID NO 221
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 221
ctgtttcatt gatttccaga ctggc                                               25

<210> SEQ ID NO 222
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 222
gcaatctcgg ctcactgcaa gc                                                  22

<210> SEQ ID NO 223
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 223
```

-continued gaagaagtga ctatatcaga tctgg                        25

<210> SEQ ID NO 224
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 224
ttcaccatgt tggccaggct gg                           22

<210> SEQ ID NO 225
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 225
catcactgaa gatgacaact gagc                         24

<210> SEQ ID NO 226
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 226
gtccagcctg ggcgatagag c                            21

<210> SEQ ID NO 227
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 227
gaggaaagtc tttgaagagg aacc                         24

<210> SEQ ID NO 228
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 228
ggtacactca ccagcagttt tgc                          23

<210> SEQ ID NO 229
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 229
gagcaactgg tgtgaataca tatgg                        25

<210> SEQ ID NO 230
<211> LENGTH: 23
<212> TYPE: DNA

<213> ORGANISM: Artificial Sequence
<220> FEATURE:
<223> OTHER INFORMATION: Synthetic oligonucleotide

<400> SEQUENCE: 230
caatacctgg caccacatac acc                                    23

<210> SEQ ID NO 231
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 231
gggactacag gcatgtgcca cc                                     22

<210> SEQ ID NO 232
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 232
cggtggctca cgcgtgtaat cc                                     22

<210> SEQ ID NO 233
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 233
caactgttaa atctctcatg gaaacc                                 26

<210> SEQ ID NO 234
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 234
gacaaaggat tagaaatgca ccc                                    23

<210> SEQ ID NO 235
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 235
ggaaatgttc taaaactgga ttgtgg                                 26

<210> SEQ ID NO 236
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 236
aataataata gccaggtgtg gtagc                                  25

<210> SEQ ID NO 237
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 237
ctggaacact cacacattgc tgg                                              23

<210> SEQ ID NO 238
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 238
ctgggtgaca gagcgagact cc                                               22

<210> SEQ ID NO 239
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 239
cccaaatcat ccccgtgaaa catgc                                            25

<210> SEQ ID NO 240
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 240
gaccctgcaa tcccaacact gg                                               22

<210> SEQ ID NO 241
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 241
ctctcaggcc ttcaaactac acc                                              23

<210> SEQ ID NO 242
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 242
caggaaaggg ctcgctcagt gg                                               22

<210> SEQ ID NO 243
<211> LENGTH: 23
<212> TYPE: DNA
<213> ORGANISM: Artificial Sequence
<220> FEATURE:

<223> OTHER INFORMATION: Synthetic oligonucleotide

<400> SEQUENCE: 243
atctgcaaaa gcagcagagc agg                                              23

<210> SEQ ID NO 244
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 244
gtacccatga cagacaagtt ttagg                                            25

<210> SEQ ID NO 245
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 245
cttatcccct actgtctcct ttgg                                             24

<210> SEQ ID NO 246
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 246
ggatggtctc gatctcctga cc                                               22

<210> SEQ ID NO 247
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 247
aggttagaga ccttcctcta atgc                                             24

<210> SEQ ID NO 248
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 248
agctgggatt acaggtgcct gc                                               22

<210> SEQ ID NO 249
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 249
gctgaggcag gttggggctg c                                                21

```
<210> SEQ ID NO 250
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 250
acatttaacg tctcctaact tctcc                                          25

<210> SEQ ID NO 251
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 251
gtgctgcgat tacaggtgtg agc                                            23

<210> SEQ ID NO 252
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 252
tatgacagca gtattatact atcacc                                         26

<210> SEQ ID NO 253
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 253
ctggggacca aatctgaact gcc                                            23

<210> SEQ ID NO 254
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 254
gtagctattg ttatttccaa aagagg                                         26

<210> SEQ ID NO 255
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 255
gcttgggacc ccaggacaag g                                              21

<210> SEQ ID NO 256
<211> LENGTH: 22
<212> TYPE: DNA
<213> ORGANISM: Artificial Sequence
<220> FEATURE:
<223> OTHER INFORMATION: Synthetic oligonucleotide
```

<400> SEQUENCE: 256
cctggccaac atggggaaat cc                                          22

<210> SEQ ID NO 257
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 257
aattgcttga acctgggagg tgg                                         23

<210> SEQ ID NO 258
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 258
gcctaagacc caaaagctat tagc                                        24

<210> SEQ ID NO 259
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 259
catattaaag ggccatattc aaattgg                                     27

<210> SEQ ID NO 260
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 260
ggatgtaacc agtgtatatc acagg                                       25

<210> SEQ ID NO 261
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 261
ggaagtttag tccacatctt ctagc                                       25

<210> SEQ ID NO 262
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 262
gcacccacag gacaaccaca cg                                          22

<210> SEQ ID NO 263
<211> LENGTH: 22

```
<212> TYPE: DNA
<213> ORGANISM: Artificial Sequence
<220> FEATURE:
<223> OTHER INFORMATION: Synthetic oligonucleotide

<400> SEQUENCE: 263
gggacgcgcc tgttaacaaa gg                                              22

<210> SEQ ID NO 264
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 264
gggctggggg ccacgctcc                                                  19

<210> SEQ ID NO 265
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 265
cgcaaaagtg aagccctcct gg                                              22

<210> SEQ ID NO 266
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 266
gaaatcctac ttgatctaaa gtgagc                                          26

<210> SEQ ID NO 267
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 267
tttgagcaac ttggaaaaaa taagcg                                          26

<210> SEQ ID NO 268
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 268
ttcccaaaag acaaatagca cttcc                                           25

<210> SEQ ID NO 269
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 269
```

```
ccattttgaa aatcacagtg aattcc                                          26

<210> SEQ ID NO 270
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 270
gaaaagaaaa ccctgaattc aaaagg                                          26

<210> SEQ ID NO 271
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 271
tgctgaaaag aagcatttaa aagtgg                                          26

<210> SEQ ID NO 272
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 272
ctcttaccag tttcagagct ttcc                                            24

<210> SEQ ID NO 273
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 273
ttttcagcca aaaatcaagg acagg                                           25

<210> SEQ ID NO 274
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 274
cttgagccca ggagtttgag acc                                             23

<210> SEQ ID NO 275
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 275
cgcctgtagt accctctact agg                                             23

<210> SEQ ID NO 276
<211> LENGTH: 26
<212> TYPE: DNA
<213> ORGANISM: Artificial Sequence
```

```
<220> FEATURE:
<223> OTHER INFORMATION: Synthetic oligonucleotide

<400> SEQUENCE: 276
ggtaaagaaa gaaggatttg aaaacc                                          26

<210> SEQ ID NO 277
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 277
taagagtaat gaggttaaag tttatgc                                         27

<210> SEQ ID NO 278
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 278 cattttatt gtcacaggcc atttgc                                           26

<210> SEQ ID NO 279
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 279
gccacgcctt ctcttctgcc acc                                             23

<210> SEQ ID NO 280
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 280
tgcctctcct gactgcactg tg                                              22

<210> SEQ ID NO 281
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 281
ccatgctcta ccacgccctt gg                                              22

<210> SEQ ID NO 282
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 282
cattcaggct ggagtgcggt gg                                              22
```

<210> SEQ ID NO 283
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 283
cttaaaaatt gtctggctaa gacattg                                                27

<210> SEQ ID NO 284
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 284
ttgctcttgt tgcccgggtt gg                                                     22

<210> SEQ ID NO 285
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 285
gagcttagag gaaaagtatt atttcc                                                 26

<210> SEQ ID NO 286
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 286
tggtgctgtg ccagacgctg g                                                      21

<210> SEQ ID NO 287
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 287
cagatctttt tggctattgt cttgg                                                  25

<210> SEQ ID NO 288
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 288
gaaggaaagg gcctcccact gc                                                     22

<210> SEQ ID NO 289
<211> LENGTH: 23
<212> TYPE: DNA
<213> ORGANISM: Artificial Sequence
<220> FEATURE:
<223> OTHER INFORMATION: Synthetic oligonucleotide

```
<400> SEQUENCE: 289
catgaaaaag catgctgggg agg                                          23

<210> SEQ ID NO 290
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 290
caaacataaa aaagctttaa tagaagcc                                     28

<210> SEQ ID NO 291
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 291
tcccaactat gaaaaatag aagacg                                        26

<210> SEQ ID NO 292
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 292
cacaaattag ccgggcatgg tgg                                          23

<210> SEQ ID NO 293
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 293
cttcctttac tgagtctttc taaagc                                       26

<210> SEQ ID NO 294
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 294
tgtcctttga aatgtaggta tgtgg                                        25

<210> SEQ ID NO 295
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 295
ggatcttgca atactgacat ctcc                                         24

<210> SEQ ID NO 296
```

```
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 296
atttgaaaag aactgaagga tctacc                                              26

<210> SEQ ID NO 297
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 297
gtgagctgag atctcgtctc tgc                                                 23

<210> SEQ ID NO 298
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 298
tttgtctgaa acagattcta aaagttgg                                            28

<210> SEQ ID NO 299
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 299
gcaggtgcct gtagtcccag c                                                   21

<210> SEQ ID NO 300
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 300
gtttgagctt ctaaaattca tggattc                                             27

<210> SEQ ID NO 301
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 301
gtggtaggtc aaaccgcaat tcc                                                 23

<210> SEQ ID NO 302
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 302
```
accaaatcag acatatcagc tttgg                                          25

<210> SEQ ID NO 303
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 303
cacagaacgg atcctcaata aagg                                           24

<210> SEQ ID NO 304
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 304
gttaactcct cccttctctt tatgg                                          25

<210> SEQ ID NO 305
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 305
gtgttcagag agcttgattt ccagg                                          25

<210> SEQ ID NO 306
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 306
cccacttgat ttttcccaca tgg                                            23

<210> SEQ ID NO 307
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 307
atttatttag atgaagtgaa tattttcc                                       28

<210> SEQ ID NO 308
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 308
atttagtttg tttaactgtg agtgc                                          25

<210> SEQ ID NO 309
<211> LENGTH: 24
<212> TYPE: DNA

<213> ORGANISM: Artificial Sequence
<220> FEATURE:
<223> OTHER INFORMATION: Synthetic oligonucleotide

<400> SEQUENCE: 309
gtacagaagt gcttgatgca tacc     24

<210> SEQ ID NO 310
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 310
aggcagataa aaattctcca ttagc    25

<210> SEQ ID NO 311
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 311
acaagcacga gccacagcac c        21

<210> SEQ ID NO 312
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 312
cgctcttgtt gcccaggctg g        21

<210> SEQ ID NO 313
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 313
cccaaaacag actttctaga taacc    25

<210> SEQ ID NO 314
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 314
ttcaaattgc ttttttctta ctcacc   26

<210> SEQ ID NO 315
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 315
gatctgaaaa aagtgacagg ttgg     24

<210> SEQ ID NO 316
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 316
cactgaaatt tgaaaggaac atatgg                                    26

<210> SEQ ID NO 317
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 317
tctggtgcag tggcctctag g                                         21

<210> SEQ ID NO 318
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 318
accataagtg gttttacctg atgg                                      24

<210> SEQ ID NO 319
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 319
cccaggcgca ggtgattctc c                                         21

<210> SEQ ID NO 320
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 320
ggtggctcac gcctgaaatc c                                         21

<210> SEQ ID NO 321
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 321
cacagtccac gtgccacaat cc                                        22

<210> SEQ ID NO 322
<211> LENGTH: 24
<212> TYPE: DNA
<213> ORGANISM: Artificial Sequence
<220> FEATURE:

```
<223> OTHER INFORMATION: Synthetic oligonucleotide

<400> SEQUENCE: 322
aatcatgtta acacatccct ctcc                                          24

<210> SEQ ID NO 323
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 323
gaagagagtg ttgaaaggtt aagc                                          24

<210> SEQ ID NO 324
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 324
cgagaccata ctggctaaga tgg                                           23

<210> SEQ ID NO 325
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 325
attagccaca caataaatgt tctgg                                         25

<210> SEQ ID NO 326
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 326
tttgaaaagc gttgcaatat gatgc                                         25

<210> SEQ ID NO 327
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 327
ggttgcagtg agccgagatc g                                             21

<210> SEQ ID NO 328
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 328
ggtgggagga ctgcctgagc                                               20
```

```
<210> SEQ ID NO 329
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 329
aacagagaga aaaaacacaa attacc                                          26

<210> SEQ ID NO 330
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 330
gatatctaga attcccaaat acttgg                                          26

<210> SEQ ID NO 331
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 331
gtgatagaat taaaggaaaa aataaacg                                        28

<210> SEQ ID NO 332
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 332
attgttcctt ttctaaatat tctacc                                          26

<210> SEQ ID NO 333
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 333
cagcactttg ggaggctgag g                                               21

<210> SEQ ID NO 334
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 334
cacagaggtt tcacagtgct gg                                              22

<210> SEQ ID NO 335
<211> LENGTH: 24
<212> TYPE: DNA
<213> ORGANISM: Artificial Sequence
<220> FEATURE:
<223> OTHER INFORMATION: Synthetic oligonucleotide
```

```
<400> SEQUENCE: 335
aacttctgct tctgtccata atgc                                              24

<210> SEQ ID NO 336
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 336
gcctgtaatc ccagcacttt gg                                                22

<210> SEQ ID NO 337
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 337
gccagtaaac atatgaaaag gtgc                                              24

<210> SEQ ID NO 338
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 338
aattatgtaa ataaagagtg aaaagg                                            26

<210> SEQ ID NO 339
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 339
cccctacaca gaaaaaacaa ttcc                                              24

<210> SEQ ID NO 340
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 340
tgagtgtcaa agaaaaatac aattgg                                            26

<210> SEQ ID NO 341
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 341
atacacagag aaaatgagtc cacc                                              24

<210> SEQ ID NO 342
<211> LENGTH: 23
```

```
<212> TYPE: DNA
<213> ORGANISM: Artificial Sequence
<220> FEATURE:
<223> OTHER INFORMATION: Synthetic oligonucleotide

<400> SEQUENCE: 342
aacactcccc ttctctgttt agc                                          23

<210> SEQ ID NO 343
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 343
gatattcttt gcaacctagg atgc                                         24

<210> SEQ ID NO 344
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 344
ctctaaaact aatcagcaat gtaacc                                       26

<210> SEQ ID NO 345
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 345
cacctgtaat cccagcactt tgg                                          23

<210> SEQ ID NO 346
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 346
cgtaaaactg ccacaaagct tgtagg                                       26

<210> SEQ ID NO 347
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 347
gtggcagagg tgcaagcaag c                                            21

<210> SEQ ID NO 348
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 348
```
acagaaatga caaacgcatg tacc                                          24

<210> SEQ ID NO 349
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 349
acactctctt agctaggctt tgg                                           23

<210> SEQ ID NO 350
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 350
gagcttggaa tagggcagtt cc                                            22

<210> SEQ ID NO 351
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 351
ctgggttctt taaacatgtc cagg                                          24

<210> SEQ ID NO 352
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 352
tcaagaaagg acactgcagt ggc                                           23

<210> SEQ ID NO 353
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 353
catgcacaca aactatctca ttcc                                          24

<210> SEQ ID NO 354
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 354
tagccgggca tggtggcacg                                               20

<210> SEQ ID NO 355
<211> LENGTH: 26
<212> TYPE: DNA
<213> ORGANISM: Artificial Sequence

```
<220> FEATURE:
<223> OTHER INFORMATION: Synthetic oligonucleotide

<400> SEQUENCE: 355
atcatgctga ttgaatttca aatagc                                           26

<210> SEQ ID NO 356
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 356
ttggcatgca gggcagtgac c                                                21

<210> SEQ ID NO 357
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 357
ggtggtgaga taataacacc tgc                                              23

<210> SEQ ID NO 358
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 358
ttgctatata ataatcattt gtgatcc                                          27

<210> SEQ ID NO 359
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 359
cggtaactgt tactctggga tgg                                              23

<210> SEQ ID NO 360
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 360
aggctaggtt cccttctctt cc                                               22

<210> SEQ ID NO 361
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 361
gtagtgccta gcacagagaa agc                                              23
```

<210> SEQ ID NO 362
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 362
ctagcctggg caacaagagc g                                        21

<210> SEQ ID NO 363
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 363
tctctctcct ctctgggatc ag                                       22

<210> SEQ ID NO 364
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 364
gtttgaatat ttgtatgcag caagc                                    25

<210> SEQ ID NO 365
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 365
tagaacaaat tctggcttat aaaagc                                   26

<210> SEQ ID NO 366
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 366
ccactctacc tttattcctt gcc                                      23

<210> SEQ ID NO 367
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 367
agaccagaat atgcaagcag agg                                      23

<210> SEQ ID NO 368
<211> LENGTH: 22
<212> TYPE: DNA
<213> ORGANISM: Artificial Sequence
<220> FEATURE:
<223> OTHER INFORMATION: Synthetic oligonucleotide

```
<400> SEQUENCE: 368
ggacgttttg ctggtgtctg cg                                              22

<210> SEQ ID NO 369
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 369
aaggaacaaa ctgttgtcac atgc                                            24

<210> SEQ ID NO 370
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 370
atgtagctgg gactacaggt gc                                              22

<210> SEQ ID NO 371
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 371
ggctcatgcc tgtaatccca gc                                              22

<210> SEQ ID NO 372
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 372
atgaggtttt cacacaaaaa gatgc                                           25

<210> SEQ ID NO 373
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 373
tgggcgacag agcaagactc c                                               21

<210> SEQ ID NO 374
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 374
aaatgtccct aaaagtgatc aacagc                                          26

<210> SEQ ID NO 375
```

```
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 375
cagactcagt tttacctcat cagc                                            24

<210> SEQ ID NO 376
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 376
agtgatcttt cctctttaac ctcc                                            24

<210> SEQ ID NO 377
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 377
ccagctattc aggaggccaa gg                                              22

<210> SEQ ID NO 378
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 378
cttaaacatt atgacactgt cttgc                                           25

<210> SEQ ID NO 379
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 379
ccaggtctat gaggccgttc c                                               21

<210> SEQ ID NO 380
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 380
tccaaagcat ccctacatta tacc                                            24

<210> SEQ ID NO 381
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 381
```
acatacatac atgcagtgac tagc                                          24

<210> SEQ ID NO 382
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 382
tacaggtgcc agccaccatg c                                             21

<210> SEQ ID NO 383
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 383
gcctgtaatc ccagcactct gg                                            22

<210> SEQ ID NO 384
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 384
gacagagtcc cactcttgtt gc                                            22

<210> SEQ ID NO 385
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 385
gtgccttcca aagcagtgta gg                                            22

<210> SEQ ID NO 386
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 386
tatcttactg ggtatgtata atgcc                                         25

<210> SEQ ID NO 387
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 387
caaaggaaat acgtcctacc agg                                           23

<210> SEQ ID NO 388
<211> LENGTH: 23
<212> TYPE: DNA

```
<213> ORGANISM: Artificial Sequence
<220> FEATURE:
<223> OTHER INFORMATION: Synthetic oligonucleotide

<400> SEQUENCE: 388 cctttctca cagacatgct tcc                                           23

<210> SEQ ID NO 389
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 389
taaacacagt gagcagaatc cc                                           22

<210> SEQ ID NO 390
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 390
ataaagcaaa cttctaaaag ggtcc                                        25

<210> SEQ ID NO 391
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 391
accactacac tccagcctgg g                                            21

<210> SEQ ID NO 392
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 392
gatacctggg tcagagtaag tgc                                          23

<210> SEQ ID NO 393
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 393
tgtaatctca gctacttggg agg                                          23

<210> SEQ ID NO 394
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 394
gtgtcgtctt ctcttcctct acg                                          23
```

<210> SEQ ID NO 395
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 395
ctggctagta tgaggttggt gc                                              22

<210> SEQ ID NO 396
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 396
ggactagcca catttcaacc agg                                             23

<210> SEQ ID NO 397
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 397
gcagtatact gagaatttag tttcc                                           25

<210> SEQ ID NO 398
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 398
gaggctgagg caggagaatg g                                               21

<210> SEQ ID NO 399
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 399
cattgtttga tgaaggtcaa cagc                                            24

<210> SEQ ID NO 400
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 400
cagacaagag tggctacggc ag                                              22

<210> SEQ ID NO 401
<211> LENGTH: 22
<212> TYPE: DNA
<213> ORGANISM: Artificial Sequence
<220> FEATURE:

<223> OTHER INFORMATION: Synthetic oligonucleotide

<400> SEQUENCE: 401
acgcccagcc agattattca gg                                    22

<210> SEQ ID NO 402
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 402
ggaaccagaa agaagtgcaa agg                                   23

<210> SEQ ID NO 403
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 403
tgagccatct tggaggcagg c                                     21

<210> SEQ ID NO 404
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 404
caggaccttc ctacaaacct cc                                    22

<210> SEQ ID NO 405
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 405
aacacaacat atctgacctt acgc                                  24

<210> SEQ ID NO 406
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 406
gccttagaag tccagaggaa agc                                   23

<210> SEQ ID NO 407
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 407
tgacgtaccc agtagacctt cc                                    22

```
<210> SEQ ID NO 408
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 408
ctctgcaagc ctgggaaaca gg                                              22

<210> SEQ ID NO 409
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 409
gccttgtccc caagtcctaa gg                                              22

<210> SEQ ID NO 410
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 410
gcaaagggac tcctggaatt cc                                              22

<210> SEQ ID NO 411
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 411
gctcctgcct gtaatcccag c                                               21

<210> SEQ ID NO 412
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 412
gaaggaaaca gaaaaagcag aggc                                            24

<210> SEQ ID NO 413
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 413
cttactaccg ttcttcttca ctgg                                            24

<210> SEQ ID NO 414
<211> LENGTH: 27
<212> TYPE: DNA
<213> ORGANISM: Artificial Sequence
<220> FEATURE:
<223> OTHER INFORMATION: Synthetic oligonucleotide
```

```
<400> SEQUENCE: 414
actattctgt tctttaggt ttactgc                                          27

<210> SEQ ID NO 415
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 415
cggtggctca cacctgtaat cc                                              22

<210> SEQ ID NO 416
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 416
agccagagtt ctgtgctcta gg                                              22

<210> SEQ ID NO 417
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 417
taatttgcat ttcgtgccgc tcc                                             23

<210> SEQ ID NO 418
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 418
cacttttaat acagatccca atagg                                           25

<210> SEQ ID NO 419
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 419
atgtattttt tcttttcctg tcaagc                                          26

<210> SEQ ID NO 420
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 420
aaatgttaac attattctcc ctaagg                                          26

<210> SEQ ID NO 421
<211> LENGTH: 22
```

```
<212> TYPE: DNA
<213> ORGANISM: Artificial Sequence
<220> FEATURE:
<223> OTHER INFORMATION: Synthetic oligonucleotide

<400> SEQUENCE: 421
catatgccca gatcccgtct cc                                           22

<210> SEQ ID NO 422
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 422
acaggtgtga gccgctgcac c                                            21

<210> SEQ ID NO 423
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 423
gccaagacgt ttacagtttt ggc                                          23

<210> SEQ ID NO 424
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 424
aggaaacttc tgaggatgat ggg                                          23

<210> SEQ ID NO 425
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 425
gctttatagg gcagtctgaa ttcc                                         24

<210> SEQ ID NO 426
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 426
ttagaataaa agttatctcg ggagg                                        25

<210> SEQ ID NO 427
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 427
```
taatttcttc agctttatcc ctcag            25

<210> SEQ ID NO 428
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 428
cacatgacta attctctatt cattcc            26

<210> SEQ ID NO 429
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 429
aaagacctca agaaaagagt cacc            24

<210> SEQ ID NO 430
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 430
gacccataaa gattatatgc ccag            24

<210> SEQ ID NO 431
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 431
aaagtactaa tgcagtgtgt cagc            24

<210> SEQ ID NO 432
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 432
gaggttcctc gattcccctg c            21

<210> SEQ ID NO 433
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 433
ggagagcaga ggaattcaca gg            22

<210> SEQ ID NO 434
<211> LENGTH: 26
<212> TYPE: DNA
<213> ORGANISM: Artificial Sequence -continued

```
<220> FEATURE:
<223> OTHER INFORMATION: Synthetic oligonucleotide

<400> SEQUENCE: 434
agtaattaga aactgattct aagacg                                            26

<210> SEQ ID NO 435
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 435
cataccattg ccaatccagt tcc                                               23

<210> SEQ ID NO 436
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 436
attacgggtg cctgccactg c                                                 21

<210> SEQ ID NO 437
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 437
cagccaggca gaggagagag g                                                 21

<210> SEQ ID NO 438
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 438
ttttcattcc aagtttctgt ttggg                                             25

<210> SEQ ID NO 439
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 439
tttcaaatag gaatttggat aatccc                                            26

<210> SEQ ID NO 440
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 440
taagccgaga tcacaccact gc                                                22
```

```
<210> SEQ ID NO 441
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 441
ccttcagcgc attatatctt ggc                                          23

<210> SEQ ID NO 442
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 442
ccatctaatc catcttaaat tcacc                                        25

<210> SEQ ID NO 443
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 443
gagtggagac tgcgccactg c                                            21

<210> SEQ ID NO 444
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 444
aatcatgtgc caattaaacc atggc                                        25

<210> SEQ ID NO 445
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 445
cccagggacc agaccagacc                                              20

<210> SEQ ID NO 446
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 446
ctcactcacc agtgaaaatc agc                                          23

<210> SEQ ID NO 447
<211> LENGTH: 22
<212> TYPE: DNA
<213> ORGANISM: Artificial Sequence
<220> FEATURE:
<223> OTHER INFORMATION: Synthetic oligonucleotide
```

```
<400> SEQUENCE: 447
ggttgctctc gaactcctga cc                                                22

<210> SEQ ID NO 448
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 448
gttcccccag ctcctttctg c                                                 21

<210> SEQ ID NO 449
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 449
agaaagatgt agaagggtcc agc                                               23

<210> SEQ ID NO 450
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 450
gggaaaaggt gtattatgca agcg                                              24

<210> SEQ ID NO 451
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 451
ctctctcaga cctaatgcaa aagc                                              24

<210> SEQ ID NO 452
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 452
aactatacat acagtatttg tattagc                                           27

<210> SEQ ID NO 453
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 453
aaattaatgc aatccatgat ccagg                                             25

<210> SEQ ID NO 454
```

```
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 454
ctttctccac tctaagagaa ccc                                             23

<210> SEQ ID NO 455
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 455
ttttggtgtg ttcatattgg ctgc                                            24

<210> SEQ ID NO 456
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 456
gcttccacaa atgacagaca aagg                                            24

<210> SEQ ID NO 457
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 457
ggctcatgct tgtaatccca gc                                              22

<210> SEQ ID NO 458
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 458
catatgaatt gttgttcctt tgtagg                                          26

<210> SEQ ID NO 459
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 459
cactggtaca agtccaagag tcc                                             23

<210> SEQ ID NO 460
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 460
```
gaccctgtgt ctacttcctg gg                                              22

<210> SEQ ID NO 461
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 461
tatttgaact atctcttgaa atgtcc                                          26

<210> SEQ ID NO 462
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 462
ctgattaaaa agtattaccc ttggc                                           25

<210> SEQ ID NO 463
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 463
tttgaaactg cactcaataa cttgg                                           25

<210> SEQ ID NO 464
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 464
agtaatgtgt catgatccaa tggc                                            24

<210> SEQ ID NO 465
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 465
gaaagcattt cccaatgtct cacc                                            24

<210> SEQ ID NO 466
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 466
caatggacaa aaggcccaac tgc                                             23

<210> SEQ ID NO 467
<211> LENGTH: 24
<212> TYPE: DNA

```
<213> ORGANISM: Artificial Sequence
<220> FEATURE:
<223> OTHER INFORMATION: Synthetic oligonucleotide

<400> SEQUENCE: 467
tccagctctg gctttttttgt taag                                              24

<210> SEQ ID NO 468
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 468
acggagtctc actccgtgac c                                                  21

<210> SEQ ID NO 469
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 469
ctatgtcata gtcaagagac tttgc                                              25

<210> SEQ ID NO 470
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 470
gttcaagcga ttctcctgtc tcg                                                23

<210> SEQ ID NO 471
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 471
ccacctaata cttaaatacg gaagc                                              25

<210> SEQ ID NO 472
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 472
atattcaaca aacttaatag tgaagtg                                            27

<210> SEQ ID NO 473
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 473
ttacaggcgt gagtcaccat gc                                                 22
```

<210> SEQ ID NO 474
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 474
aacacctcca agaggccaaa cg                                              22

<210> SEQ ID NO 475
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 475
tactattggc aaatttcaat tatatgg                                         27

<210> SEQ ID NO 476
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 476
agcccacatc ctaaaattca ataag                                           25

<210> SEQ ID NO 477
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 477
gaaagtggat aagtgtttgt ctgg                                            24

<210> SEQ ID NO 478
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 478
ggccaggcat tcaagaccag c                                               21

<210> SEQ ID NO 479
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 479
agccaacaac aaaaagacac aacc                                            24

<210> SEQ ID NO 480
<211> LENGTH: 22
<212> TYPE: DNA
<213> ORGANISM: Artificial Sequence
<220> FEATURE:

<223> OTHER INFORMATION: Synthetic oligonucleotide

<400> SEQUENCE: 480
ttgagcccag gagttcaaga cc                                    22

<210> SEQ ID NO 481
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 481
cagactaaag atctcagaga gaaac                                 25

<210> SEQ ID NO 482
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 482
cgcttgtaat cccagcactt gg                                    22

<210> SEQ ID NO 483
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 483
aaaagtgaaa tcagaatttg tttcc                                 25

<210> SEQ ID NO 484
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 484
caggcgtgag caactgtgtc c                                     21

<210> SEQ ID NO 485
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 485
ggtccagtag gatctcgttt gc                                    22

<210> SEQ ID NO 486
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 486
actttgaaaa tgttgttata gctggg                                26

```
<210> SEQ ID NO 487
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 487
ttccctgcat ctaagtcttc tcc                                         23

<210> SEQ ID NO 488
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 488
agatatctac cattgaagag tttgc                                       25

<210> SEQ ID NO 489
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 489
agtcttcact tcactttgtt gtcc                                        24

<210> SEQ ID NO 490
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 490
ccatgcaggt atgaaatata aaagc                                       25

<210> SEQ ID NO 491
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 491
tgggtgacag agtgagactc c                                           21

<210> SEQ ID NO 492
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 492
acagcaatac cgggttaaca tgc                                         23

<210> SEQ ID NO 493
<211> LENGTH: 25
<212> TYPE: DNA
<213> ORGANISM: Artificial Sequence
<220> FEATURE:
<223> OTHER INFORMATION: Synthetic oligonucleotide
```

```
<400> SEQUENCE: 493
tttatgtaaa agatgaatgc gaggc                                      25

<210> SEQ ID NO 494
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 494
ctactctgct actgggaaca gg                                         22

<210> SEQ ID NO 495
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 495
caaacgttag tctggcaaaa tgcg                                       24

<210> SEQ ID NO 496
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 496
tgcacgctac cacacccagc                                            20

<210> SEQ ID NO 497
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 497
aattcttgga tctgtgtgtt tactgc                                     26

<210> SEQ ID NO 498
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 498
taccagttat cattctcttt ctgc                                       24

<210> SEQ ID NO 499
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 499
atccacccac ctcggcctcc                                            20

<210> SEQ ID NO 500
<211> LENGTH: 22
```

```
<212> TYPE: DNA
<213> ORGANISM: Artificial Sequence
<220> FEATURE:
<223> OTHER INFORMATION: Synthetic oligonucleotide

<400> SEQUENCE: 500
cactctgcct ggcccttaat gg                                           22

<210> SEQ ID NO 501
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 501
atagtttgtt taatatgcca ctaagg                                       26

<210> SEQ ID NO 502
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 502
gcgtgagcca ccgcacctgg                                              20

<210> SEQ ID NO 503
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 503
ctccatcaca caaattttat gtggc                                        25

<210> SEQ ID NO 504
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 504
agacggagtc tcgttctgtc gc                                           22

<210> SEQ ID NO 505
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 505
tcccaggttc aagccattct cc                                           22

<210> SEQ ID NO 506
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 506
```

```
tattttgaga gtctcactct gtcg                                            24

<210> SEQ ID NO 507
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 507
gtctcgaact cctgacctca gg                                              22

<210> SEQ ID NO 508
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 508
aaggaggtga agagtgaact acg                                             23

<210> SEQ ID NO 509
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 509
gtctcaggtt ttggacttac ttgg                                            24

<210> SEQ ID NO 510
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 510
tttacagatc ttaaatgcat taggac                                          26

<210> SEQ ID NO 511
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 511
gtacactgaa caaaggagac agg                                             23

<210> SEQ ID NO 512
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 512
ctggtagtaa tgcaaaatag cacc                                            24

<210> SEQ ID NO 513
<211> LENGTH: 27
<212> TYPE: DNA
<213> ORGANISM: Artificial Sequence
```

```
<220> FEATURE:
<223> OTHER INFORMATION: Synthetic oligonucleotide

<400> SEQUENCE: 513
catttaatgt gaaatgaatt ataagcc                                            27

<210> SEQ ID NO 514
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 514
gagacagggt ttcactatgt tgg                                                23

<210> SEQ ID NO 515
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 515
ccagcacttt ggaaggctga gg                                                 22

<210> SEQ ID NO 516
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 516
gaaaccaagt atcatggtaa attgc                                              25

<210> SEQ ID NO 517
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 517
cagtgagggc tgctcagttc c                                                  21

<210> SEQ ID NO 518
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 518
gccaggtgcg gtggctcacg                                                    20

<210> SEQ ID NO 519
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 519
catgcctgta atcccagcta cc                                                 22
```

<210> SEQ ID NO 520
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 520
atgtaaatgg tacagtcact ttagg                                25

<210> SEQ ID NO 521
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 521
cccacaatac agagaactct tacc                                 24

<210> SEQ ID NO 522
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 522
tgaaacatgc agcccagtgt cc                                   22

<210> SEQ ID NO 523
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 523
tgttttttct cctgccttca atcc                                 24

<210> SEQ ID NO 524
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 524
gctttcctgg gtctccatct gg                                   22

<210> SEQ ID NO 525
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 525
gcagccgctt gaaaacaaaa cagc                                 24

<210> SEQ ID NO 526
<211> LENGTH: 23
<212> TYPE: DNA
<213> ORGANISM: Artificial Sequence
<220> FEATURE:
<223> OTHER INFORMATION: Synthetic oligonucleotide

```
<400> SEQUENCE: 526
gatcacgtta catttggggg tgg                                          23

<210> SEQ ID NO 527
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 527
taggctgaaa aactaaaatt tgttgc                                       26

<210> SEQ ID NO 528
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 528
ctcctttggg ctcctttagt cc                                           22

<210> SEQ ID NO 529
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 529
gcctcggcct cccaaagtgc                                              20

<210> SEQ ID NO 530
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 530
aatgcctaga gagatttggc agg                                          23

<210> SEQ ID NO 531
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 531
gagatggggt ttcactatgt tgg                                          23

<210> SEQ ID NO 532
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 532
tgtgatcttg ccactgcact cc                                           22

<210> SEQ ID NO 533
```

```
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 533
acttctcctc catttgtttc ttcg                                              24

<210> SEQ ID NO 534
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 534
cgtgcccggg ctcagttcta c                                                 21

<210> SEQ ID NO 535
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 535
ccaaaacaat aaaatcacaa tttggg                                            26

<210> SEQ ID NO 536
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 536
ctgaactgcc ttagagtaaa tccg                                              24

<210> SEQ ID NO 537
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 537
atttctgtat caggtctgtg ttcc                                              24

<210> SEQ ID NO 538
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 538
ggctgacccc ttcactgttt cc                                                22

<210> SEQ ID NO 539
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 539
```
caaaaattag ccaggcatgg tgg                                          23

<210> SEQ ID NO 540
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 540
gcagtgagca gtgatcgcac c                                            21

<210> SEQ ID NO 541
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 541
aaagactgtg aactaacttg tttgc                                        25

<210> SEQ ID NO 542
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 542
tgccaagaat tacacattat taggc                                        25

<210> SEQ ID NO 543
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 543
ggccaggatg tcattaactt tcc                                          23

<210> SEQ ID NO 544
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 544
gtaagagctg acgtgtattg tgc                                          23

<210> SEQ ID NO 545
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 545
cccggtgagg ccgcacatcc                                              20

<210> SEQ ID NO 546
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 546
cctgcgcctt aaccccctcc                                               20

<210> SEQ ID NO 547
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 547
cggcgcctag gggccatcg                                                19

<210> SEQ ID NO 548
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 548
acttaaggaa acgaacatga cacc                                          24

<210> SEQ ID NO 549
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 549
gagaccgagt cttgctgtgt cg                                            22

<210> SEQ ID NO 550
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 550
gtattaattg aagatgattt ggaatgc                                       27

<210> SEQ ID NO 551
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 551
tctttaaaag actatcgctg aggc                                          24

<210> SEQ ID NO 552
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 552
aaaagagaca tcagtagagc atcc                                          24
```

<210> SEQ ID NO 553
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 553
gttcatgttt tctttgacgt ctcc                                          24

<210> SEQ ID NO 554
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 554
tttcgaaagt tcaggctgag tgc                                           23

<210> SEQ ID NO 555
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 555
gaccctcaaa acaatcctct aagg                                          24

<210> SEQ ID NO 556
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 556
caaaacacac ttagaaacaa actgc                                         25

<210> SEQ ID NO 557
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 557
gcctgggcga catagtgaga cc                                            22

<210> SEQ ID NO 558
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 558
ggcaggagaa tggcgtgaac c                                             21

<210> SEQ ID NO 559
<211> LENGTH: 21
<212> TYPE: DNA
<213> ORGANISM: Artificial Sequence
<220> FEATURE:

<223> OTHER INFORMATION: Synthetic oligonucleotide

<400> SEQUENCE: 559
tttgctcgtt gcccaggctg g                                    21

<210> SEQ ID NO 560
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 560
gcaacttaat gtgatagaat aatagc                               26

<210> SEQ ID NO 561
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 561
cctccccttc tgctgccagc                                      20

<210> SEQ ID NO 562
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 562
ccacaacaat gtaaactcct ctgg                                 24

<210> SEQ ID NO 563
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 563
tactctccct agagttcgtt ccc                                  23

<210> SEQ ID NO 564
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 564 gggtcccct ttggccattc c                                     21

<210> SEQ ID NO 565
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 565
gatcttggct cacttcaacc tcc                                  23

```
<210> SEQ ID NO 566
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 566 agggggaaata tttaaacctt gg                                              22

<210> SEQ ID NO 567
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 567
aatgcaatgg tgcatttaca gagg                                             24

<210> SEQ ID NO 568
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 568
tcattttatc tatttctaca tggtcc                                           26

<210> SEQ ID NO 569
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 569
ggaagggaaa tgcccatgaa cc                                               22

<210> SEQ ID NO 570
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 570
agtgaacatt ttctgcagcc tcc                                              23

<210> SEQ ID NO 571
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 571
caacaggacg tcaggcgatc c                                                21

<210> SEQ ID NO 572
<211> LENGTH: 22
<212> TYPE: DNA
<213> ORGANISM: Artificial Sequence
<220> FEATURE:
<223> OTHER INFORMATION: Synthetic oligonucleotide
```

<400> SEQUENCE: 572
ccttcaggct gtcctgaaaa gg                                      22

<210> SEQ ID NO 573
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 573
agtctcactc catcgcccag g                                       21

<210> SEQ ID NO 574
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 574
actgtgaaca gtagttaact cagg                                    24

<210> SEQ ID NO 575
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 575
gcatgcctgt aatccaagct gc                                      22

<210> SEQ ID NO 576
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 576
gaaacaattc tcttttcaca cttgc                                   25

<210> SEQ ID NO 577
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 577
ggctcatgcc tgttatccca gc                                      22

<210> SEQ ID NO 578
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 578
agaagaagct tagtcatatg tttgg                                   25

<210> SEQ ID NO 579
<211> LENGTH: 24

<212> TYPE: DNA
<213> ORGANISM: Artificial Sequence
<220> FEATURE:
<223> OTHER INFORMATION: Synthetic oligonucleotide

<400> SEQUENCE: 579
cagatgcttg agccaaacaa atgg                                  24

<210> SEQ ID NO 580
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 580
ctggcagaca gagtgagact cc                                    22

<210> SEQ ID NO 581
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 581
aatgtgtgaa tattattcat tacaggg                               27

<210> SEQ ID NO 582
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 582
gcaggagaat tgcttgaacc tgg                                   23

<210> SEQ ID NO 583
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 583
ctttagtcaa attaaaacag tctatcc                               27

<210> SEQ ID NO 584
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 584
gatttctatc tcctgcaacc acc                                   23

<210> SEQ ID NO 585
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 585

```
ttcttgtgta actactaaaa atctcc                                        26

<210> SEQ ID NO 586
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 586
aaagggtctt cataaggcta atgg                                          24

<210> SEQ ID NO 587
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 587
ctcttaagga ttatttatat gaagacc                                       27

<210> SEQ ID NO 588
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 588
caggaggagc cccagagc                                                 18

<210> SEQ ID NO 589
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 589
tcctggggat ggttggatgc                                               20

<210> SEQ ID NO 590
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 590
tgaccccaca gagtttacac agc                                           23

<210> SEQ ID NO 591
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 591
agtcagggca ggctctgcc                                                19

<210> SEQ ID NO 592
<211> LENGTH: 23
<212> TYPE: DNA
<213> ORGANISM: Artificial Sequence
```

```
<220> FEATURE:
<223> OTHER INFORMATION: Synthetic oligonucleotide

<400> SEQUENCE: 592
tattttggcc ccatccagaa agc                                           23

<210> SEQ ID NO 593
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 593
cacccagagt acagctttgt tcc                                           23

<210> SEQ ID NO 594
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 594
gaggagcccc agagcctgc                                                19

<210> SEQ ID NO 595
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 595
tggggatggt tggatgctta cc                                            22

<210> SEQ ID NO 596
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 596
cccacagagt ttacacagct tgc                                           23

<210> SEQ ID NO 597
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 597
caggctctgc ccactcacc                                                19

<210> SEQ ID NO 598
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 598
ccatccagaa agcccaaagc c                                             21
```

<210> SEQ ID NO 599
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 599
ccagagtaca gctttgttcc tcattc                                          26

<210> SEQ ID NO 600
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 600
gcagtacaaa caacgcacag cg                                              22

<210> SEQ ID NO 601
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 601
ctgccaccct ccacagtccc                                                 20

<210> SEQ ID NO 602
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 602
gccaagacca tgcatgcg                                                   18

<210> SEQ ID NO 603
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 603
cccagggaca aagagactcc c                                               21

<210> SEQ ID NO 604
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 604
caggaagcag acagtcttct agttcc                                          26

<210> SEQ ID NO 605
<211> LENGTH: 23
<212> TYPE: DNA
<213> ORGANISM: Artificial Sequence
<220> FEATURE:
<223> OTHER INFORMATION: Synthetic oligonucleotide

```
<400> SEQUENCE: 605
tgcctgtaat cccaacactt tgg                                          23

<210> SEQ ID NO 606
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 606
tccctctggc caggatggg                                               19

<210> SEQ ID NO 607
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 607
atggggaatg ggagtaggaa gc                                           22

<210> SEQ ID NO 608
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 608
cagatcagtt ctcccctcca gc                                           22

<210> SEQ ID NO 609
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 609
acaaaaaaga aacatgctca gagagg                                       26

<210> SEQ ID NO 610
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 610
tggtggcatg catctgtagt cc                                           22

<210> SEQ ID NO 611
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 611
aggtgctcta tagatgttag catccc                                       26

<210> SEQ ID NO 612
```

```
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 612
ccaggacagg atggagatct gg                                              22

<210> SEQ ID NO 613
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 613
agggaacctg tgcattatcc ttgc                                            24

<210> SEQ ID NO 614
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 614
cagaagtctt gctttaagga ggagg                                           25

<210> SEQ ID NO 615
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 615
gggtacgtga aactcaccaa gg                                              22

<210> SEQ ID NO 616
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 616
cagagtgtgg caagcaaggg                                                 20

<210> SEQ ID NO 617
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 617
aacattttaa aggtacaaat aacgtggg                                        28

<210> SEQ ID NO 618
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 618
```
tagggagcaa cagccattaa gc                                                  22

<210> SEQ ID NO 619
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 619
ggtgcactgt ccagctctgg                                                     20

<210> SEQ ID NO 620
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 620
actctcgctg aactcgcctg g                                                   21

<210> SEQ ID NO 621
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 621
ctcggtctct ggtggtacgc                                                     20

<210> SEQ ID NO 622
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 622
gcaagaggtc cgagctggg                                                      19

<210> SEQ ID NO 623
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 623
ggaagaagtg aaacaagaga tgaagg                                              26

<210> SEQ ID NO 624
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 624
cccagagaac aaaccggatt agg                                                 23

<210> SEQ ID NO 625
<211> LENGTH: 23
<212> TYPE: DNA

```
<213> ORGANISM: Artificial Sequence
<220> FEATURE:
<223> OTHER INFORMATION: Synthetic oligonucleotide

<400> SEQUENCE: 625
cccttcaacc ttctccaatc tgc                                        23

<210> SEQ ID NO 626
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 626
cccatgtcca gtggtttagg g                                          21

<210> SEQ ID NO 627
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 627
gagattggtg ggagacagat gg                                         22

<210> SEQ ID NO 628
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 628
cttctcagct caaagttcca gcg                                        23

<210> SEQ ID NO 629
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 629
gaatgggaga gatgaccaga gg                                         22

<210> SEQ ID NO 630
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 630
aagggcaagg gggtatgtgg                                            20

<210> SEQ ID NO 631
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 631
ggaaggaagc atgggaacac c                                          21
```

```
<210> SEQ ID NO 632
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 632
ccatcaatgc tctgtctgtc tgg                                              23

<210> SEQ ID NO 633
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 633
gtgccgtgac tgtgcttgg                                                   19

<210> SEQ ID NO 634
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 634
acatcccatt gacctcatca agc                                              23
```